(12) United States Patent
Samec et al.

(10) Patent No.: US 10,875,870 B2
(45) Date of Patent: Dec. 29, 2020

(54) SOLID STATE FORMS OF RUCAPARIB AND OF RUCAPARIB SALTS

(71) Applicant: ASSIA CHEMICAL INDUSTRIES LTD., Petach Tikva (IL)

(72) Inventors: Dijana Skalec Samec, Jastrebarsko (HR); Jasna Dogan, Petrinja (HR); Tomislav Biljan, Krizevci (HR); Maja Matanovic Skugor, Zagreb (HR); Moris Mihovilovic, Pula (HR); Tina Mundorfer, Zagreb (HR); Nikolina Janton, Jakovlje (HR); Mihaela Tuksar, Cakovec (HR); Sara Morasi Pipercic, Novi Marof (HR); Nea Baus, Rijeka (HR)

(*) Notice: Subject to any disclaimer, the term of this patent is extended or adjusted under 35 U.S.C. 154(b) by 0 days.

(21) Appl. No.: 16/478,509

(22) PCT Filed: Jan. 23, 2018

(86) PCT No.: PCT/US2018/014782
§ 371 (c)(1),
(2) Date: Jul. 17, 2019

(87) PCT Pub. No.: WO2018/140377
PCT Pub. Date: Aug. 2, 2018

(65) Prior Publication Data
US 2019/0389871 A1 Dec. 26, 2019

Related U.S. Application Data

(60) Provisional application No. 62/449,705, filed on Jan. 24, 2017, provisional application No. 62/465,492, filed on Mar. 1, 2017, provisional application No. 62/503,641, filed on May 9, 2017, provisional application No. 62/530,359, filed on Jul. 10, 2017, provisional application No. 62/532,062, filed on Jul. 13, 2017, provisional application No. 62/536,033, filed on Jul. 24, 2017, provisional application No. 62/573,263, filed on Oct. 17, 2017, provisional application No. 62/589,670, filed on Nov. 22, 2017.

(30) Foreign Application Priority Data

Jan. 3, 2018 (IN) .............................. 201811000359

(51) Int. Cl.
*A61K 31/55* (2006.01)
*A61P 35/00* (2006.01)
*C07D 487/06* (2006.01)

(52) U.S. Cl.
CPC ........ *C07D 487/06* (2013.01); *C07B 2200/13* (2013.01)

(58) Field of Classification Search
CPC ........ A61K 31/55; A61P 35/00; C07D 487/06
See application file for complete search history.

(56) References Cited

U.S. PATENT DOCUMENTS 6,495,541 B1 * 12/2002 Webber ................ A61K 31/277
514/212.06

FOREIGN PATENT DOCUMENTS

| WO | 2004087713 A1 | 10/2004 |
| WO | 2006033007 A2 | 3/2006 |
| WO | 2011098971 A1 | 8/2011 |

OTHER PUBLICATIONS

Adam T. Gillmore, et al., "Multkilogram Scale-Up of a Reductive Alkylation Route to a Novel PARP Inhibitor", Organic Process Research & Development, vol. 16, No. 12, pp. 1897-1904 (2012).
International Search Report and Written Opinion issued in corresponding Appl. No. PCT/US2018/014782 dated Jun. 20, 2018 (9 pages).
Communication pursuant to Rule 164(2)(b) and Article 94(3) EPC issued in corresponding European Appl. No. 18704344.3 dated Sep. 22, 2020 (11 pages).

* cited by examiner

*Primary Examiner* — Brenda L Coleman
(74) *Attorney, Agent, or Firm* — Carter, DeLuca & Farrell LLP

(57) ABSTRACT

Disclosed are solid state forms of Rucaparib and of Rucaparib salts, and pharmaceutical compositions thereof.

26 Claims, 32 Drawing Sheets

Peak at 28.47 belongs to silicon.

Peak at 28.49 belongs to silicon.

Peak at 28.48° belongs to silicon.

X-ray powder diffraction pattern of Rucaparib Form II obtained by Example 82.

Peak at 28.47° belongs to silicon.

X-ray powder diffraction pattern of Rucaparib Form II and Form III, obtained by Example 83.

Shows a characteristic solid state $^{13}C$ NMR spectrum of Form II of Rucaparib base at the range of 250-0 ppm Shows a characteristic solid state $^{13}C$ NMR spectrum of Form II of Rucaparib base at the range of 100-0 ppm Shows a characteristic solid state $^{13}$C NMR spectrum of Form II of Rucaparib base at the range of 200-100 ppm Shows a characteristic solid state $^{13}$C NMR spectrum of Form IV of Rucaparib base at the range of 250-0 ppm Shows a characteristic solid state $^{13}$C NMR spectrum of Form IV of Rucaparib Hemi-Edisylate at the range of 100-0 ppm Shows a characteristic solid state $^{13}$C NMR spectrum of Form IV of Rucaparib Hemi-Edisylate at the range of 200-100 ppm Shows a characteristic solid state $^{13}$C NMR spectrum of Form III of Rucaparib Tosylate at the range of 250-0 ppm Shows a characteristic solid state $^{13}$C NMR spectrum of Form III of Rucaparib Tosylate at the range of 100-0 ppm Shows a characteristic solid state $^{13}C$ NMR spectrum of Form III of Rucaparib Tosylate at the range of 200-100 ppm Shows a characteristic solid state $^{13}C$ NMR spectrum of Form V of Rucaparib Tosylate at the range of 250-0 ppm

SOLID STATE FORMS OF RUCAPARIB AND OF RUCAPARIB SALTS

FIELD OF THE DISCLOSURE

The present disclosure encompasses solid state forms of Rucaparib and of Rucaparib salts, and pharmaceutical compositions thereof.

BACKGROUND OF THE DISCLOSURE

Rucaparib chemical name is 8-fluoro-2-{4-[(methylamino)methyl]phenyl}-1,3,4,5-tetrahydro-6H-azepino[5,4,3-cd]indol-6-one, having the following chemical structure:

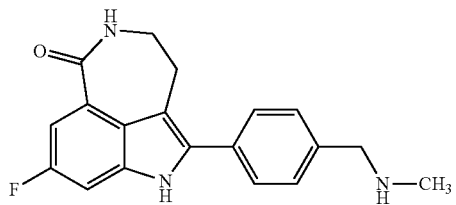 [SMILES: CNCc1ccc(-c2[nH]c3cc(F)cc4c3c2CCNC4=O)cc1]

Rucaparib S-Camsylate chemical name is 8-fluoro-2-{4-[(methylamino)methyl]phenyl}-1,3,4,5-tetrahydro-6H-azepino[5,4,3-cd]indol-6-one ((1S,4R)-7,7 dimethyl-2-oxobicyclo[2.2.1]hept-1-yl) methane-sulfonic acid salt, having the following chemical structure:

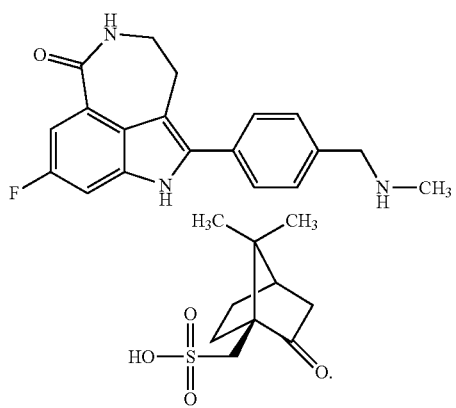

Rucaparib Hemi-Edisylate chemical name is 8-fluoro-2-{4-[(methylamino)methyl]phenyl}-1,3,4,5-tetrahydro-6H-azepino[5,4,3-cd]indol-6-one Hemi-Edisylate, having the following chemical structure:

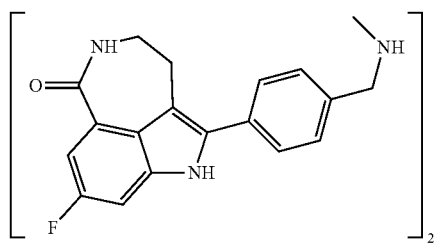

Rucaparib Tosylate chemical name is 8-fluoro-2-{4-[(methylamino)methyl]phenyl}-1,3,4,5-tetrahydro-6H-azepino[5,4,3-cd]indol-6-oneTosylate, having the following chemical structure:

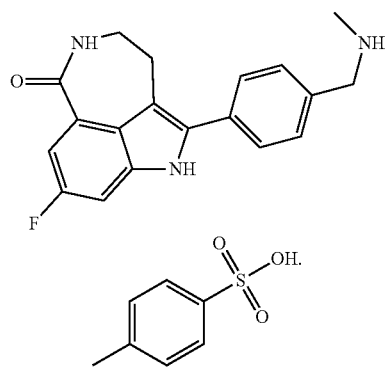

Rucaparib is an inhibitor of the mammalian poly-adenosine 5'-diphospho-ribose polymerase (PARP) enzyme, indicated as monotherapy for the treatment of patients with deleterious BRCA mutation (germline and/or somatic) associated advanced ovarian cancer who have been treated with two or more chemotherapies. It was approved by the FDA as RUBRACA (Rucaparib Camsylate).

The compound is described in U.S. Pat. No. 6,495,541. A process for its preparation is described in U.S. Pat. No. 7,323,562, as well as in *Org. Process Res. Dev.*, 2012, 16 (12), pp 1897-1904. US2004/0248879 had also described the following salts of Rucaparib: HCl, Mesylate, Phosphate, Glucuronate, Tartrate, Gluconate and Acetate. U.S. Pat. No. 7,268,126 described crystalline forms and an amorphous form of Rucaparib Phosphate. U.S. Pat. No. 8,754,072 described crystalline Camsylate and Maleate salts of Rucaparib. U.S. Pat. No. 9,045,487 described Camsylate and Maleate salts of Rucaparib.

Rucaparib is administrated in a high-load dose, of 600 mg twice daily; available tablets strength are 200 mg, 250 mg, and 300 mg.

WO 2016028689 describe tablet of Rucaparib camsylate in certain API amount. According to this application, at high drug loading, the contribution of the physical properties of the active pharmaceutical ingredient ("API") to the manufacturability of a formulation is predominant. According to the applicant, high drug loading requires compressibility properties which are contributed due to the API. In that application, it is stated that Rucaparib camsylate has advantageous properties with respect to compressibility and that it is possible to manufacture tablets thereof with a load of 45% w/w or more Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Rucaparib.

SUMMARY OF THE DISCLOSURE

The present disclosure provides solid state forms of Rucaparib and of Rucaparib salts, processes for preparation thereof, and pharmaceutical compositions thereof. These solid state forms can be used to prepare other forms of Rucaparib, Rucaparib salts and solid state forms thereof. The solid state forms of Rucaparib and of Rucaparib salts can be used to prepare other solid state forms of Rucaparib or other solid state forms of salts of Rucaparib.

The present disclosure provides solid state forms of Rucaparib and of Rucaparib salts for use in the preparation of pharmaceutical compositions and/or formulations for use in medicine, preferably for the treatment of cancer.

The present disclosure also encompasses the use of solid state forms of Rucaparib and of Rucaparib salts of the present disclosure for the preparation of pharmaceutical compositions and/or formulations.

In another aspect, the present disclosure provides pharmaceutical compositions and/or pharmaceutical formulations comprising any one or a combination of the solid state forms of Rucaparib and/or of Rucaparib salts according to the present disclosure.

In yet another embodiment, the present disclosure encompasses pharmaceutical formulations comprising any one or a combination of the described solid state forms of Rucaparib and/or of Rucaparib salts, or pharmaceutical compositions comprising them and at least one pharmaceutically acceptable excipient.

The present disclosure comprises processes for preparing the above mentioned pharmaceutical formulations. The processes comprise combining any one of or a combination of the described solid state forms of Rucaparib and/or of Rucaparib salts; or a pharmaceutical composition comprising them with at least one pharmaceutically acceptable excipient.

The solid state forms as defined herein and the pharmaceutical compositions or formulations of solid state forms of Rucaparib and or Rucaparib salts may be used as medicaments, particularly for the treatment of cancer.

The present disclosure also provides methods of treating cancer comprising administering a therapeutically effective amount of any one or a combination of the solid state forms of Rucaparib and/or of Rucaparib salts of the present disclosure, or at least one of the above pharmaceutical compositions or formulations, to a subject suffering from cancer, or otherwise in need of the treatment.

The present disclosure also provides the uses of solid state forms of Rucaparib and of Rucaparib salts of the present disclosure, or at least one of the above pharmaceutical compositions or formulations, for the manufacture of medicaments for treating cancer.

The present disclosure also provides methods of treating cancer comprising administering a therapeutically effective amount of any one or a combination of the solid state forms of Rucaparib and/or solid state forms of salts of Rucaparib of the present disclosure, or at least one of the above pharmaceutical compositions and/or formulations, to a subject in need of the treatment.

DETAILED DESCRIPTION OF THE DISCLOSURE

Figure 1:
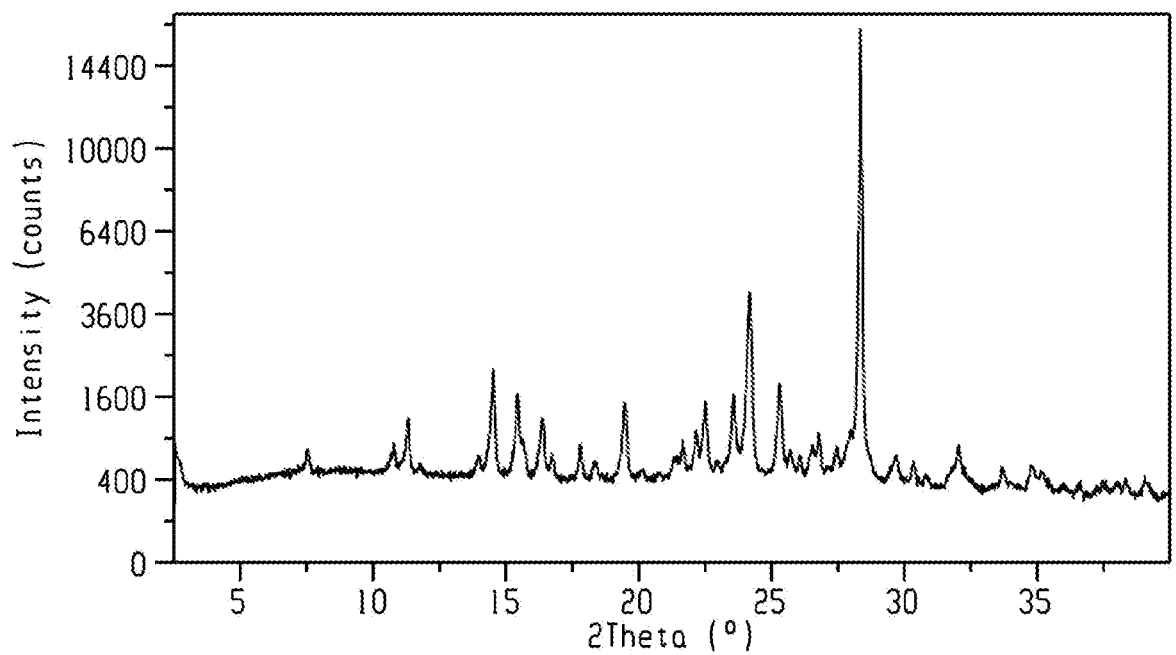
FIG. 1 shows a characteristic X-ray powder diffraction pattern (XRPD) of Rucaparib Hydrochloride Form II.

The present disclosure encompasses solid state forms of Rucaparib and of Rucaparib salts. Solid state properties of solid state forms of Rucaparib and salts thereof can be influenced by controlling the conditions under which the solid state forms of Rucaparib and of Rucaparib salts are obtained.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, solid states forms of Rucaparib and salts thereof described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Rucaparib or salt thereof. In some embodiments of the disclosure, the described solid state forms of Rucaparib or salts thereof may contain from about 1% to about 20% (w/w), from about 5% to about 20% (w/w), or from about 5% to about 10% (w/w) of one or more other solid state forms of the same Rucaparib or salt thereof.

As used herein the term "crystalline Form X1" in relation to crystalline Rucaparib base refers to crystalline Rucaparib base characterized by an XRPD pattern having peaks at 8.0, 13.1, 14.7, 16.6, 17.5, 23.8 and 28.6 degrees 2-theta±0.2 degrees 2-theta. As used herein the term "crystalline Form $X_2$" in relation to crystalline Rucaparib base refers to crystalline Rucaparib base characterized by an XRPD pattern having peaks at 7.2, 12.4, 13.9, 15.6, 16.0, 23.6, 24.9, 25.5, 26.4 and 32.6 degrees 2-theta±0.2 degrees 2-theta.

Depending on which other solid state forms a comparison is made, the crystalline forms of Rucaparib and salts thereof of the present disclosure have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Rucaparib or salt thereof referred to herein as being characterized by graphical data "as depicted in" or "as substantially depicted in" a Figure will thus be understood to include any crystal forms of Rucaparib or salt thereof characterized with the graphical data having such small variations, as are well known to the skilled person, in comparison with the Figure.

As used herein, and unless stated otherwise, the term "anhydrous" in relation to crystalline forms of Rucaparib and salts thereof, relates to a crystalline form of Rucaparib or salt thereof which does not include any crystalline water (or other solvents) in a defined, stoichiometric amount within the crystal. Moreover, an "anhydrous" form would typically not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to solid state forms of Rucaparib and salts thereof of the present disclosure corresponds to a solid state form of Rucaparib or salt thereof that is physically separated from the reaction mixture in which it is formed. The step of isolating solid state forms of Rucaparib or solid state forms of salts of Rucaparib may be performed by crystallization or precipitation.

As used herein, unless stated otherwise, the XRPD measurements are taken using copper Kα radiation wavelength 1.54184 Å. XRPD peaks reported herein are measured using CuK α radiation, λ=1.5418 Å, at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure comprises a crystalline form of Rucaparib Hydrochloride, designated Form II. The crystalline Form II of Rucaparib Hydrochloride may be characterized by data selected from one or more of the following: an X-ray powder diffraction pattern substantially as depicted in FIG. 1; an X-ray powder diffraction pattern having peaks at 11.7, 16.6, 22.4, 23.7 and 25.4 degrees 2-theta±0.2 degrees 2-theta; and combinations of these data.

Crystalline Form II of Rucaparib Hydrochloride may be further characterized by an X-ray powder diffraction pattern having peaks at 11.7, 16.6, 22.4, 23.7 and 25.4 degrees 2-theta±0.2 degrees 2-theta, and also having any one, two, three, four or five additional peaks selected from the group consisting of 7.9, 14.8, 15.7, 18.1 and 24.3 degrees 2-theta±0.2 degrees 2-theta.

Crystalline Form II of Rucaparib Hydrochloride may be characterized by each of the above characteristics alone/or by all possible combinations, e.g., an XRPD pattern having peaks at 11.7, 16.6, 22.4, 23.7 and 25.4 degrees 2-theta±0.2 degrees 2-theta; an XRPD pattern as depicted in FIG. 1, and combinations thereof.

In one embodiment of the present disclosure, crystalline Form II of Rucaparib Hydrochloride is isolated.

Figure 2:
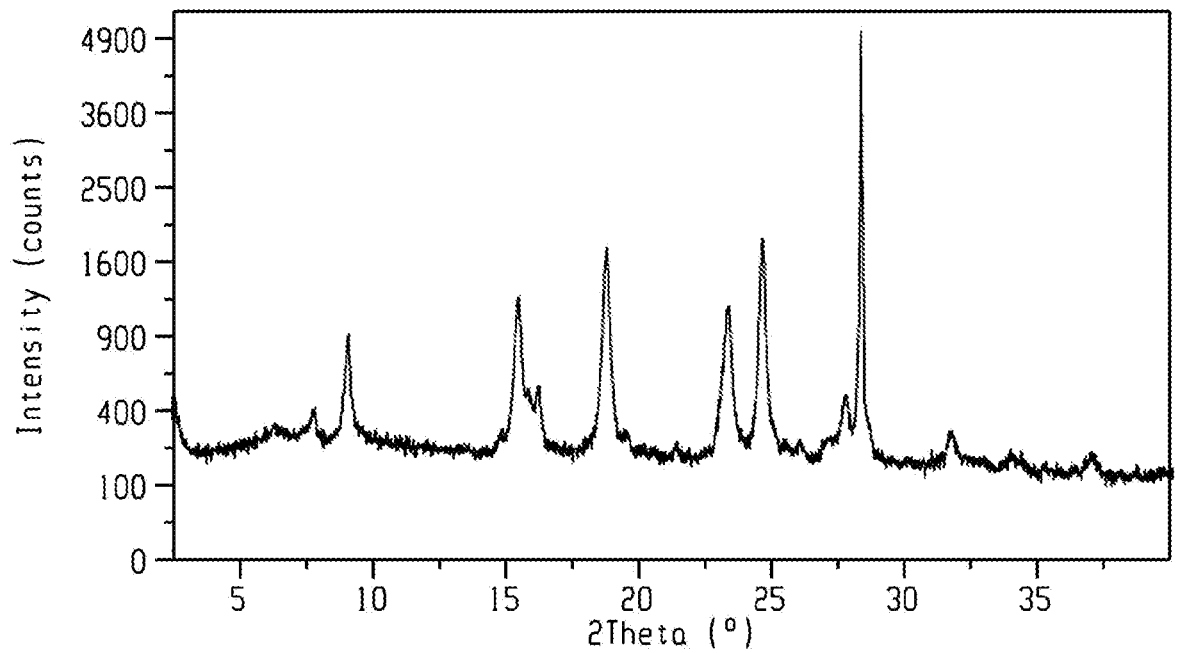
FIG. 2 shows a characteristic X-ray powder diffraction pattern of Rucaparib Hydrochloride Form III.

In another aspect, the present disclosure relates to a crystalline form of Rucaparib Hydrochloride, designated Form III. The crystalline Form III of Rucaparib Hydrochloride may be characterized by data selected from one or more of the following: an X-ray powder diffraction pattern substantially as depicted in FIG. 2; an X-ray powder diffraction pattern having peaks at 9.5, 15.8, 19.0, 23.5 and 24.8 degrees 2-theta±0.2 degrees 2-theta, and combinations of these data.

In one embodiment of the present disclosure, crystalline Form III of Rucaparib Hydrochloride is isolated.

In another aspect, the present disclosure relates to a crystalline form of Rucaparib Hydrochloride, designated Form IV. The crystalline Form IV of Rucaparib Hydrochloride may be characterized by data selected from one or more of the following: an X-ray powder diffraction pattern substantially as depicted in FIG. 3; an X-ray powder diffraction pattern having peaks at 6.7, 13.4, 14.5, 15.3 and 20.1 degrees 2-theta±0.2 degrees 2-theta, and combinations of these data.

Crystalline Form IV of Rucaparib Hydrochloride may be further characterized by an X-ray powder diffraction pattern having peaks at 6.7, 13.4, 14.5, 15.3 and 20.1 degrees 2-theta±0.2 degrees 2-theta and also having any one, two, three, four or five additional peaks selected from the group consisting of 11.5, 12.0, 21.8, 23.1 and 24.2 degrees 2-theta±0.2 degrees 2-theta.

Figure 3:
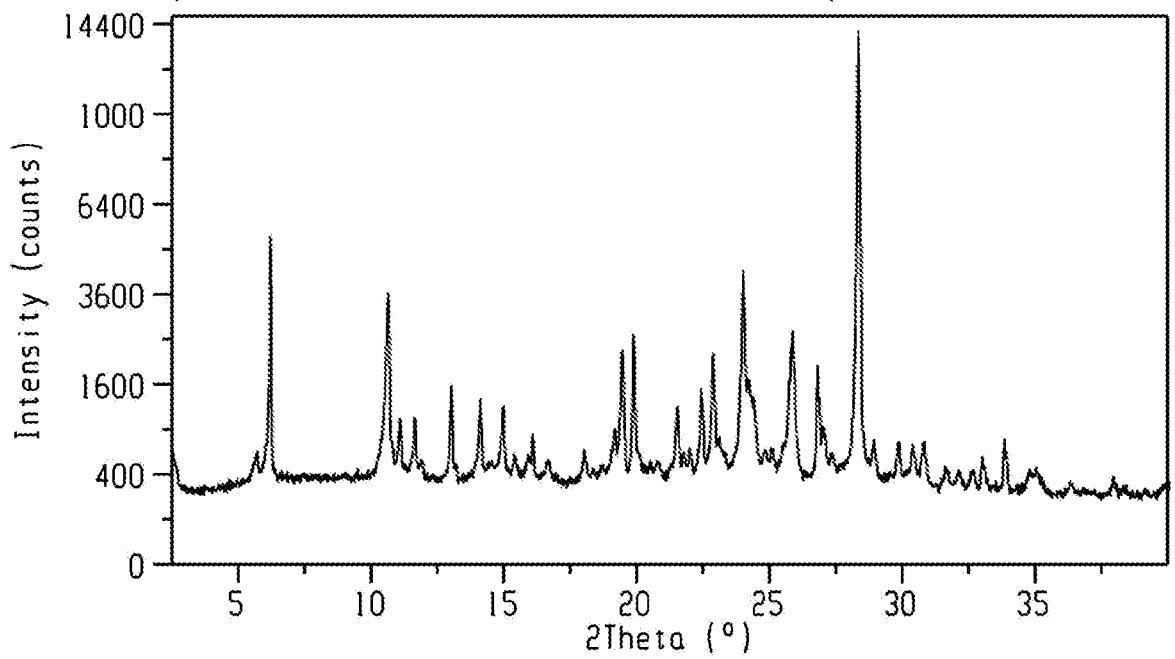
FIG. 3 shows a characteristic X-ray powder diffraction pattern of Rucaparib Hydrochloride Form IV.

Crystalline Form IV of Rucaparib Hydrochloride may be characterized by each of the above characteristics alone/or by all possible combinations, e.g., an XRPD pattern having peaks at 6.7, 13.4, 14.5, 15.3 and 20.1 degrees 2-theta±0.2 degrees 2-theta; an XRPD pattern as depicted in FIG. 3, and combinations thereof.

In one embodiment of the present disclosure, crystalline Form IV of Rucaparib Hydrochloride is isolated.

In another aspect, the present disclosure relates to a crystalline form of Rucaparib Acetate, designated Form I. The crystalline Form I of Rucaparib Acetate may be characterized by data selected from one or more of the following: an X-ray powder diffraction pattern substantially as depicted in FIG. 4; an X-ray powder diffraction pattern having peaks at 6.1, 11.2, 14.1, 15.9 and 16.1 degrees 2-theta±0.2 degrees 2-theta, and combinations of these data.

Crystalline Form I of Rucaparib Acetate may be further characterized by an X-ray powder diffraction pattern having peaks at 6.1, 11.2, 14.1, 15.9 and 16.1 degrees 2-theta±0.2 degrees 2-theta and also having any one, two, three, four or five additional peaks selected from the group consisting of 13.0, 14.7, 21.9, 23.3 and 24.5 degrees 2-theta±0.2 degrees 2-theta.

Figure 4:
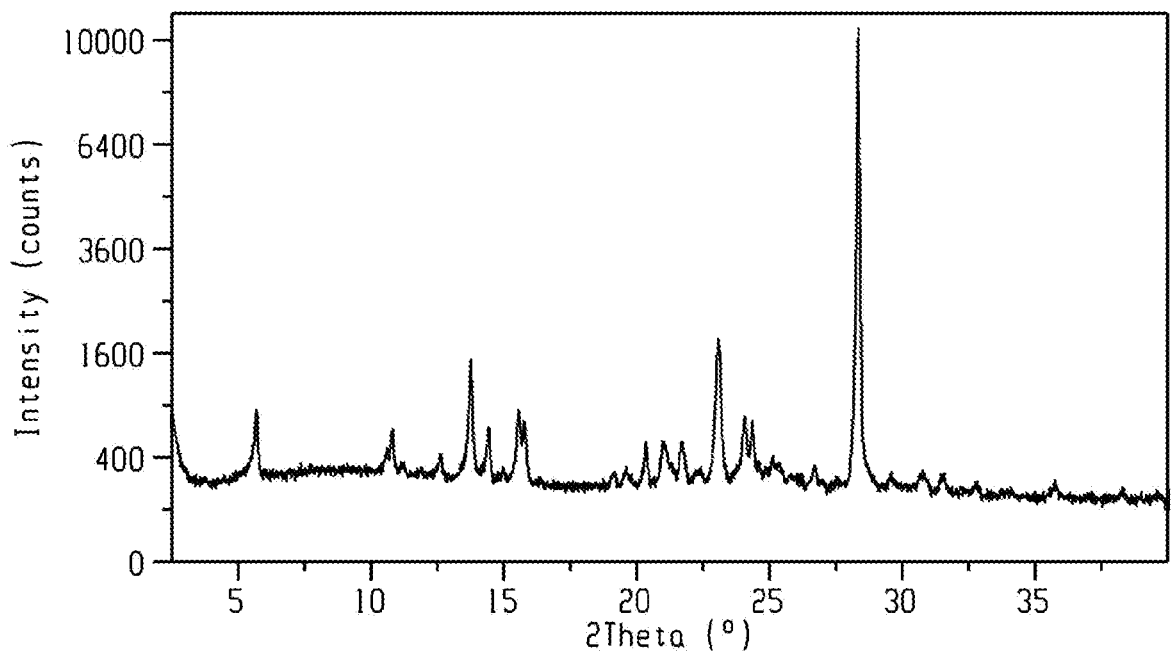
FIG. 4 shows a characteristic X-ray powder diffraction pattern of a mixture of Rucaparib Acetate Form I.

Crystalline Form I of Rucaparib Acetate may be characterized by each of the above characteristics alone/or by all possible combinations, e.g., an XRPD pattern having peaks at 6.1, 11.2, 14.1, 15.9 and 16.1 degrees 2-theta±0.2 degrees 2-theta; an XRPD pattern as depicted in FIG. 4, and combinations thereof.

In one embodiment of the present disclosure, crystalline Form I of Rucaparib Acetate is isolated.

In another aspect, the present disclosure relates to a crystalline form of Rucaparib Acetate, designated Form II. The crystalline Form II of Rucaparib Acetate may be characterized by data selected from one or more of the following: an X-ray powder diffraction pattern substantially as depicted in FIG. 5; an X-ray powder diffraction pattern having peaks at 10.8, 12.1, 12.6, 16.8 and 19.0 degrees 2-theta±0.2 degrees 2-theta, and combinations of these data.

Crystalline Form II of Rucaparib Acetate may be further characterized by an X-ray powder diffraction pattern having peaks at 10.8, 12.1, 12.6, 16.8 and 19.0 degrees 2-theta±0.2 degrees 2-theta and also having any one, two or three, four or five additional peaks selected from the group consisting of 9.6, 13.4, 18.5, 23.0 and 24.2 degrees 2-theta±0.2 degrees 2-theta.

Figure 5:
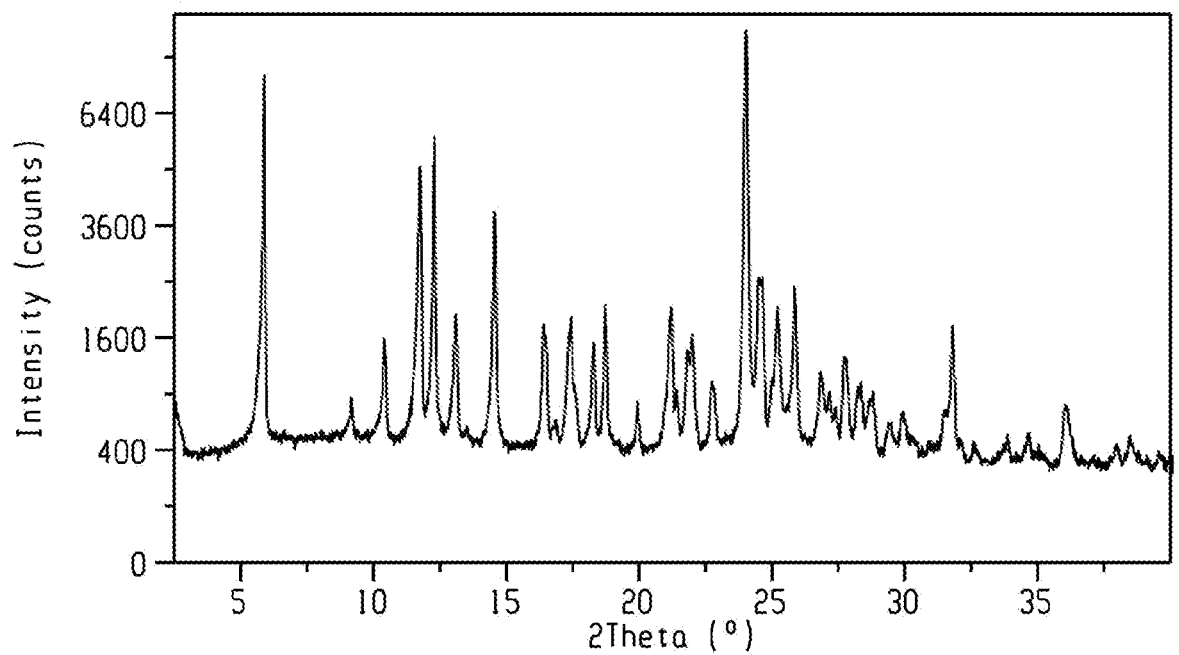
FIG. 5 shows a characteristic X-ray powder diffraction pattern of Rucaparib Acetate Form II.

Crystalline Form II of Rucaparib Acetate may be characterized by each of the above characteristics alone/or by all possible combinations, e.g., an XRPD pattern having peaks at 10.8, 12.1, 12.6, 16.8 and 19.0 degrees 2-theta±0.2 degrees 2-theta; an XRPD pattern as depicted in FIG. 5, and combinations thereof.

In one embodiment of the present disclosure, crystalline Form II of Rucaparib Acetate is isolated.

In another aspect, the present disclosure relates to a crystalline form of Rucaparib Acetate, designated Form III. The crystalline Form III of Rucaparib Acetate may be characterized by data selected from one or more of the following: an X-ray powder diffraction pattern substantially as depicted in FIG. 6; an X-ray powder diffraction pattern having peaks at 7.8, 8.6, 13.6, 15.7 and 16.4 degrees 2-theta±0.2 degrees 2-theta, and combinations of these data.

Crystalline Form III of Rucaparib Acetate may be further characterized by an X-ray powder diffraction pattern having peaks at 7.8, 8.6, 13.6, 15.7 and 16.4 degrees 2-theta±0.2 degrees 2-theta and also having any one, two, three, four or five additional peaks selected from the group consisting of 13.9, 17.1, 18.7, 22.5 and 23.4 degrees 2-theta±0.2 degrees 2-theta.

Figure 6:
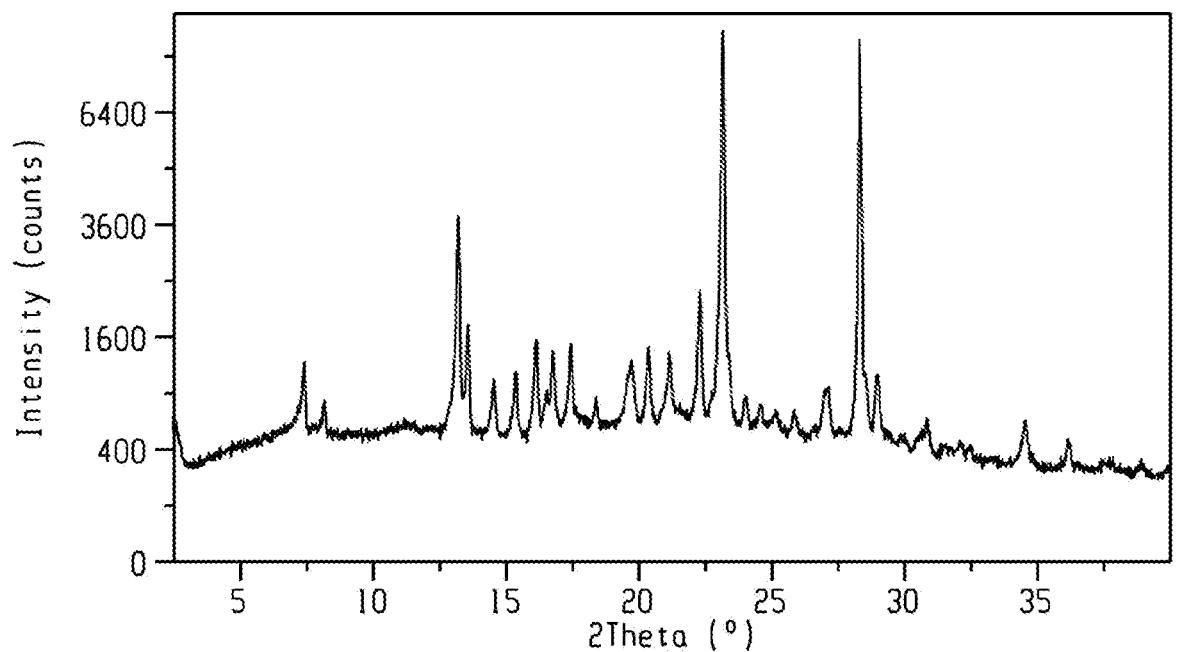
FIG. 6 shows a characteristic X-ray powder diffraction pattern of Rucaparib Acetate Form III.

Crystalline Form III of Rucaparib Acetate may be characterized by each of the above characteristics alone/or by all possible combinations, e.g., an XRPD pattern having peaks at 7.8, 8.6, 13.6, 15.7 and 16.4 degrees 2-theta±0.2 degrees 2-theta; an XRPD pattern as depicted in FIG. 6, and combinations thereof.

In one embodiment of the present disclosure, crystalline Form III of Rucaparib Acetate is isolated.

In another aspect, the present disclosure relates to a crystalline form of Rucaparib Acetate, designated Form IV. The crystalline Form IV of Rucaparib Acetate may be characterized by data selected from one or more of the following: an X-ray powder diffraction pattern substantially as depicted in FIG. 7; an X-ray powder diffraction pattern having peaks at 10.1, 15.1, 15.5, 22.2 and 23.6 degrees 2-theta±0.2 degrees 2-theta, and combinations of these data.

Crystalline Form IV of Rucaparib Acetate may be further characterized by an X-ray powder diffraction pattern having peaks at 10.1, 15.1, 15.5, 22.2 and 23.6 degrees 2-theta±0.2 degrees 2-theta and also having any one, two, three, four or five additional peaks selected from the group consisting of 9.8, 11.0, 14.1, 19.4 and 21.3 degrees 2-theta±0.2 degrees 2-theta.

Figure 7:
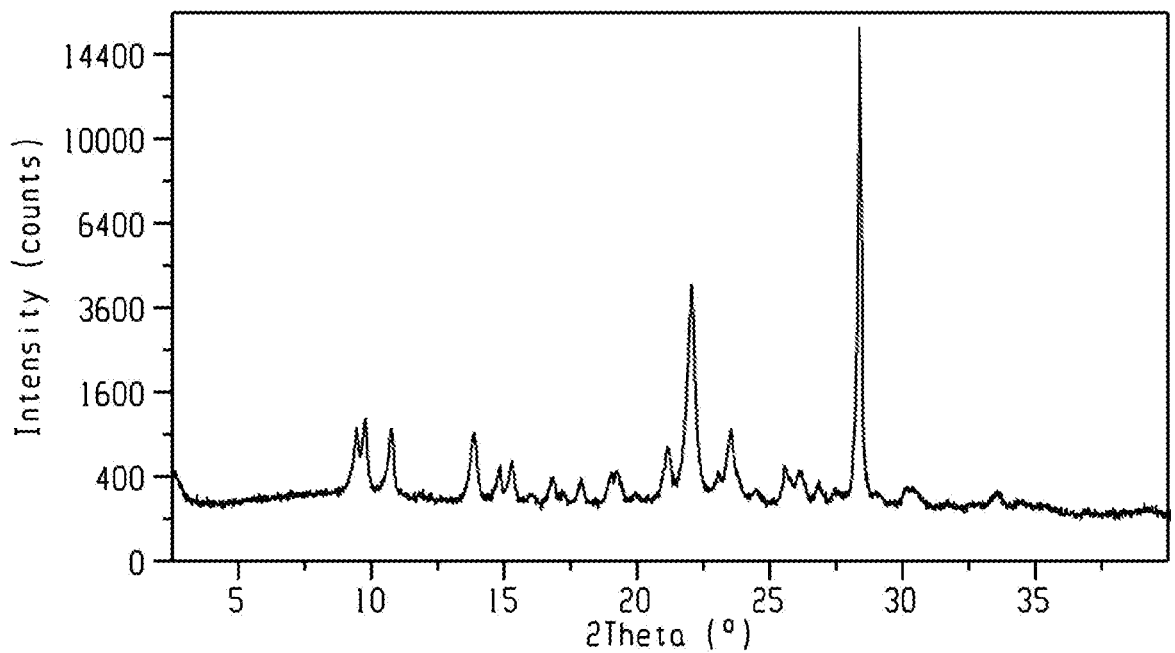
FIG. 7 shows a characteristic X-ray powder diffraction pattern of Rucaparib Acetate Form IV.

Crystalline Form IV of Rucaparib Acetate may be characterized by each of the above characteristics alone/or by all possible combinations, e.g., an XRPD pattern having peaks at 10.1, 15.1, 15.5, 22.2 and 23.6 degrees 2-theta±0.2 degrees 2-theta; an XRPD pattern as depicted in FIG. 7, and combinations thereof.

In one embodiment of the present disclosure, crystalline Form IV of Rucaparib Acetate is isolated.

In another aspect, the present disclosure relates to a crystalline form of Rucaparib Hydrobromide, designated Form I. The crystalline Form I of Rucaparib Hydrobromide may be characterized by data selected from one or more of the following: an X-ray powder diffraction pattern substantially as depicted in FIG. 8; an X-ray powder diffraction pattern having peaks at 6.0, 11.0, 12.1, 20.8 and 24.9 degrees 2-theta±0.2 degrees 2-theta, and combinations of these data.

Crystalline Form I of Rucaparib Hydrobromide may be further characterized by an X-ray powder diffraction pattern having peaks at 6.0, 11.0, 12.1, 20.8 and 24.9 degrees 2-theta±0.2 degrees 2-theta and also having any one, two, three, four or five additional peaks selected from the group consisting of 15.2, 15.4, 16.5, 18.1 and 26.5 degrees 2-theta±0.2 degrees 2-theta.

Figure 8:
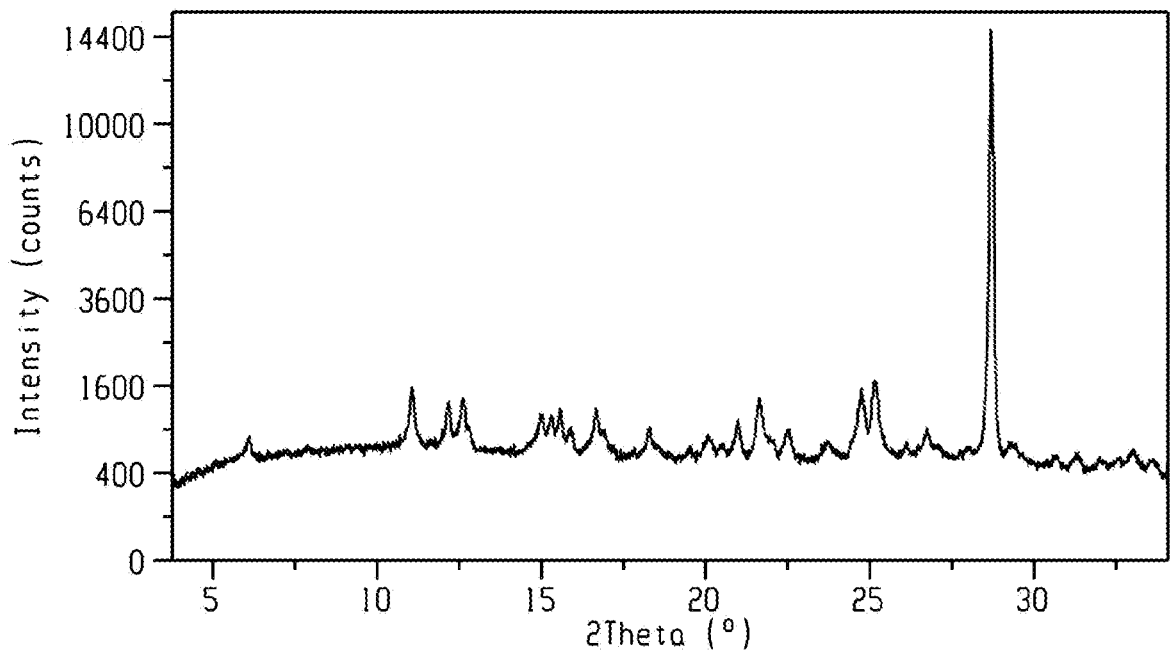
FIG. 8 shows a characteristic X-ray powder diffraction pattern of Rucaparib Hydrobromide Form I.

Crystalline Form I of Rucaparib Hydrobromide may be characterized by each of the above characteristics alone/or by all possible combinations, e.g., an XRPD pattern having peaks at 6.0, 11.0, 12.1, 20.8 and 24.9 degrees 2-theta±0.2 degrees 2-theta; an XRPD pattern as depicted in FIG. 8, and combinations thereof.

In one embodiment of the present disclosure, crystalline Form I of Rucaparib Hydrobromide is isolated.

In another aspect, the present disclosure relates to a crystalline form of Rucaparib Hydrobromide, designated Form II. The crystalline Form II of Rucaparib Hydrobromide may be characterized by data selected from one or more of the following: an X-ray powder diffraction pattern substantially as depicted in FIG. 9; an X-ray powder diffraction pattern having peaks at 14.9, 19.9, 21.6, 22.4 and 23.4 degrees 2-theta±0.2 degrees 2-theta, and combinations of these data.

Crystalline Form II of Rucaparib Hydrobromide may be further characterized by an X-ray powder diffraction pattern having peaks at 14.9, 19.9, 21.6, 22.4 and 23.4 degrees 2-theta±0.2 degrees 2-theta and also having any one, two, three, or four additional peaks selected from the group consisting of 15.8, 16.8, 18.4 and 24.6 degrees 2-theta±0.2 degrees 2-theta.

Figure 9:
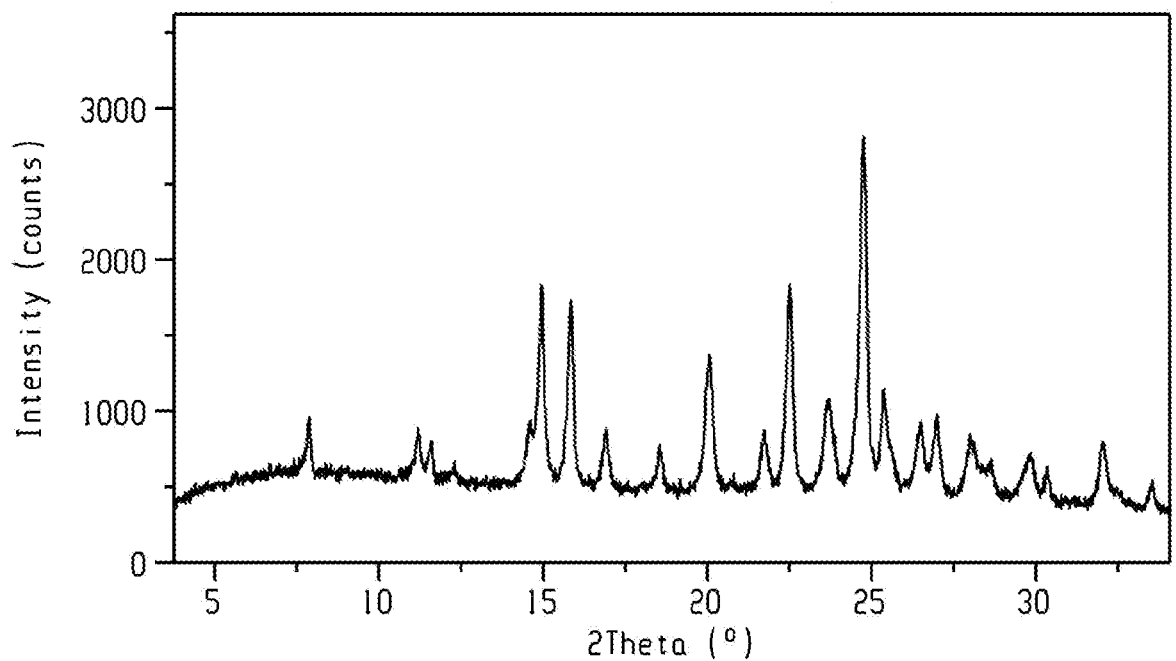
FIG. 9 shows a characteristic X-ray powder diffraction pattern of Rucaparib Hydrobromide Form II.

Crystalline Form II of Rucaparib Hydrobromide may be characterized by each of the above characteristics alone/or by all possible combinations, e.g., an XRPD pattern having peaks at 14.9, 19.9, 21.6, 22.4 and 23.4 degrees 2-theta±0.2 degrees 2-theta; an XRPD pattern as depicted in FIG. 9, and combinations thereof. In one embodiment of the present disclosure, crystalline Form II of Rucaparib Hydrobromide is isolated.

In another aspect, the present disclosure relates to a crystalline form of Rucaparib Hydrobromide, designated Form III. The crystalline Form III of Rucaparib Hydrobromide may be characterized by data selected from one or more of the following: an X-ray powder diffraction pattern substantially as depicted in FIG. 10; an X-ray powder diffraction pattern having peaks at 13.5, 20.6, 21.3, 21.6 and 25.7 degrees 2-theta±0.2 degrees 2-theta, and combinations of these data.

Crystalline Form III of Rucaparib Hydrobromide may be further characterized by an X-ray powder diffraction pattern having peaks at 13.5, 20.6, 21.3, 21.6 and 25.7 degrees 2-theta±0.2 degrees 2-theta and also having any one, two, three, four or five additional peaks selected from the group consisting of 12.5, 14.5, 15.6, 17.5 and 17.9 degrees 2-theta±0.2 degrees 2-theta.

Figure 10:
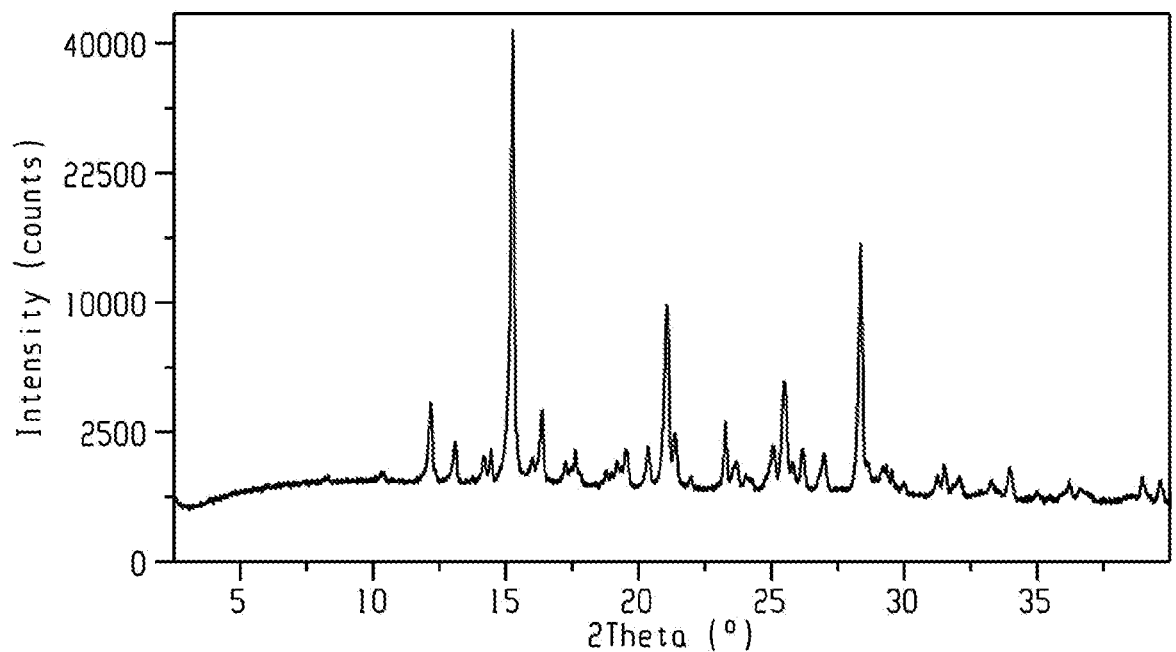
FIG. 10 shows a characteristic X-ray powder diffraction pattern of Rucaparib Hydrobromide Form III.

Crystalline Form III of Rucaparib Hydrobromide may be characterized by each of the above characteristics alone/or by all possible combinations, e.g., an XRPD pattern having peaks at 13.5, 20.6, 21.3, 21.6 and 25.7 degrees 2-theta±0.2 degrees 2-theta; an XRPD pattern as depicted in FIG. 10, and combinations thereof.

In one embodiment of the present disclosure, crystalline Form III of Rucaparib Hydrobromide is isolated.

In another aspect, the present disclosure relates to a crystalline form of Rucaparib Hydrobromide, designated Form IV. The crystalline Form IV of Rucaparib Hydrobromide may be characterized by an X-ray powder diffraction pattern having peaks at 7.2, 16.4, 20.9, 21.9 and 22.7 degrees 2-theta±0.2 degrees 2-theta.

Crystalline Form IV of Rucaparib Hydrobromide may be further characterized by an X-ray powder diffraction pattern having peaks at 7.2, 16.4, 20.9, 21.9 and 22.7 degrees 2-theta±0.2 degrees 2-theta and also having any one, two, three, four or five additional peaks selected from the group consisting of 12.4, 14.4, 16.7, 17.7 and 21.5 degrees 2-theta±0.2 degrees 2-theta.

In another aspect, the present disclosure relates to a crystalline form of Rucaparib Citrate, designated Form I. The crystalline Form I of Rucaparib Citrate may be characterized by data selected from one or more of the following: an X-ray powder diffraction pattern substantially as depicted in FIG. 12; an X-ray powder diffraction pattern having peaks at 4.7, 13.3, 18.8, 19.8 and 21.0 degrees 2-theta±0.2 degrees 2-theta, and combinations of these data.

Crystalline Form I of Rucaparib Citrate may be further characterized by an X-ray powder diffraction pattern having peaks at 4.7, 13.3, 18.8, 19.8 and 21.0 degrees 2-theta±0.2 degrees 2-theta and also having any one, two, three, four or five additional peaks selected from the group consisting of 11.4, 14.1, 16.9, 18.4 and 24.6 degrees 2-theta±0.2 degrees 2-theta.

Figure 12:
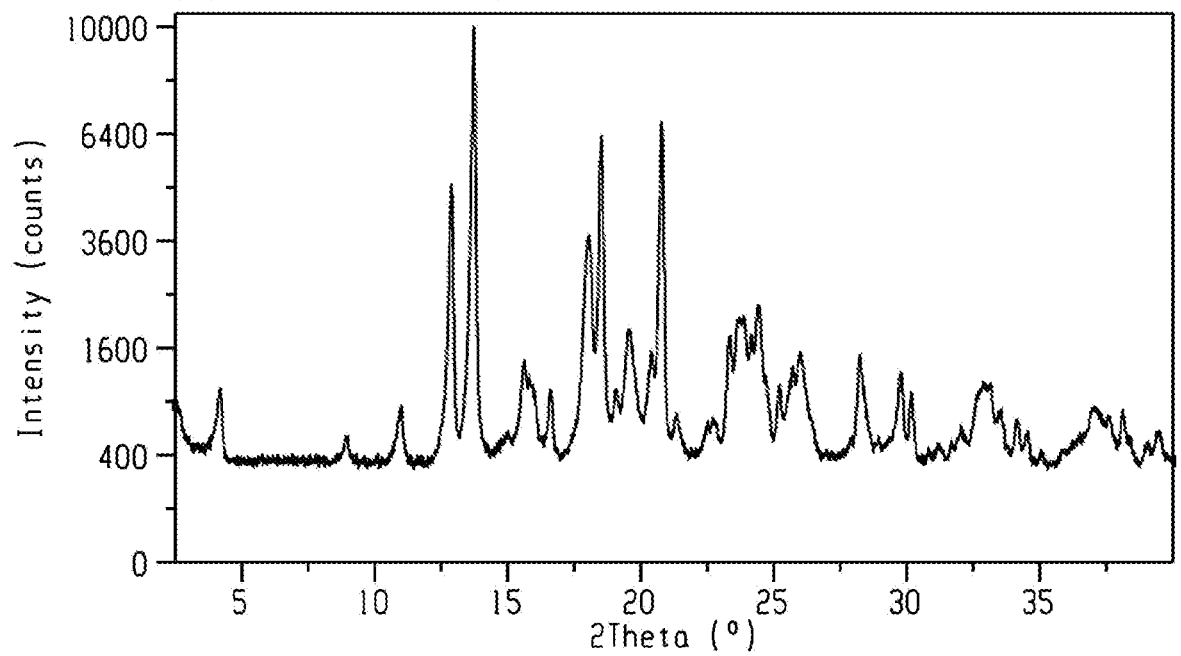
FIG. 12 shows a characteristic X-ray powder diffraction pattern of Rucaparib Citrate Form I.

Crystalline Form I of Rucaparib Citrate may be characterized by each of the above characteristics alone/or by all possible combinations, e.g., an XRPD pattern having peaks at 4.7, 13.3, 18.8, 19.8 and 21.0 degrees 2-theta±0.2 degrees 2-theta; an XRPD pattern as depicted in FIG. 12, and combinations thereof.

In one embodiment of the present disclosure, crystalline Form I of Rucaparib Citrate is isolated.

In another aspect, the present disclosure relates to a crystalline form of Rucaparib Citrate, designated Form II. The crystalline Form II of Rucaparib Citrate may be characterized by data selected from one or more of the following: an X-ray powder diffraction pattern substantially as depicted in FIG. 13; an X-ray powder diffraction pattern having peaks at 12.1, 18.0, 18.4, 21.4 and 23.4 degrees 2-theta±0.2 degrees 2-theta, and combinations of these data.

Crystalline Form II of Rucaparib Citrate may be further characterized by an X-ray powder diffraction pattern having peaks at 12.1, 18.0, 18.4, 21.4 and 23.4 degrees 2-theta±0.2 degrees 2-theta and also having any one, two, three, four or five additional peaks selected from the group consisting of 10.6, 14.1, 16.0, 20.0 and 23.7 degrees 2-theta±0.2 degrees 2-theta.

Figure 13:
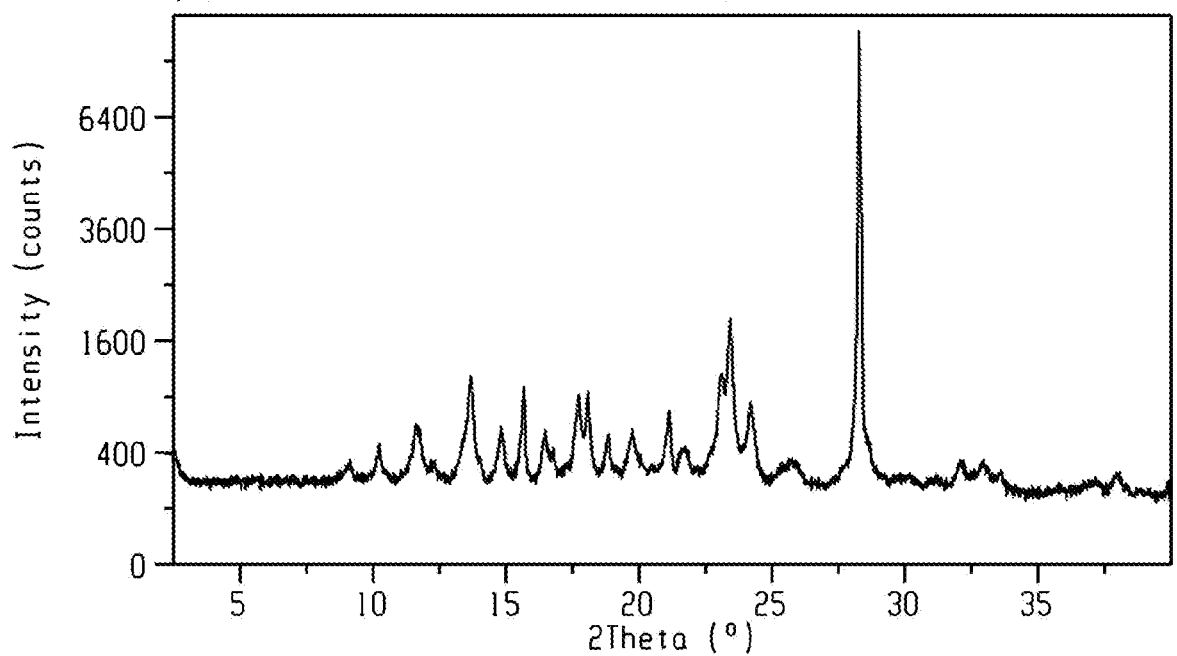
FIG. 13 shows a characteristic X-ray powder diffraction pattern of Rucaparib Citrate Form II.

Crystalline Form II of Rucaparib Citrate may be characterized by each of the above characteristics alone/or by all possible combinations, e.g., an XRPD pattern having peaks at 12.1, 18.0, 18.4, 21.4 and 23.4 degrees 2-theta±0.2 degrees 2-theta; an XRPD pattern as depicted in FIG. 13, and combinations thereof.

In one embodiment of the present disclosure, crystalline Form II of Rucaparib Citrate is isolated.

In another aspect, the present disclosure relates to a crystalline form of Rucaparib D-(−)-Tartrate, designated Form I. The crystalline Form I of Rucaparib D-(−)-Tartrate may be characterized by data selected from one or more of the following: an X-ray powder diffraction pattern substantially as depicted in FIG. 14; an X-ray powder diffraction pattern having peaks at 5.1, 10.1, 11.9, 13.7 and 20.1 degrees 2-theta±0.2 degrees 2-theta, and combinations of these data.

Crystalline Form I of Rucaparib D-(−)-Tartrate may be further characterized by an X-ray powder diffraction pattern having peaks at 5.1, 10.1, 11.9, 13.7 and 20.1 degrees 2-theta±0.2 degrees 2-theta and also having any one, two, three, four or five additional peaks selected from the group consisting of 17.2, 17.8, 19.5, 21.5 and 25.2 degrees 2-theta±0.2 degrees 2-theta.

Figure 14:
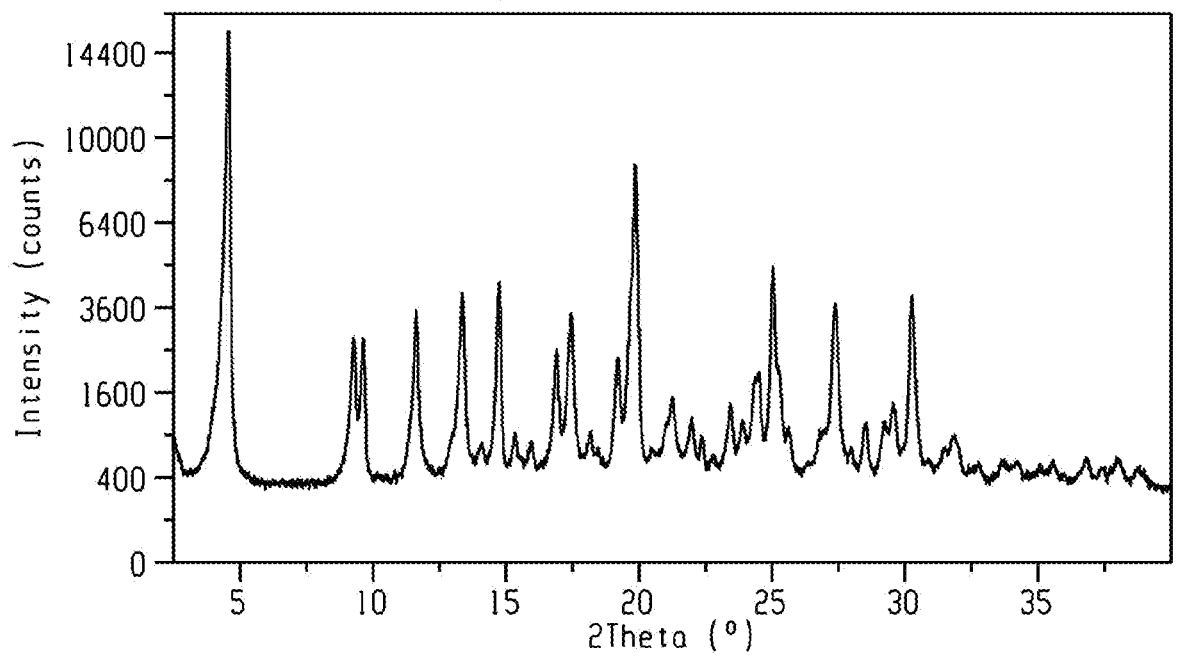
FIG. 14 shows a characteristic X-ray powder diffraction pattern of Rucaparib D-(−)-Tartrate Form I.

Crystalline Form I of Rucaparib D-(−)-Tartrate may be characterized by each of the above characteristics alone/or by all possible combinations, e.g., an XRPD pattern having peaks at 5.1, 10.1, 11.9, 13.7 and 20.1 degrees 2-theta±0.2 degrees 2-theta; an XRPD pattern as depicted in FIG. 14, and combinations thereof.

In one embodiment of the present disclosure, crystalline Form I of Rucaparib D-(−)-Tartrate is isolated.

In another aspect, the present disclosure relates to a crystalline form of Rucaparib D-(−)-Tartrate, designated Form II. The crystalline Form II of Rucaparib D-(−)-Tartrate may be characterized by data selected from one or more of the following: an X-ray powder diffraction pattern substantially as depicted in FIG. 15; an X-ray powder diffraction pattern having peaks at 9.6, 12.8, 16.1, 19.1 and 23.6 degrees 2-theta±0.2 degrees 2-theta, and combinations of these data.

Crystalline Form II of Rucaparib D-(−)-Tartrate may be further characterized by an X-ray powder diffraction pattern having peaks at 9.6, 12.8, 16.1, 19.1 and 23.6 degrees 2-theta±0.2 degrees 2-theta and also having any one, two, three, four or five additional peaks selected from the group consisting of 15.1, 17.4, 18.1, 20.4 and 23.0 degrees 2-theta±0.2 degrees 2-theta.

Figure 15:
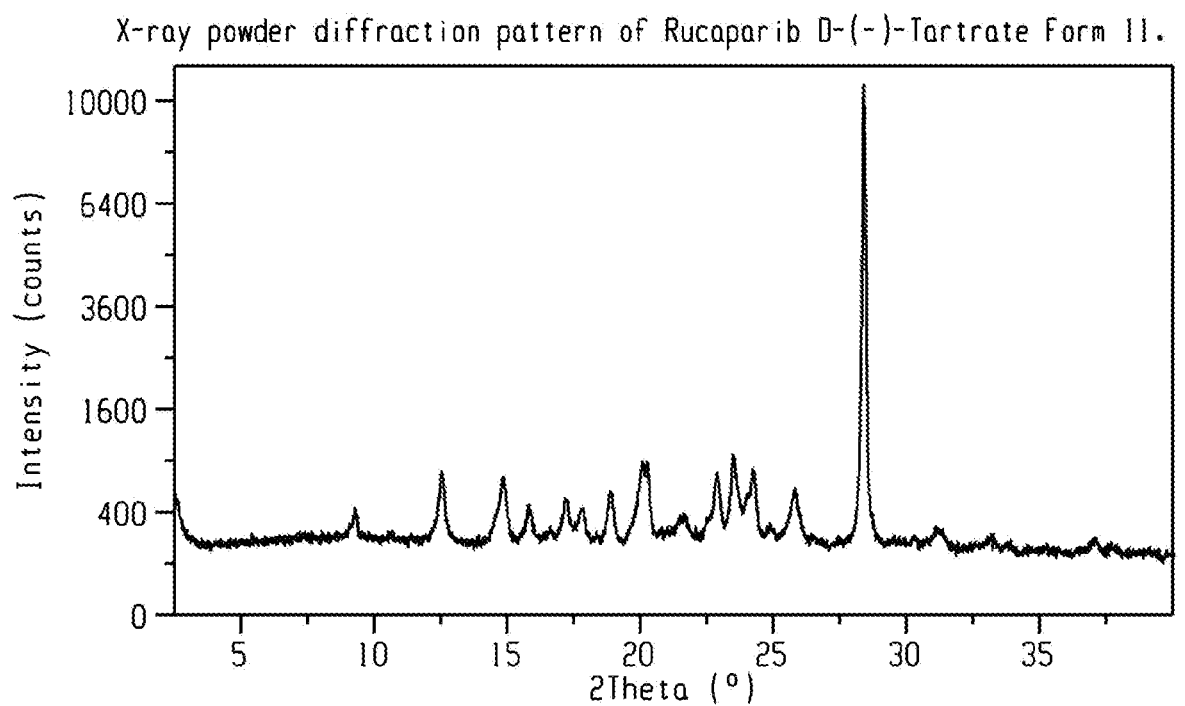
FIG. 15 shows a characteristic X-ray powder diffraction pattern of Rucaparib D-(−)-Tartrate Form II.

Crystalline Form II of Rucaparib D-(−)-Tartrate may be characterized by each of the above characteristics alone/or by all possible combinations, e.g., an XRPD pattern having peaks at 9.6, 12.8, 16.1, 19.1 and 23.6 degrees 2-theta±0.2 degrees 2-theta; an XRPD pattern as depicted in FIG. 15, and combinations thereof.

In one embodiment of the present disclosure, crystalline Form II of Rucaparib D-(−)-Tartrate is isolated.

In another aspect, the present disclosure relates to a crystalline form of Rucaparib L-(+)-Tartrate, designated Form I. The crystalline Form I of Rucaparib L-(+)-Tartrate may be characterized by data selected from one or more of the following: an X-ray powder diffraction pattern substantially as depicted in FIG. 27; an X-ray powder diffraction pattern having peaks at 5.1, 10.1, 11.9, 13.7 and 20.1 degrees 2-theta±0.2 degrees 2-theta, and combinations of these data.

Crystalline Form I of Rucaparib L-(+)-Tartrate may be further characterized by an X-ray powder diffraction pattern having peaks at 5.1, 10.1, 11.9, 13.7 and 20.1 degrees 2-theta±0.2 degrees 2-theta and also having any one, two, three, four or five additional peaks selected from the group consisting of 17.2, 17.8, 19.5, 21.5 and 25.2 degrees 2-theta±0.2 degrees 2-theta.

Figure 27:
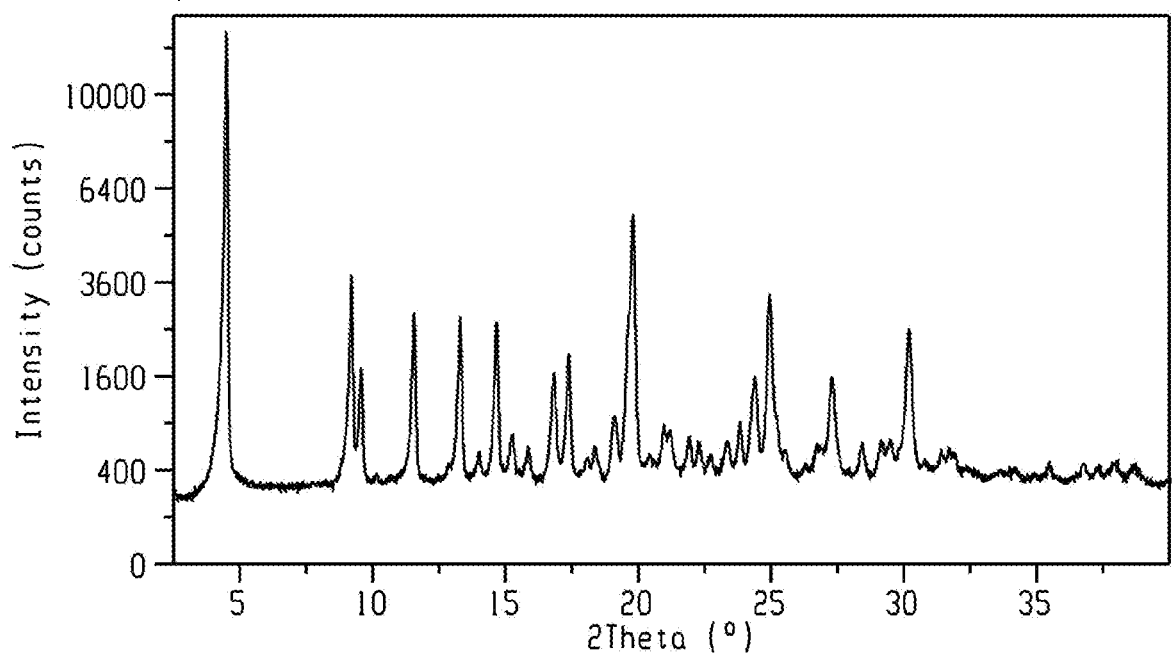
FIG. 27 shows a characteristic X-ray powder diffraction pattern of Rucaparib L-(+)-Tartrate Form I.

Crystalline Form I of Rucaparib L-(+)-Tartrate may be characterized by each of the above characteristics alone/or by all possible combinations, e.g., an XRPD pattern having peaks at 5.1, 10.1, 11.9, 13.7 and 20.1 degrees 2-theta±0.2 degrees 2-theta; an XRPD pattern as depicted in FIG. 27, and combinations thereof.

In one embodiment of the present disclosure, crystalline Form I of Rucaparib L-(+)-Tartrate is isolated.

In another aspect, the present disclosure relates to a crystalline form of Rucaparib L-(+)-Tartrate, designated Form II. The crystalline Form II of Rucaparib L-(+)-Tartrate may be characterized by data selected from one or more of the following: an X-ray powder diffraction pattern substantially as depicted in FIG. 28; an X-ray powder diffraction pattern having peaks at 9.6, 12.8, 16.1, 19.1 and 23.6 degrees 2-theta±0.2 degrees 2-theta, and combinations of these data.

Crystalline Form II of Rucaparib L-(+)-Tartrate may be further characterized by an X-ray powder diffraction pattern having peaks at 9.6, 12.8, 16.1, 19.1 and 23.6 degrees 2-theta±0.2 degrees 2-theta and also having any one, two, three, four or five additional peaks selected from the group consisting of 15.1, 17.4, 18.1, 20.4 and 23.0 degrees 2-theta±0.2 degrees 2-theta.

Figure 28:
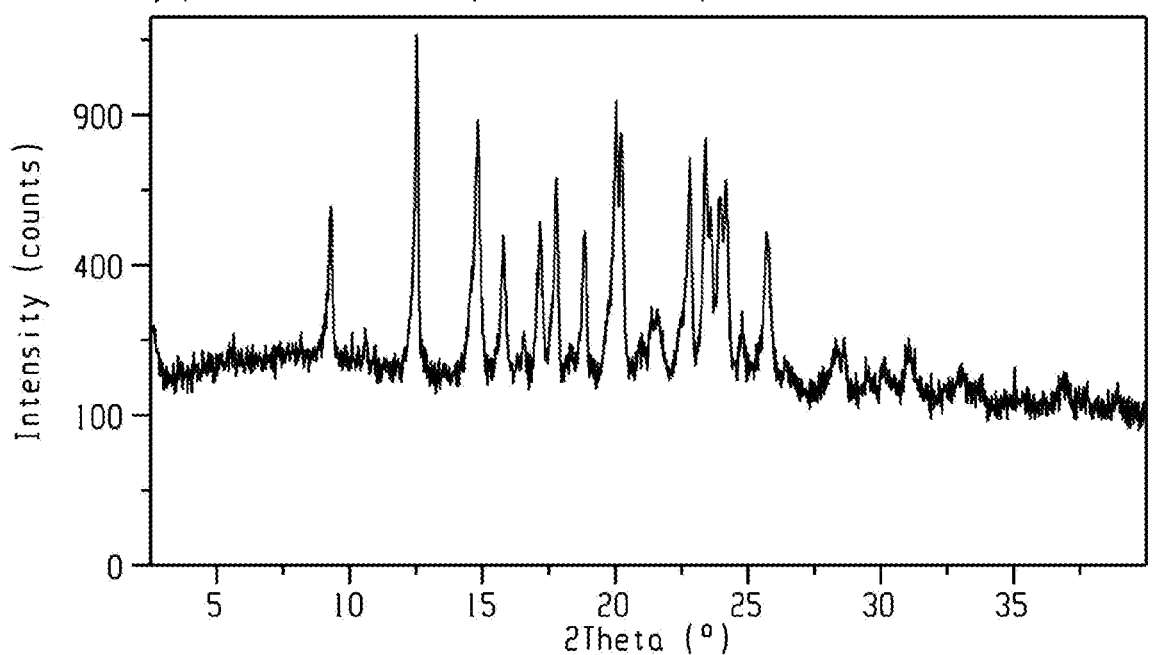
FIG. 28 shows a characteristic X-ray powder diffraction pattern of Rucaparib L-(+)-Tartrate Form II.

Crystalline Form II of Rucaparib L-(+)-Tartrate may be characterized by each of the above characteristics alone/or by all possible combinations, e.g., an XRPD pattern having peaks at 9.6, 12.8, 16.1, 19.1 and 23.6 degrees 2-theta±0.2 degrees 2-theta; an XRPD pattern as depicted in FIG. 28, and combinations thereof.

In one embodiment of the present disclosure, crystalline Form II of Rucaparib L-(+)-Tartrate is isolated.

In another aspect, the present disclosure relates to a crystalline form of Rucaparib Hemi-Edisylate, designated Form I. The crystalline Form I of Rucaparib Hemi-Edisylate may be characterized by data selected from one or more of the following: an X-ray powder diffraction pattern substantially as depicted in FIG. 16; an X-ray powder diffraction pattern having peaks at 12.2, 13.7, 16.4, 18.1 and 18.6 degrees 2-theta±0.2 degrees 2-theta, and combinations of these data.

Crystalline Form I of Rucaparib Hemi-Edisylate may be further characterized by an X-ray powder diffraction pattern having peaks at 12.2, 13.7, 16.4, 18.1 and 18.6 degrees 2-theta±0.2 degrees 2-theta and also having any one, two, three, four or five additional peaks selected from the group consisting of 10.0, 12.7, 15.2, 19.1 and 19.4 degrees 2-theta±0.2 degrees 2-theta.

Figure 16:
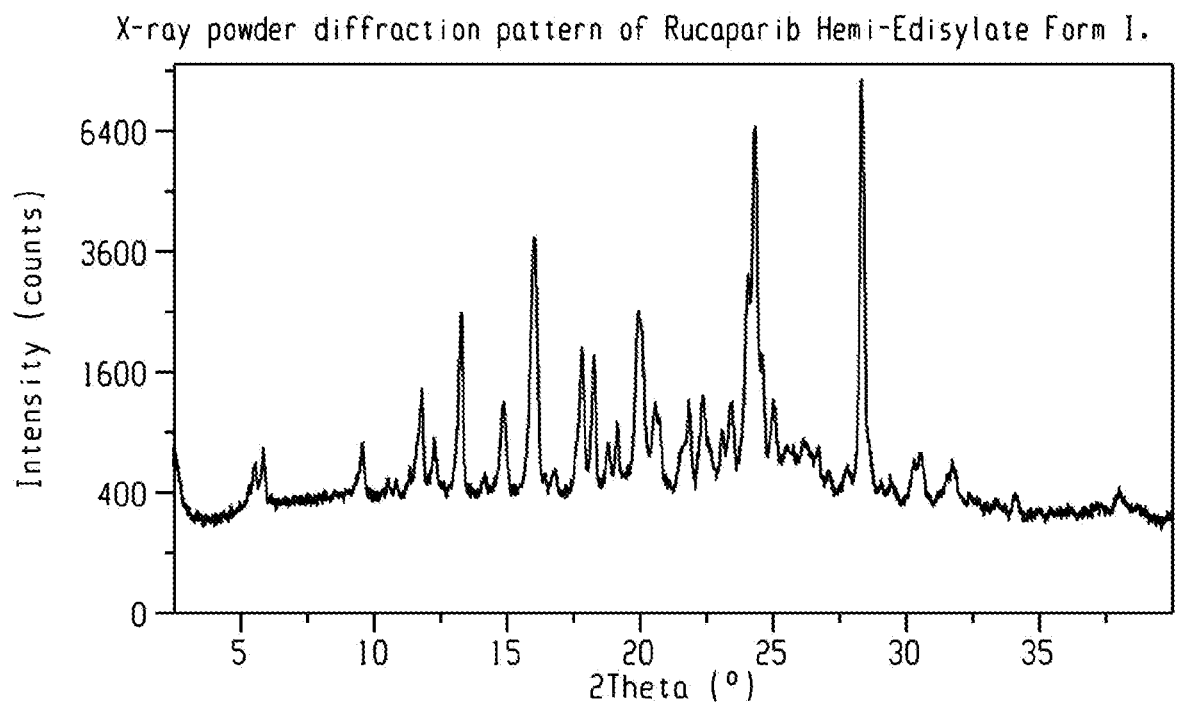
FIG. 16 shows a characteristic X-ray powder diffraction pattern of Rucaparib Hemi-Edisylate Form I.

Crystalline Form I of Rucaparib Hemi-Edisylate may be characterized by each of the above characteristics alone/or by all possible combinations, e.g., an XRPD pattern having peaks at 12.2, 13.7, 16.4, 18.1 and 18.6 degrees 2-theta±0.2 degrees 2-theta; an XRPD pattern as depicted in FIG. 16, and combinations thereof.

In one embodiment of the present disclosure, crystalline Form I of Rucaparib Hemi-Edisylate is isolated.

In another aspect, the present disclosure relates to a crystalline form of Rucaparib Hemi-Edisylate, designated Form III. The crystalline Form III of Rucaparib Hemi-Edisylate may be characterized by data selected from one or more of the following: an X-ray powder diffraction pattern substantially as depicted in FIG. 25; an X-ray powder diffraction pattern having peaks at 7.1, 17.2, 21.3, 21.8 and 23.5 degrees 2-theta±0.2 degrees 2-theta, and combinations of these data.

Crystalline Form III of Rucaparib Hemi-Edisylate may be further characterized by an X-ray powder diffraction pattern having peaks at 7.1, 17.2, 21.3, 21.8 and 23.5 degrees 2-theta±0.2 degrees 2-theta and also having any one, two, three, four or five additional peaks selected from the group consisting of 11.2, 11.4, 15.7, 21.6 and 25.4 degrees 2-theta±0.2 degrees 2-theta.

Figure 25:
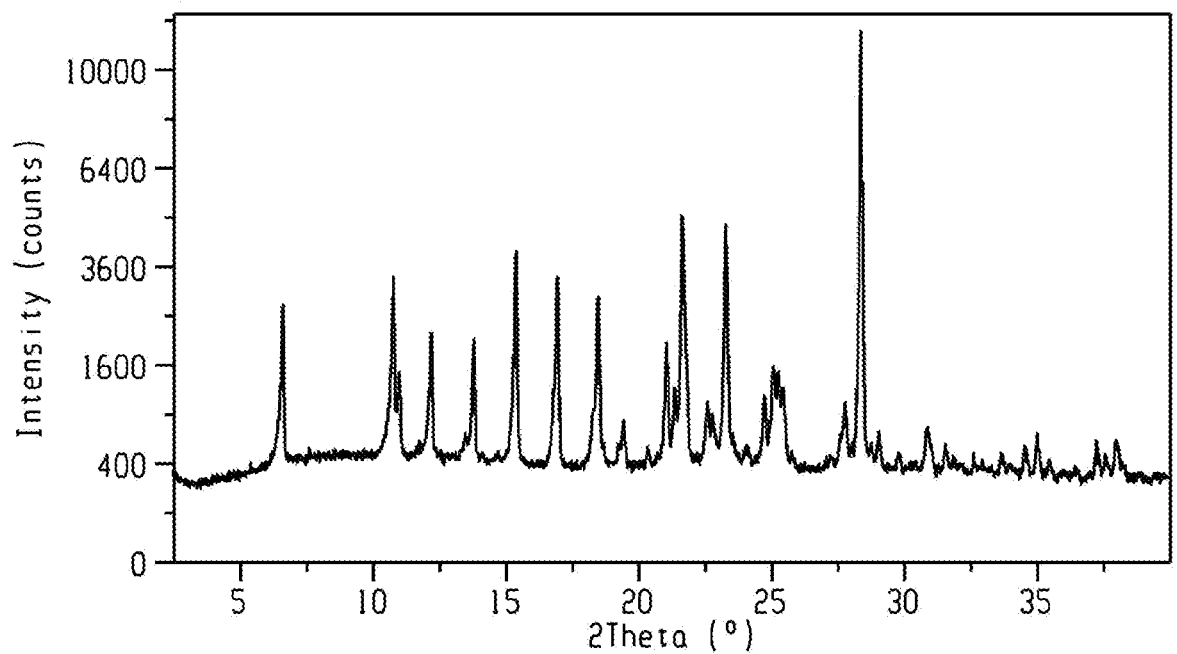
FIG. 25 shows a characteristic X-ray powder diffraction pattern of Rucaparib Hemi-Edisylate Form III.

Crystalline Form III of Rucaparib Hemi-Edisylate may be characterized by each of the above characteristics alone/or by all possible combinations, e.g., an XRPD pattern having peaks at 7.1, 17.2, 21.3, 21.8 and 23.5 degrees 2-theta±0.2 degrees 2-theta; an XRPD pattern as depicted in FIG. 25, and combinations thereof.

In one embodiment of the present disclosure, crystalline Form III of Rucaparib Hemi-Edisylate is isolated.

Figure 52A:
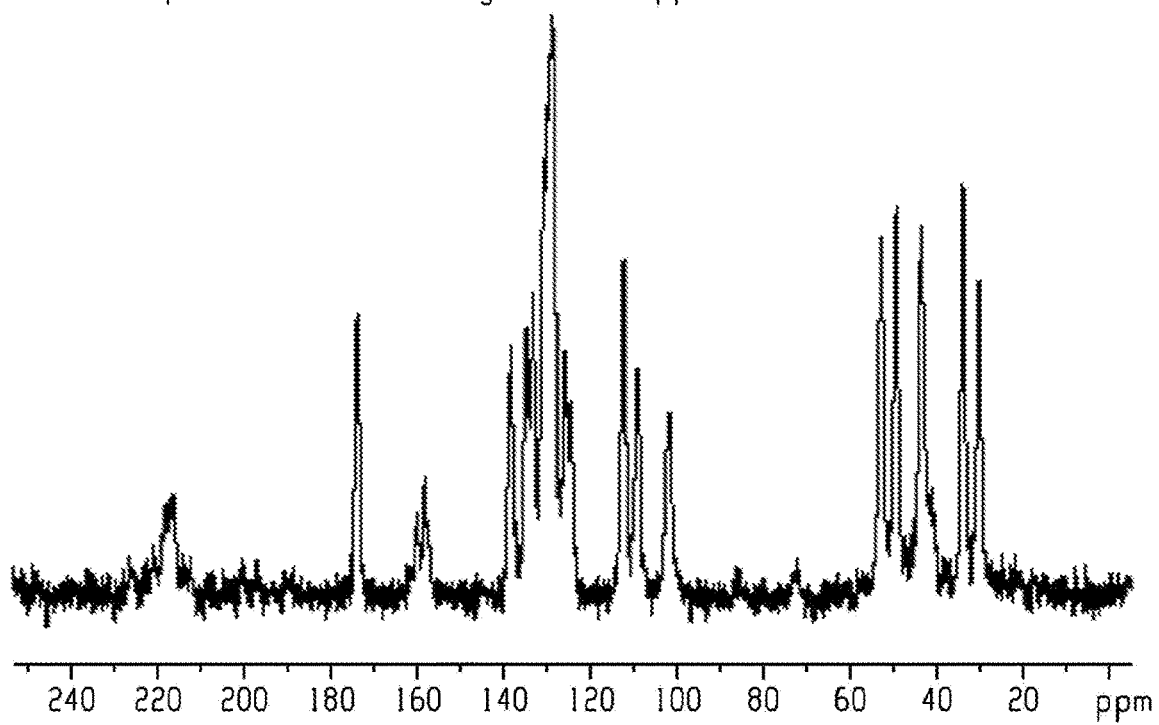
FIG. 52a shows a characteristic solid state $^{13}$C NMR spectrum of Form IV of Rucaparib Hemi-Edisylate at the range of 250-0 ppm.
Figure 52B:
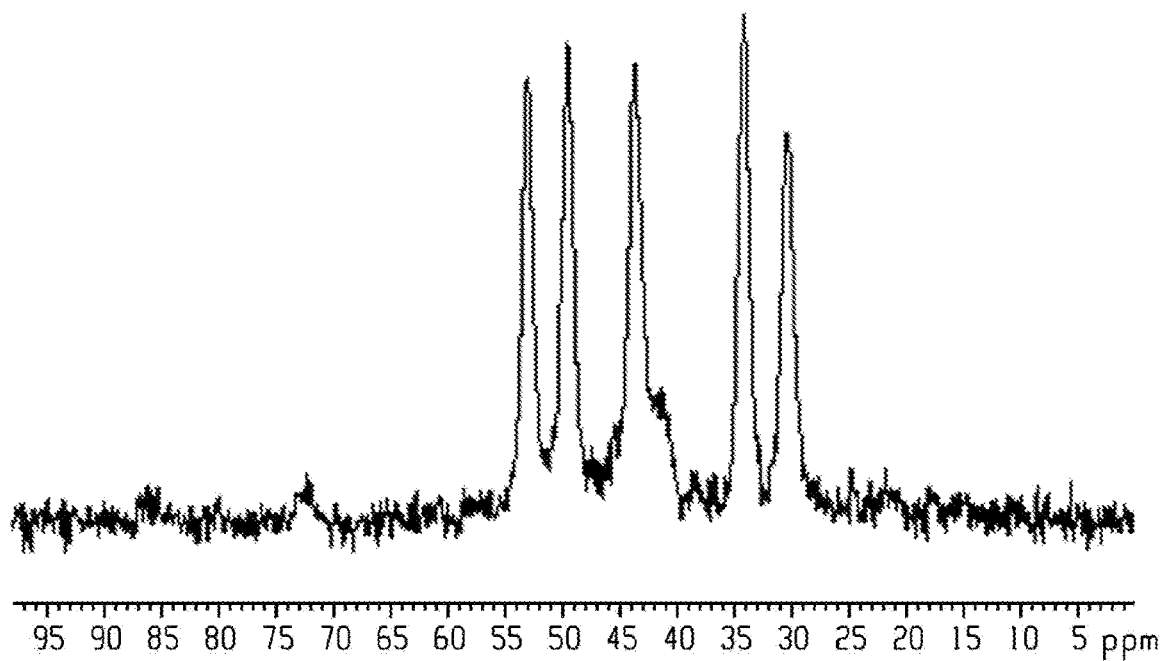
FIG. 52b shows a characteristic solid state $^{13}$C NMR spectrum of Form IV of Rucaparib Hemi-Edisylate at the range of 100-0 ppm.
Figure 52C:
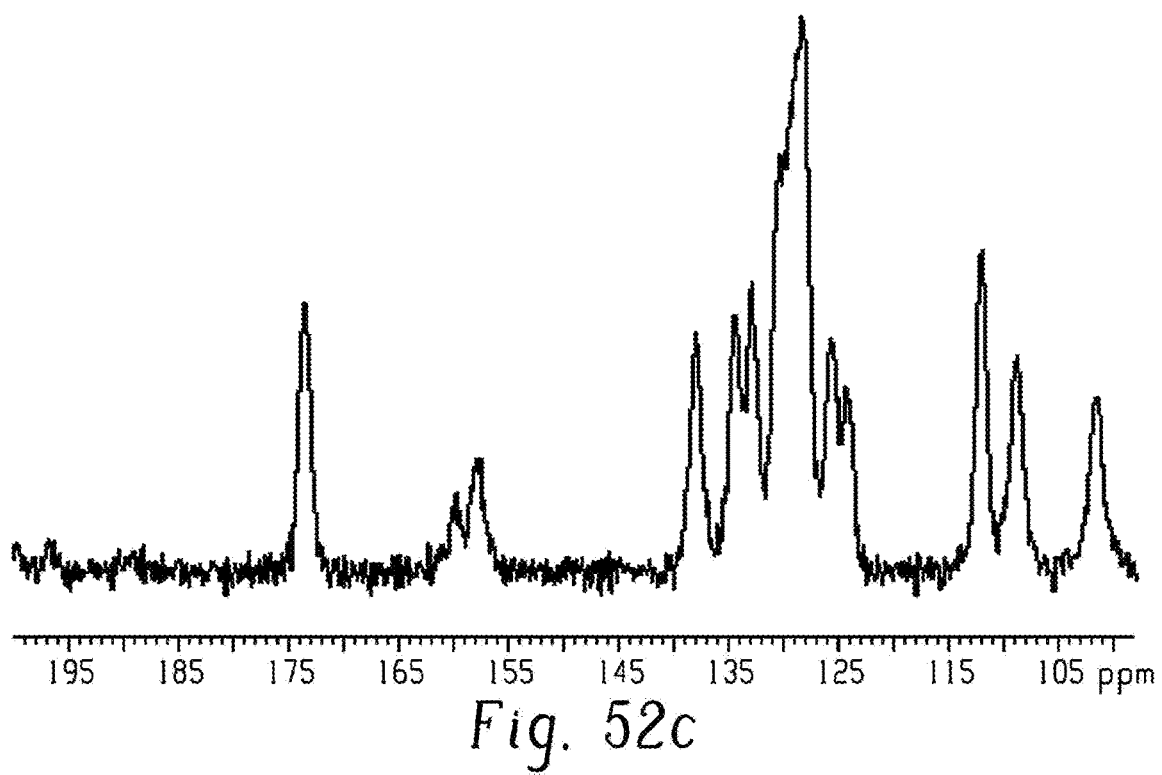
FIG. 52c shows a characteristic solid state $^{13}$C NMR spectrum of Form IV of Rucaparib Hemi-Edisylate at the range of 200-100 ppm.

In another aspect, the present disclosure relates to a crystalline form of Rucaparib Hemi-Edisylate, designated Form IV. The crystalline Form IV of Rucaparib Hemi-Edisylate may be characterized by data selected from one or more of the following: an X-ray powder diffraction pattern substantially as depicted in FIG. 26; an X-ray powder diffraction pattern having peaks at 9.0, 13.1, 15.4, 16.9 and 23.1 degrees 2-theta±0.2 degrees 2-theta, a solid state $^{13}C$ NMR spectrum having characteristic peaks at 132.9, 138.0 and 173.5 ppm±0.2 ppm; a solid state $^{13}C$ NMR spectrum having the following chemical shift absolute differences from a reference peak at 112.1 ppm±2 ppm: 20.8, 25.9 and 61.4 ppm±0.1 ppm; and a solid state $^{13}C$ NMR spectrum as depicted in FIG. 52a or 52b or 52c; and combinations of these data.

Crystalline Form IV of Rucaparib Hemi-Edisylate may be further characterized by an X-ray powder diffraction pattern having peaks at 9.0, 13.1, 15.4, 16.9 and 23.1 degrees 2-theta±0.2 degrees 2-theta and also having any one, two, three, four or five additional peaks selected from the group consisting of 11.5, 17.4, 19.6, 21.7 and 25.6 degrees 2-theta±0.2 degrees 2-theta.

Figure 26:
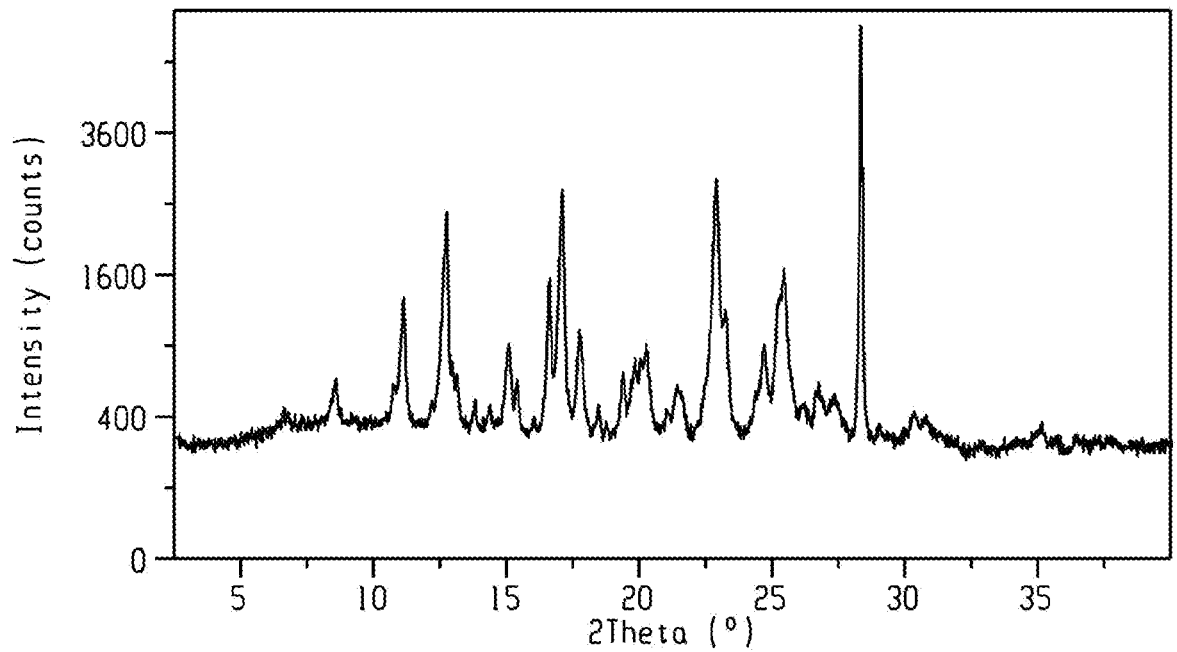
FIG. 26 shows a characteristic X-ray powder diffraction pattern of Rucaparib Hemi-Edisylate Form IV.

Crystalline Form IV of Rucaparib Hemi-Edisylate may be characterized by each of the above characteristics alone/or by all possible combinations, e.g., an XRPD pattern having peaks at 9.0, 13.1, 15.4, 16.9 and 23.1 degrees 2-theta±0.2 degrees 2-theta; an XRPD pattern as depicted in FIG. 26, and combinations thereof.

Crystalline Form IV of Rucaparib Hemi-Edisylate may be an anhydrous form.

In one embodiment of the present disclosure, crystalline Form IV of Rucaparib Hemi-Edisylate is isolated.

Crystalline Form IV of Rucaparib Hemi-Edisylate may have advantageous properties, as detailed above. Particularly, Crystalline Form IV of Rucaparib Hemi-Edisylate has lower API mass increase of the salt vs. the free base: it possess 9% mass increase while Rucaparib camsylate possess API mass increase of 72%. This is extremely important for a high drug loading treatment, and may contribute to compressibility of the API and to producing smaller tablet size. Also, it has good compressibility properties, and it may have at least comparable compressibility to that of Rucaparib camsylate. In addition, Crystalline Form IV of Rucaparib Hemi-Edisylate is non-hygroscopic; it is stable for a period of at least 1 month at 20-100% relative humidity (RH) at room temperature (RT) in open Petri dish; and it has improved kinetic solubility at various pH ranges.

In another aspect, the present disclosure relates to a crystalline form of Rucaparib Tosylate, designated Form I. The crystalline Form I of Rucaparib Tosylate may be characterized by data selected from one or more of the following: an X-ray powder diffraction pattern substantially as depicted in FIG. 17; an X-ray powder diffraction pattern having peaks at 5.8, 9.6, 13.5, 15.0 and 17.5 degrees 2-theta±0.2 degrees 2-theta, and combinations of these data.

Crystalline Form I of Rucaparib Tosylate may be further characterized by an X-ray powder diffraction pattern having peaks at 5.8, 9.6, 13.5, 15.0 and 17.5 degrees 2-theta±0.2 degrees 2-theta and also having any one, two, three, four or five additional peaks selected from the group consisting of 9.0, 11.4, 11.6, 16.3 and 21.5 degrees 2-theta±0.2 degrees 2-theta.

Figure 17:
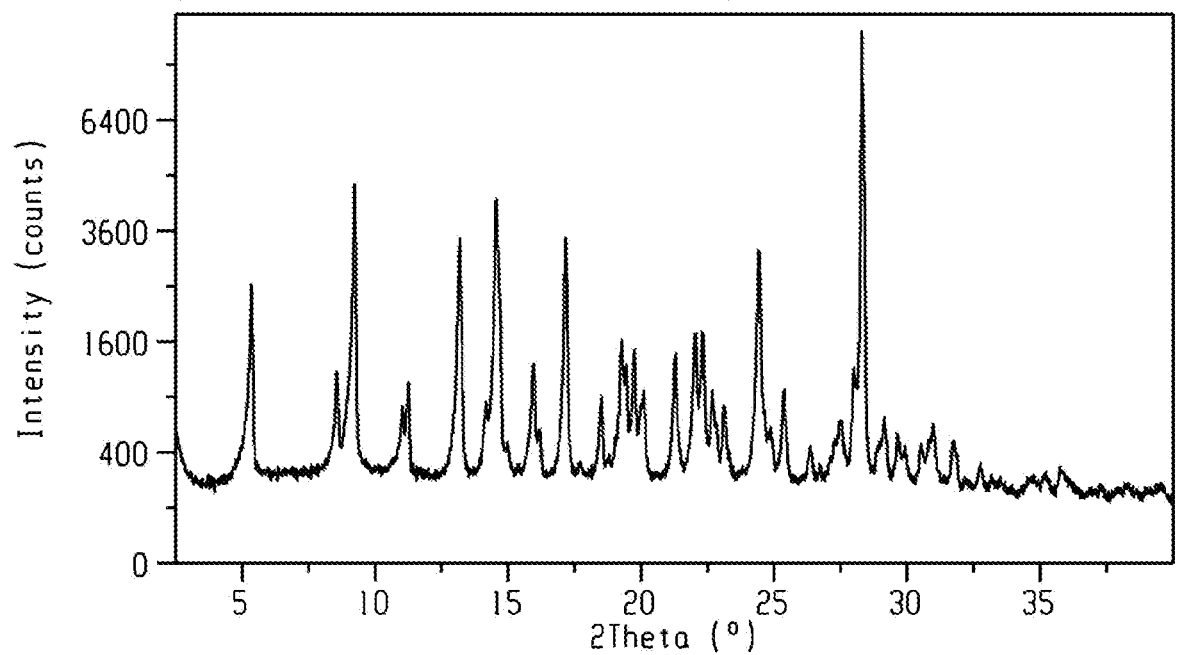
FIG. 17 shows a characteristic X-ray powder diffraction pattern of Rucaparib Tosylate Form I.

Crystalline Form I of Rucaparib Tosylate may be characterized by each of the above characteristics alone/or by all possible combinations, e.g., an XRPD pattern having peaks at 5.8, 9.6, 13.5, 15.0 and 17.5 degrees 2-theta±0.2 degrees 2-theta; an XRPD pattern as depicted in FIG. 17, and combinations thereof.

In one embodiment of the present disclosure, crystalline Form I of Rucaparib Tosylate is isolated.

The present disclosure comprises a crystalline form of Rucaparib Tosylate, designated Form II. The crystalline Form II of Rucaparib Tosylate may be characterized by data selected from one or more of the following: an X-ray powder diffraction pattern substantially as depicted in FIG. 20; an X-ray powder diffraction pattern having peaks at 7.1, 10.5, 12.0, 13.1 and 19.3 degrees 2-theta±0.2 degrees 2-theta; and combinations of these data.

Crystalline Form II of Rucaparib Tosylate may be further characterized by an X-ray powder diffraction pattern having peaks at 7.1, 10.5, 12.0, 13.1 and 19.3 degrees 2-theta±0.2 degrees 2-theta, and also having any one, two, three, four or five additional peaks selected from the group consisting of 6.9, 11.3, 16.7, 24.3 and 24.7 degrees 2-theta±0.2 degrees 2-theta.

Figure 20:
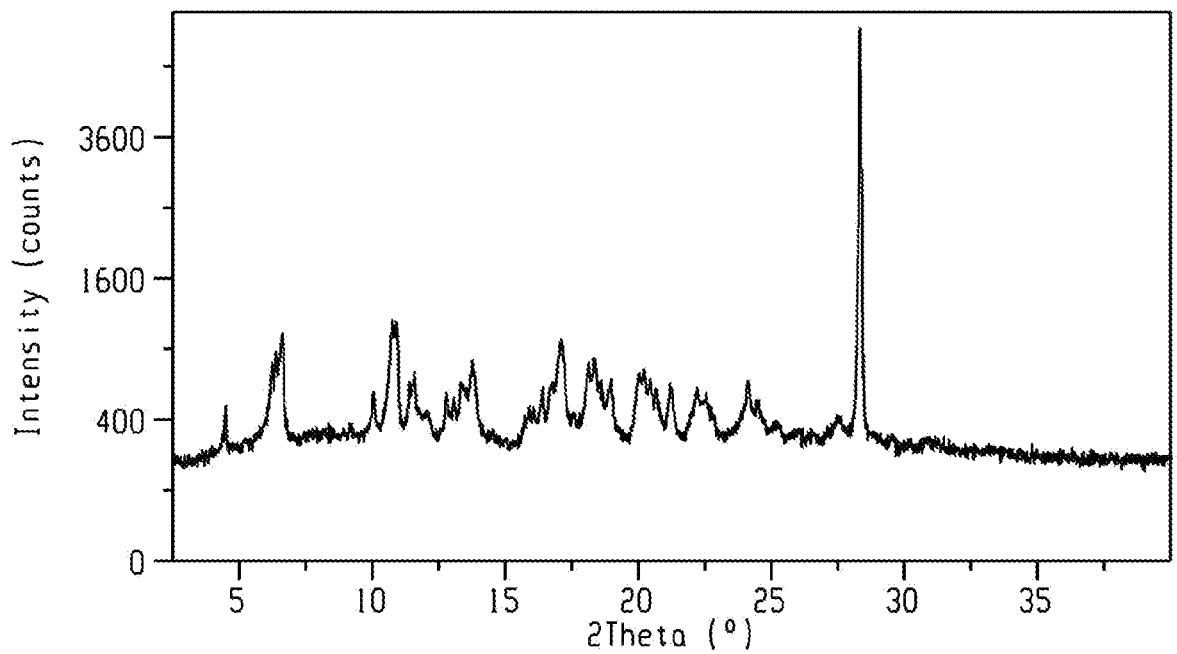
FIG. 20 shows a characteristic X-ray powder diffraction pattern of Rucaparib Tosylate Form II.

Crystalline Form II of Rucaparib Tosylate may be characterized by each of the above characteristics alone/or by all possible combinations, e.g., an XRPD pattern having peaks at 7.1, 10.5, 12.0, 13.1 and 19.3 degrees 2-theta±0.2 degrees 2-theta; an XRPD pattern as depicted in FIG. 20, and combinations thereof.

In one embodiment of the present disclosure, crystalline Form II of Rucaparib Tosylate is isolated.

Figure 53A:
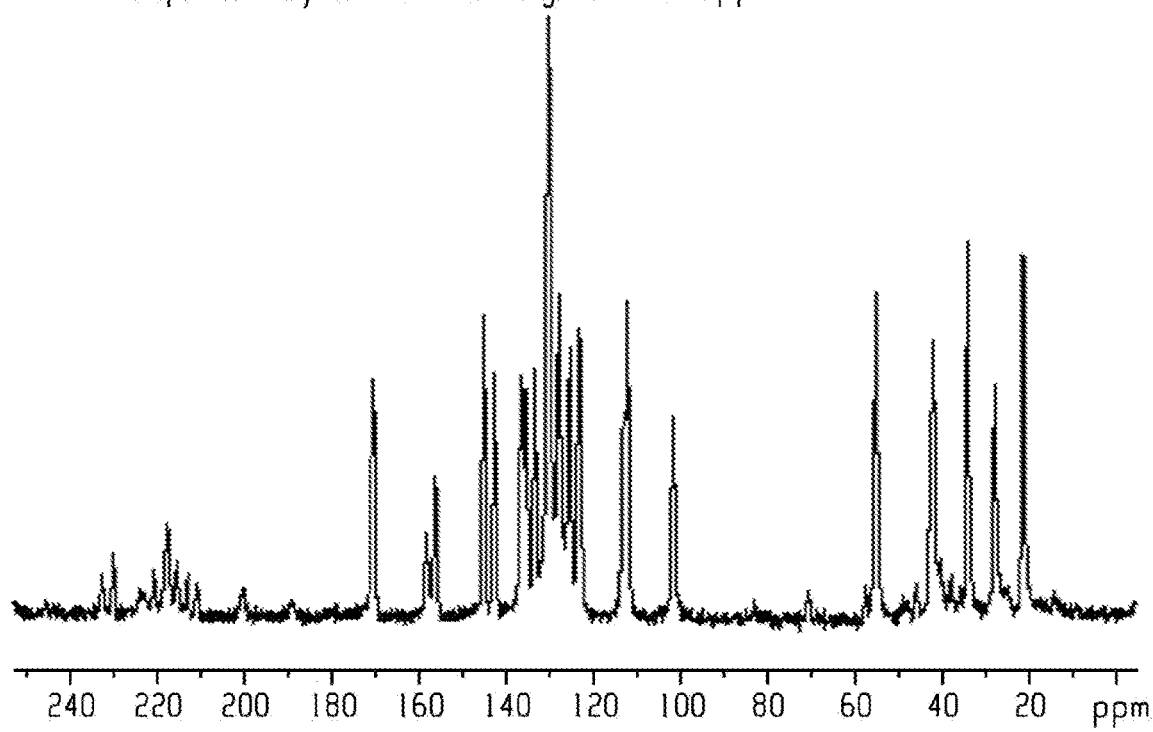
FIG. 53a shows a characteristic solid state $^{13}$C NMR spectrum of Form III of Rucaparib tosylate at the range of 250-0 ppm.
Figure 53B:
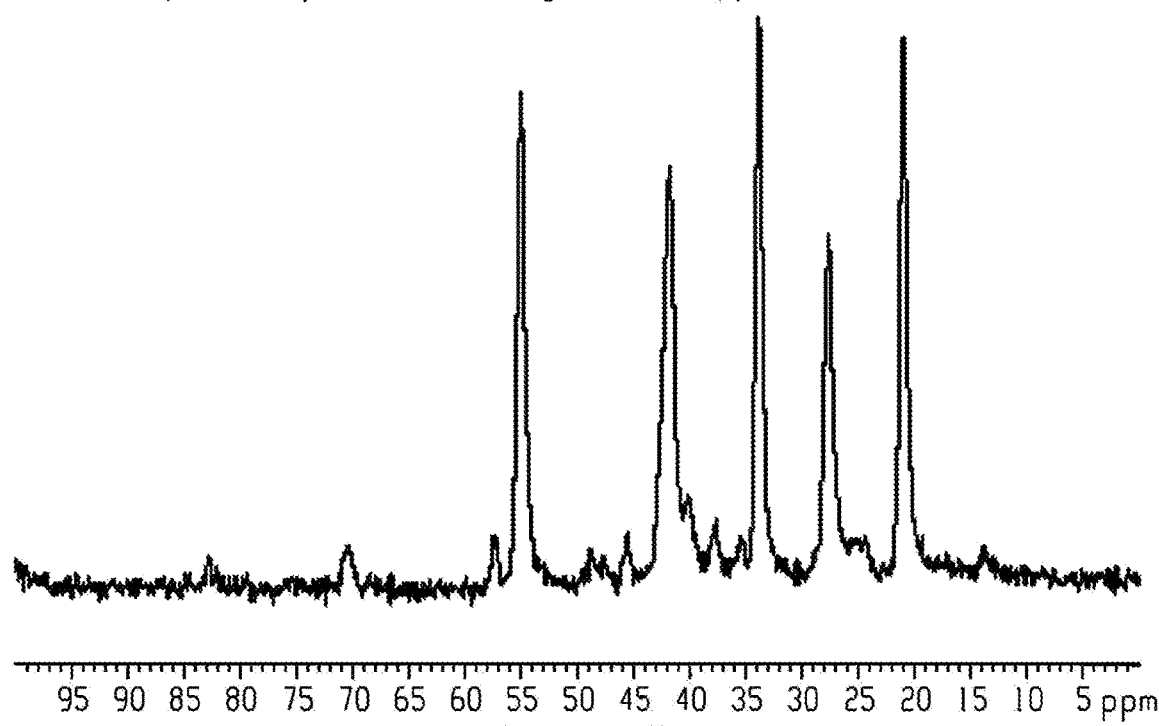
FIG. 53b shows a characteristic solid state $^{13}$C NMR spectrum of Form III of Rucaparib tosylate at the range of 100-0 ppm.
Figure 53C:
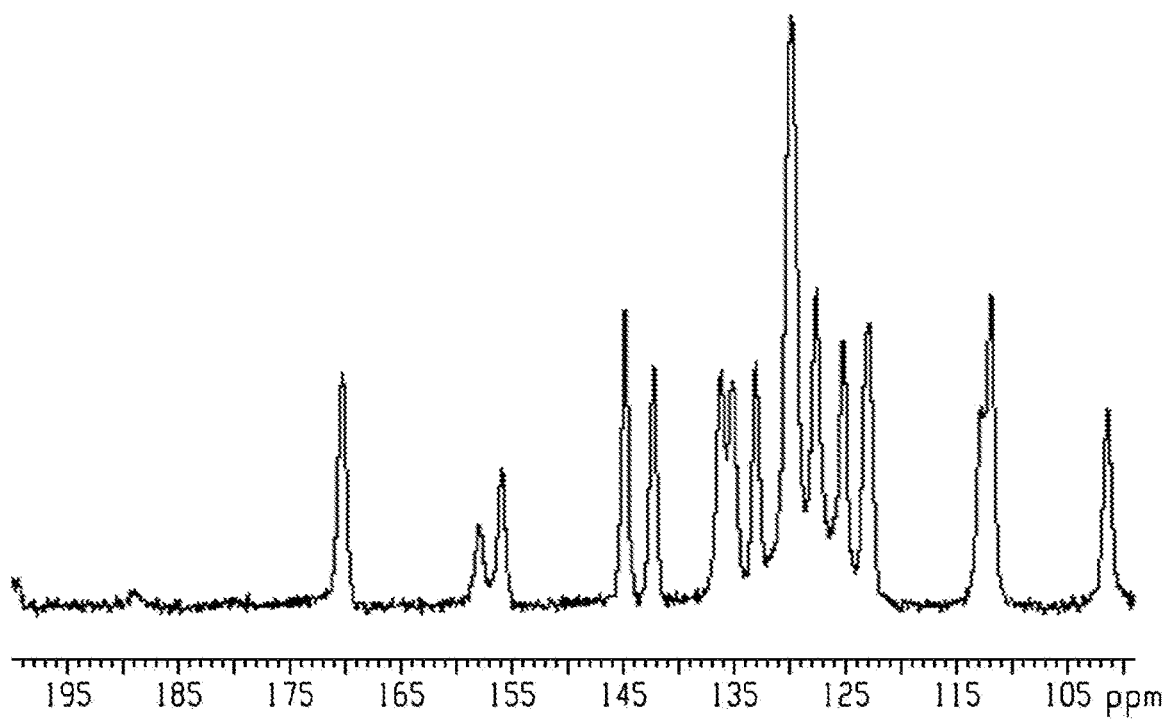
FIG. 53c shows a characteristic solid state $^{13}$C NMR spectrum of Form III of Rucaparib tosylate at the range of 200-100 ppm.

In another aspect, the present disclosure relates to a crystalline form of Rucaparib Tosylate, designated Form III. The crystalline Form III of Rucaparib Tosylate may be characterized by data selected from one or more of the following: an X-ray powder diffraction pattern substantially as depicted in FIG. 21; an X-ray powder diffraction pattern having peaks at 10.0, 13.8, 14.5, 17.0 and 18.5 degrees 2-theta±0.2 degrees 2-theta, a solid state $^{13}C$ NMR spectrum having characteristic peaks at 111.9, 125.2, 127.5, 142.3 and 144.8 ppm±0.2 ppm; a solid state $^{13}C$ NMR spectrum having the following chemical shift absolute differences from a reference peak at 101.4 ppm±2 ppm: 10.5, 23.8, 26.1, 34.7, 40.9 and 43.4 ppm±0.1 ppm; and a solid state $^{13}C$ NMR spectrum as depicted in FIG. 53a or 53b or 53c; and combinations of these data.

Crystalline Form III of Rucaparib Tosylate may be further characterized by an X-ray powder diffraction pattern having peaks at 10.0, 13.8, 14.5, 17.0 and 18.5 degrees 2-theta±0.2 degrees 2-theta, and also having any one, two, three, four or five additional peaks selected from the group consisting of 6.5, 20.4, 22.9, 23.7 and 25.8 degrees 2-theta±0.2 degrees 2-theta.

Figure 21:
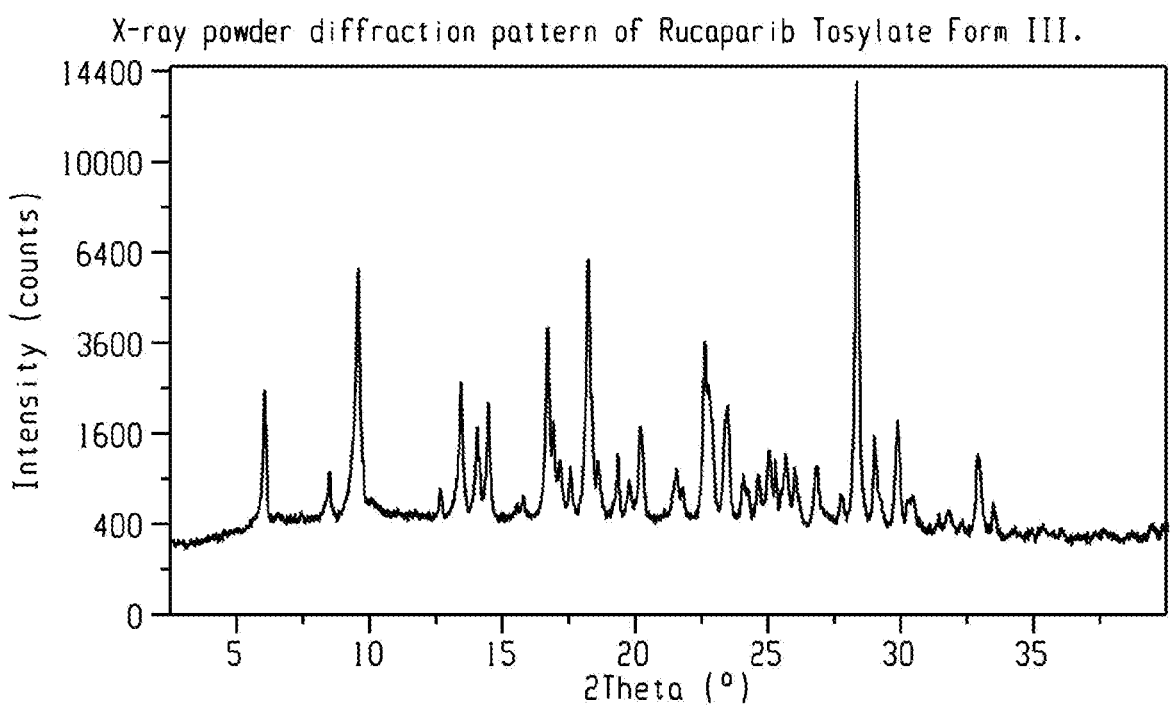
FIG. 21 shows a characteristic X-ray powder diffraction pattern of Rucaparib Tosylate Form III.

Crystalline Form III of Rucaparib Tosylate may be characterized by each of the above characteristics alone/or by all possible combinations, e.g., an XRPD pattern having peaks at 10., 13.8, 14.5, 17.0 and 18.5 degrees 2-theta±0.2 degrees 2-theta; an XRPD pattern as depicted in FIG. 21, and combinations thereof.

Crystalline Form III of Rucaparib Tosylate may be an anhydrous form.

In one embodiment of the present disclosure, crystalline Form III of Rucaparib Tosylate is isolated.

Crystalline Form III of Rucaparib Tosylate may have advantageous properties, as detailed above. Particularly, Crystalline Form III of Rucaparib Tosylate has lower API mass increase of the salt vs. the free base: it possess 53% mass increase while Rucaparib camsylate possess API mass increase of 72%. This is extremely important for a high drug loading treatment, and may contribute to compressibility of the API and to producing smaller tablet size. Also, it has good compressibility properties, and it may have at least comparable compressibility to that of Rucaparib camsylate. In addition, Crystalline Form III of Rucaparib Tosylate is non-hygroscopic; it is stable for a period of at least 1 month at 20-100% relative humidity (RH) at room temperature (RT) in open Petri dish; and it has improved kinetic solubility at various pH ranges.

In another aspect, the present disclosure relates to a crystalline form of Rucaparib Tosylate, designated Form IV. The crystalline Form IV of Rucaparib Tosylate may be characterized by data selected from one or more of the following: an X-ray powder diffraction pattern substantially as depicted in FIG. 22; an X-ray powder diffraction pattern having peaks at 6.5, 8.0, 9.5, 16.1 and 20.9 degrees 2-theta±0.2 degrees 2-theta, and combinations of these data.

Crystalline Form IV of Rucaparib Tosylate may be further characterized by an X-ray powder diffraction pattern having peaks at 6.5, 8.0, 9.5, 16.1 and 20.9 degrees 2-theta±0.2 degrees 2-theta and also having any one, two, three, four or five additional peaks selected from the group consisting of 11.1, 12.5, 13.4, 14.1 and 24.1 degrees 2-theta±0.2 degrees 2-theta.

Figure 22:
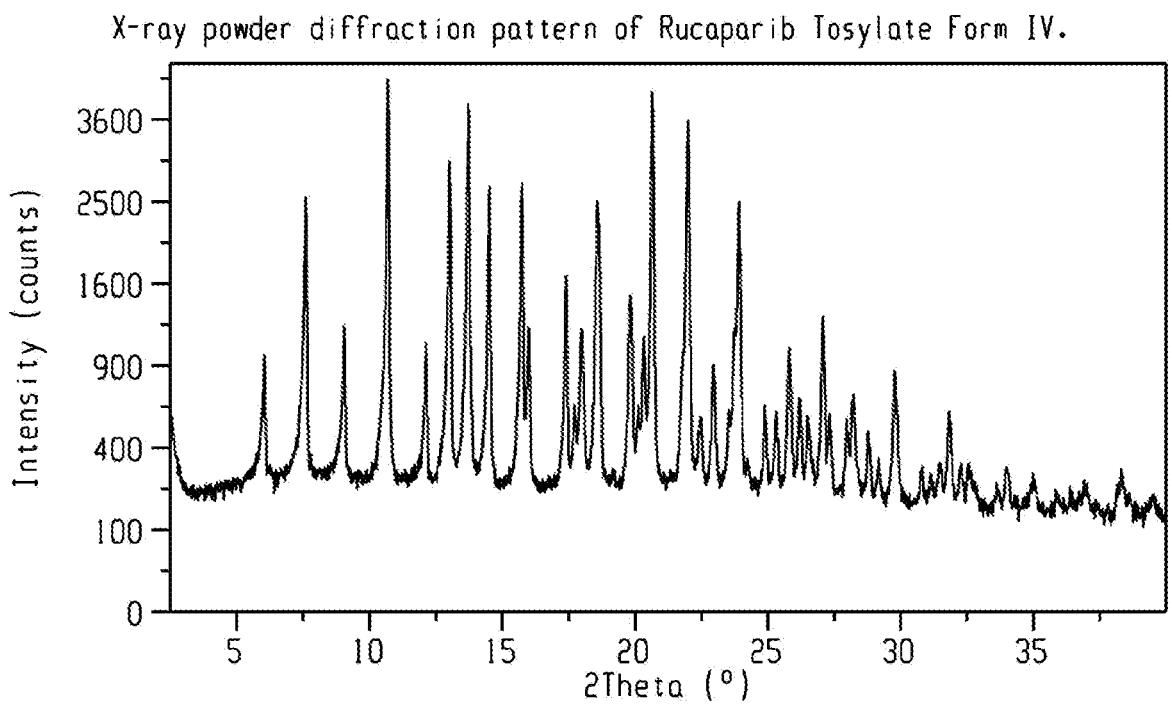
FIG. 22 shows a characteristic X-ray powder diffraction pattern of Rucaparib Tosylate Form IV.

Crystalline Form IV of Rucaparib Tosylate may be characterized by each of the above characteristics alone/or by all possible combinations, e.g., an XRPD pattern having peaks at 6.5, 8.0, 9.5, 16.1 and 20.9 degrees 2-theta±0.2 degrees 2-theta; an XRPD pattern as depicted in FIG. 22, and combinations thereof.

In one embodiment of the present disclosure, crystalline Form IV of Rucaparib Tosylate is isolated.

Figure 54A:
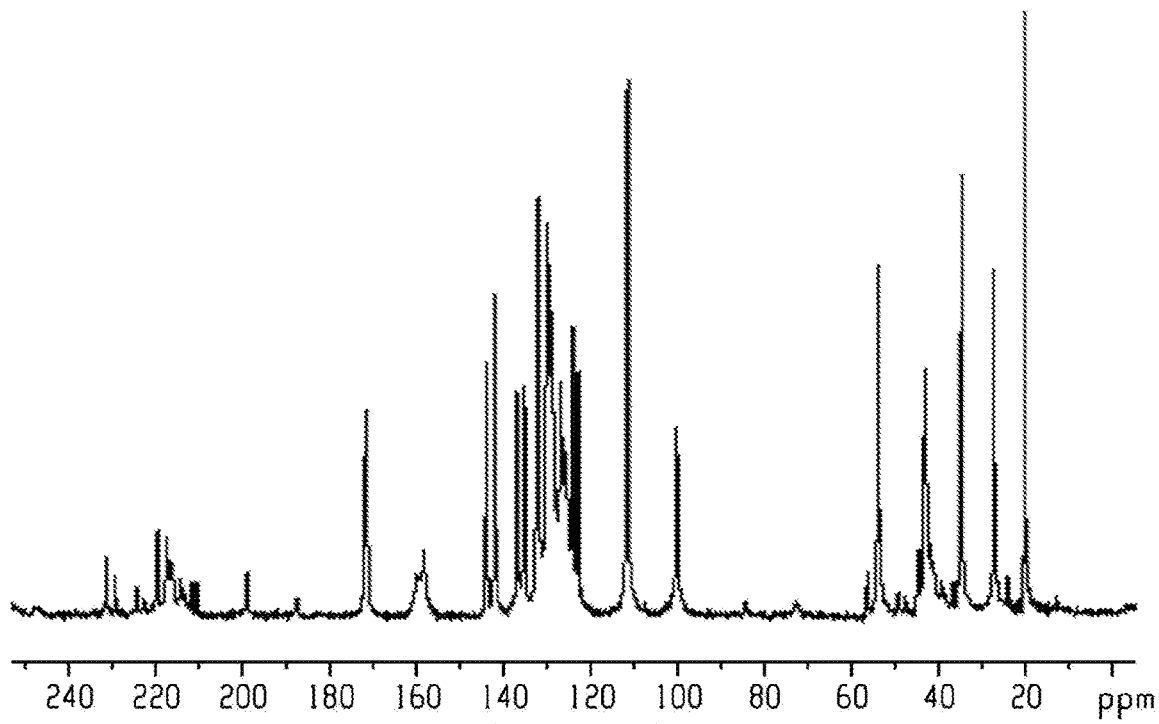
FIG. 54a shows a characteristic solid state $^{13}$C NMR spectrum of Form V of Rucaparib tosylate at the range of 250-0 ppm.
Figure 54B:
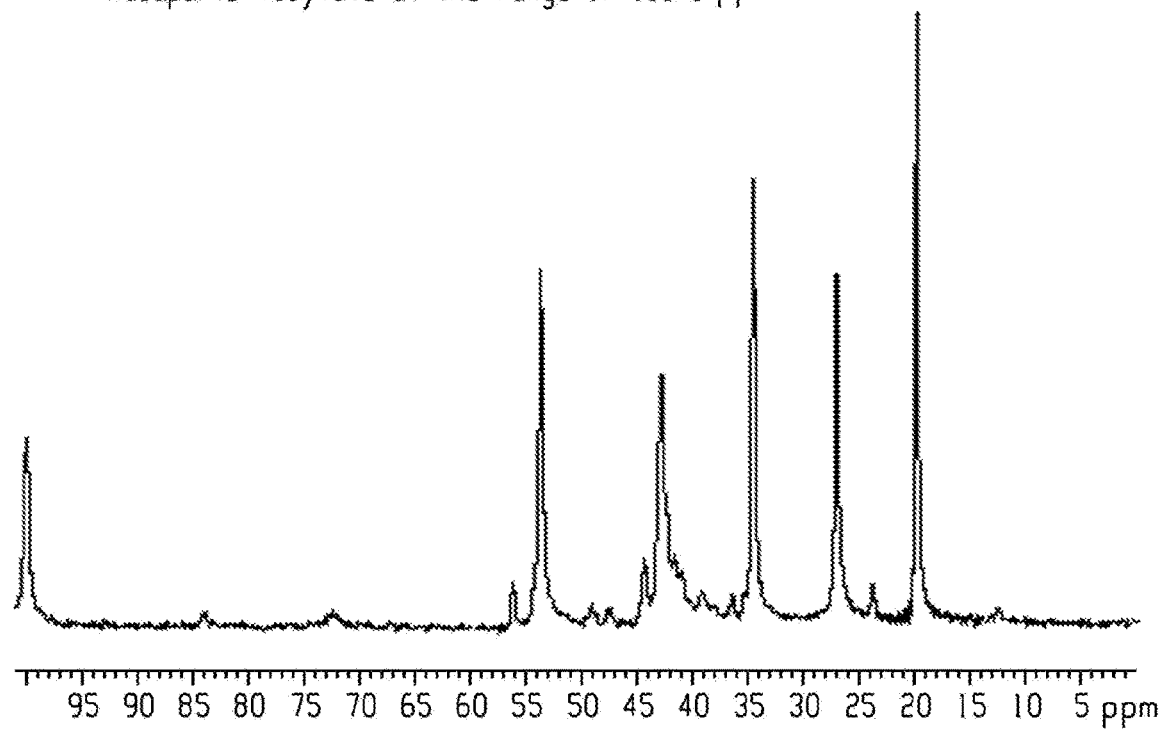
FIG. 54b shows a characteristic solid state $^{13}$C NMR spectrum of Form V of Rucaparib tosylate at the range of 100-0 ppm.
Figure 54C:
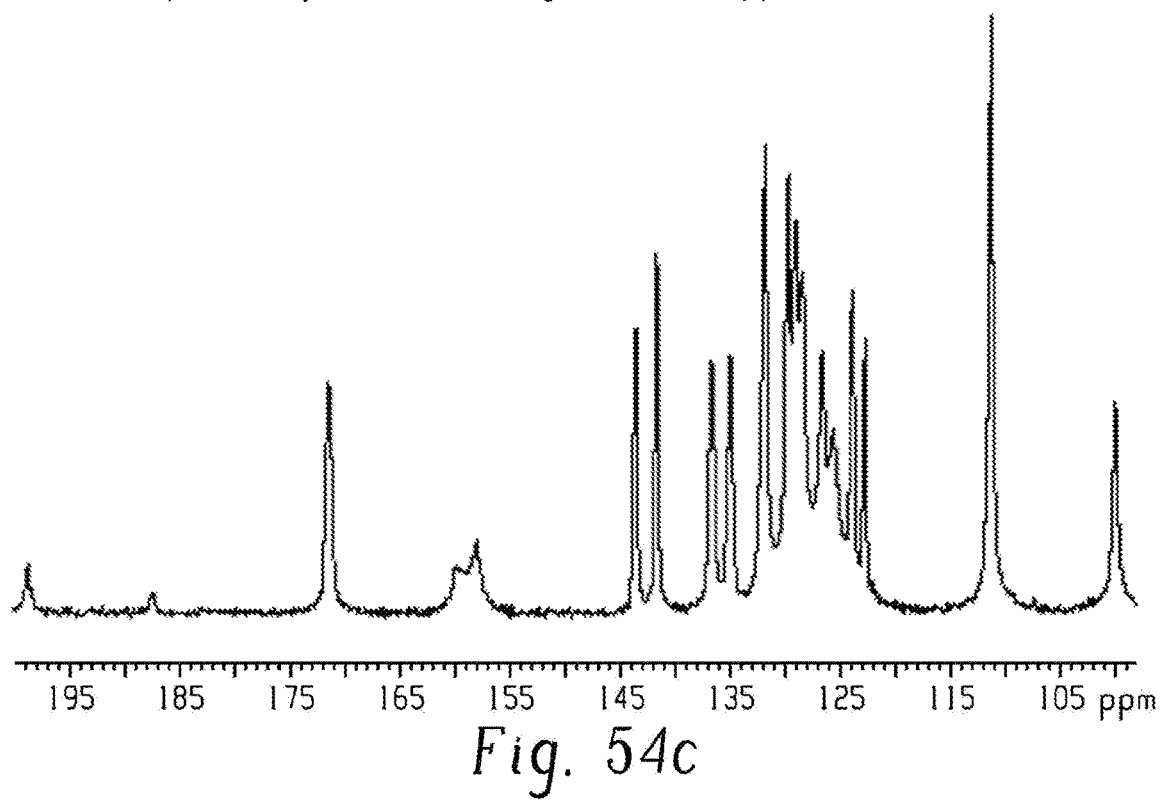
FIG. 54c shows a characteristic solid state $^{13}$C NMR spectrum of Form V of Rucaparib tosylate at the range of 200-100 ppm.

In another aspect, the present disclosure relates to a crystalline form of Rucaparib Tosylate, designated Form V. The crystalline Form V of Rucaparib Tosylate may be characterized by data selected from one or more of the following: an X-ray powder diffraction pattern substantially as depicted in FIG. 23; an X-ray powder diffraction pattern having peaks at 7.1, 12.5, 14.4, 17.4 and 24.9 degrees 2-theta±0.2 degrees 2-theta, a solid state $^{13}C$ NMR spectrum having characteristic peaks at 111.2, 122.7, 123.8, 141.6 and 143.5 ppm±0.2 ppm; a solid state $^{13}C$ NMR spectrum having the following chemical shift absolute differences from a reference peak at 99.9 ppm±2 ppm: 11.3, 22.8, 23.9, 41.7 and 43.6 ppm±0.1 ppm; and a solid state $^{13}C$ NMR spectrum as depicted in FIG. 54a or 54b or 54c; and combinations of these data.

Crystalline Form V of Rucaparib Tosylate may be further characterized by an X-ray powder diffraction pattern having peaks at 7.1, 12.5, 14.4, 17.4 and 24.9 degrees 2-theta±0.2 degrees 2-theta and also having any one, two, three, four or five additional peaks selected from the group consisting of 16.3, 18.6, 22.5, 24.2 and 26.0 degrees 2-theta±0.2 degrees 2-theta.

Figure 23:
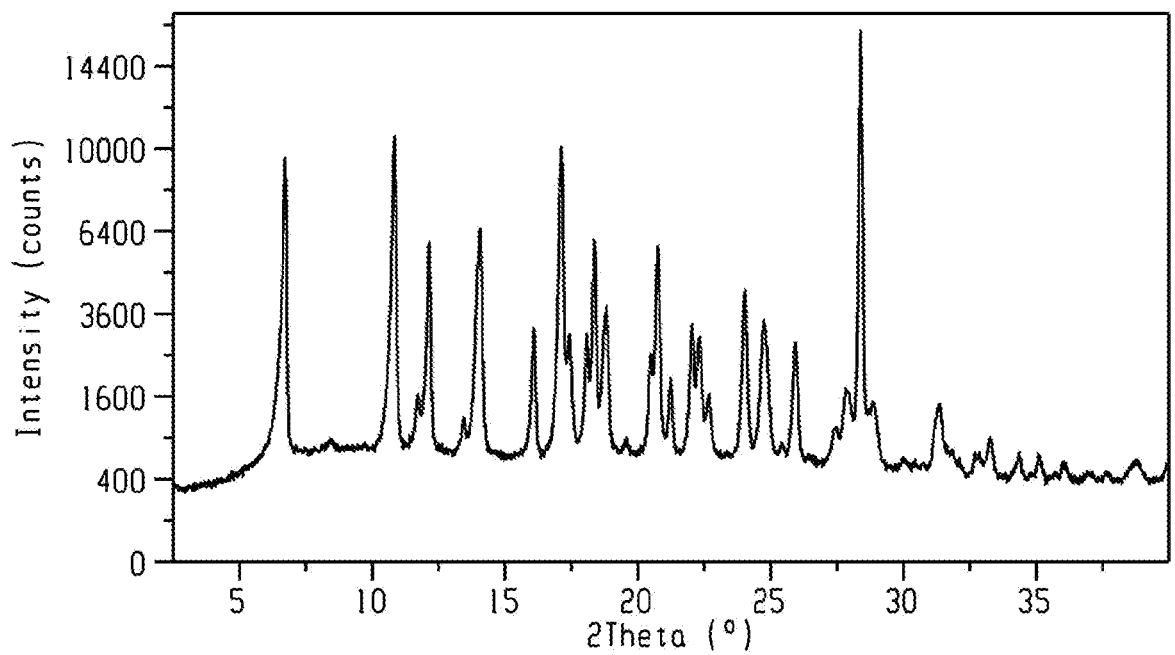
FIG. 23 shows a characteristic X-ray powder diffraction pattern of Rucaparib Tosylate Form V.

Crystalline Form V of Rucaparib Tosylate may be characterized by each of the above characteristics alone/or by all possible combinations, e.g., an XRPD pattern having peaks at 7.1, 12.5, 14.4, 17.4 and 24.9 degrees 2-theta±0.2 degrees 2-theta; an XRPD pattern as depicted in FIG. 23, and combinations thereof.

Crystalline Form V of Rucaparib Tosylate may be an anhydrous form.

In one embodiment of the present disclosure, crystalline Form V of Rucaparib Tosylate is isolated.

Crystalline Form V of Rucaparib Tosylate may have advantageous properties, as detailed above. Particularly, Crystalline Form V of Rucaparib Tosylate has lower API mass increase of the salt vs. the free base: it possess 53% mass increase while Rucaparib camsylate possess API mass increase of 72%. This is extremely important for a high drug loading treatment, and may contribute to compressibility of the API and to producing smaller tablet size. In addition, Crystalline Form V of Rucaparib Tosylate is non-hygroscopic; it is stable for a period of at least 1 month at 20-100% relative humidity (RH) at room temperature (RT) in open Petri dish; and it has improved kinetic solubility at various pH ranges.

In another aspect, the present disclosure relates to a mixture of Crystalline Form V of Rucaparib Tosylate and Crystalline Form VI of Rucaparib Tosylate. This mixture may be characterized by data selected from one or more of the following: an X-ray powder diffraction pattern substantially as depicted in FIG. 24; an X-ray powder diffraction pattern having peaks at 6.2 and 13.8 degrees 2-theta±0.2 degrees 2-theta, and combinations of these data.

Figure 24:
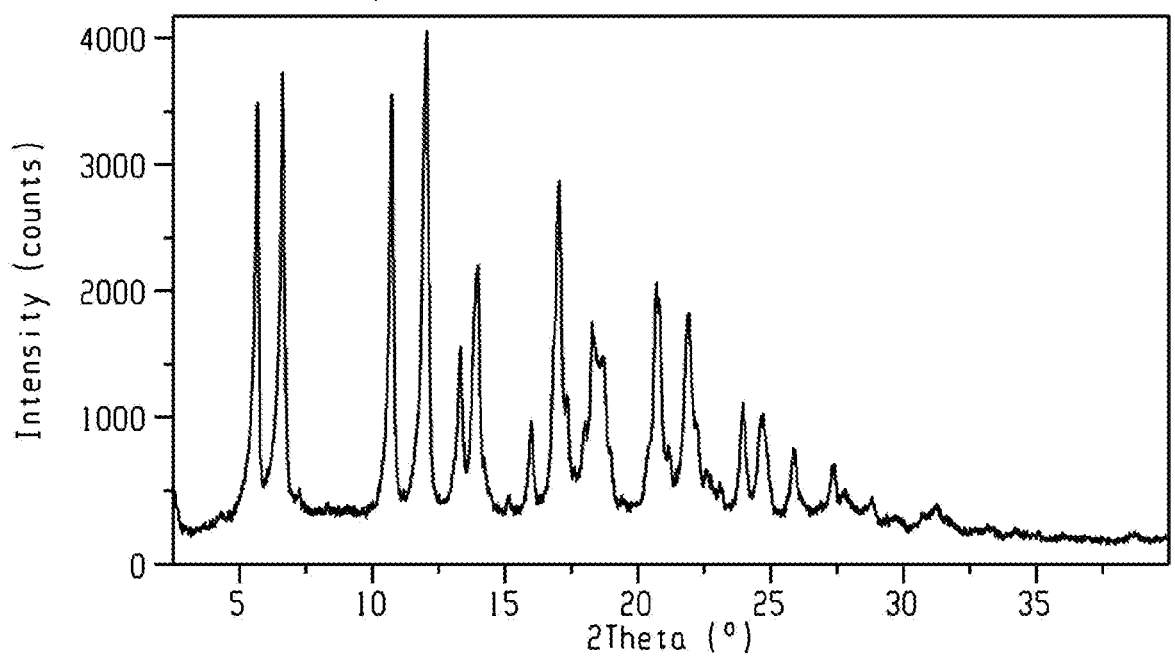
FIG. 24 shows an X-ray powder diffraction pattern of a mixture of Rucaparib Tosylate Form V and Rucaparib Tosylate Form VI, obtained by example 51.

The mixture of Crystalline Form V of Rucaparib Tosylate and Crystalline Form VI of Rucaparib Tosylate may be characterized by each of the above characteristics alone/or by all possible combinations, e.g., an XRPD pattern having peaks at 6.2 and 13.8 degrees 2-theta±0.2 degrees 2-theta; an XRPD pattern as depicted in FIG. 24, and combinations thereof.

In one embodiment of the present disclosure, the mixture of Crystalline Form V of Rucaparib Tosylate and Crystalline Form VI of Rucaparib Tosylate is isolated.

In another aspect, the present disclosure relates to a crystalline form of Rucaparib Mesylate, designated Form I. The crystalline Form I of Rucaparib Mesylate may be characterized by data selected from one or more of the following: an X-ray powder diffraction pattern substantially as depicted in FIG. 18; an X-ray powder diffraction pattern having peaks at 5.4, 5.6, 11.2, 13.3 and 16.7 degrees 2-theta±0.2 degrees 2-theta, and combinations of these data.

Crystalline Form I of Rucaparib Mesylate may be further characterized by an X-ray powder diffraction pattern having peaks at 5.4, 5.6, 11.2, 13.3 and 16.7 degrees 2-theta±0.2 degrees 2-theta and also having any one, two, three, four or five additional peaks selected from the group consisting of 12.7, 13.8, 20.0, 21.6 and 23.7 degrees 2-theta±0.2 degrees 2-theta.

Figure 18:
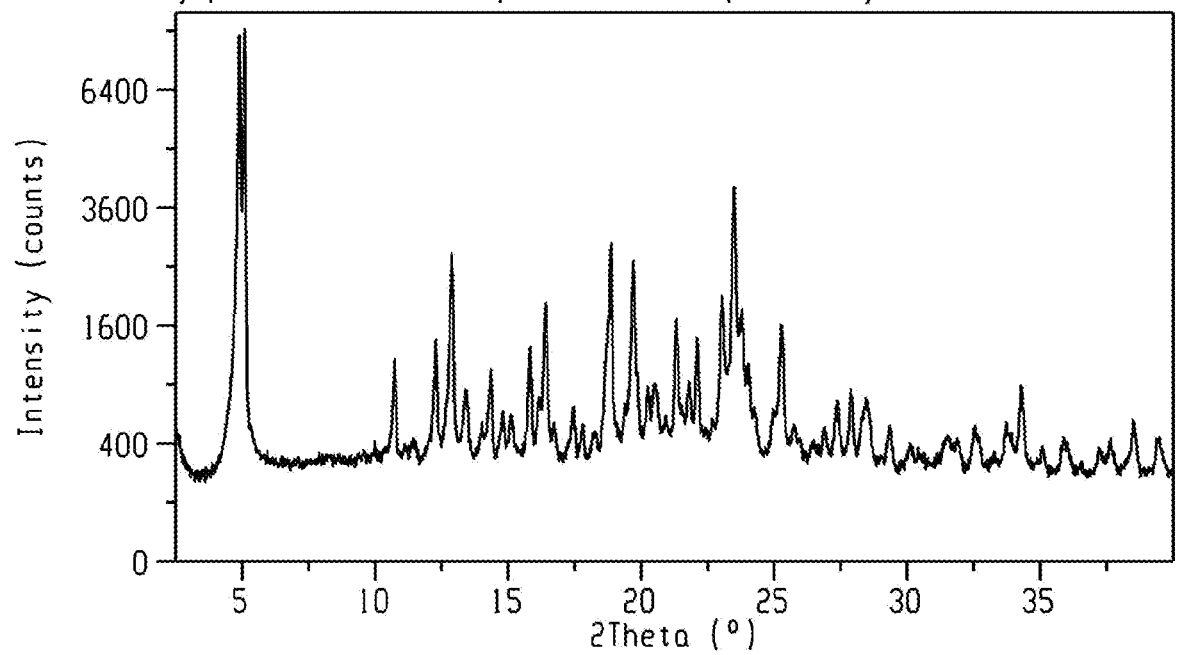
FIG. 18 shows a characteristic X-ray powder diffraction pattern of Rucaparib Mesylate Form I.

Crystalline Form I of Rucaparib Mesylate may be characterized by each of the above characteristics alone/or by all possible combinations, e.g., an XRPD pattern having peaks at 5.4, 5.6, 11.2, 13.3 and 16.7 degrees 2-theta±0.2 degrees 2-theta; an XRPD pattern as depicted in FIG. 18, and combinations thereof.

In one embodiment of the present disclosure, crystalline Form I of Rucaparib Mesylate is isolated.

In another aspect, the present disclosure relates to a crystalline form of Rucaparib Mesylate, designated Form II. The crystalline Form II of Rucaparib Mesylate may be characterized by data selected from one or more of the following: an X-ray powder diffraction pattern substantially as depicted in FIG. 19; an X-ray powder diffraction pattern having peaks at 5.8, 6.0, 11.7, 12.0 and 12.4 degrees 2-theta±0.2 degrees 2-theta, and combinations of these data.

Crystalline Form II of Rucaparib Mesylate may be further characterized by an X-ray powder diffraction pattern having peaks at 5.8, 6.0, 11.7, 12.0 and 12.4 degrees 2-theta±0.2 degrees 2-theta and also having any one, two, three, four or five additional peaks selected from the group consisting of 10.4, 17.2, 19.0, 20.9 and 22.5 degrees 2-theta±0.2 degrees 2-theta.

Figure 19:
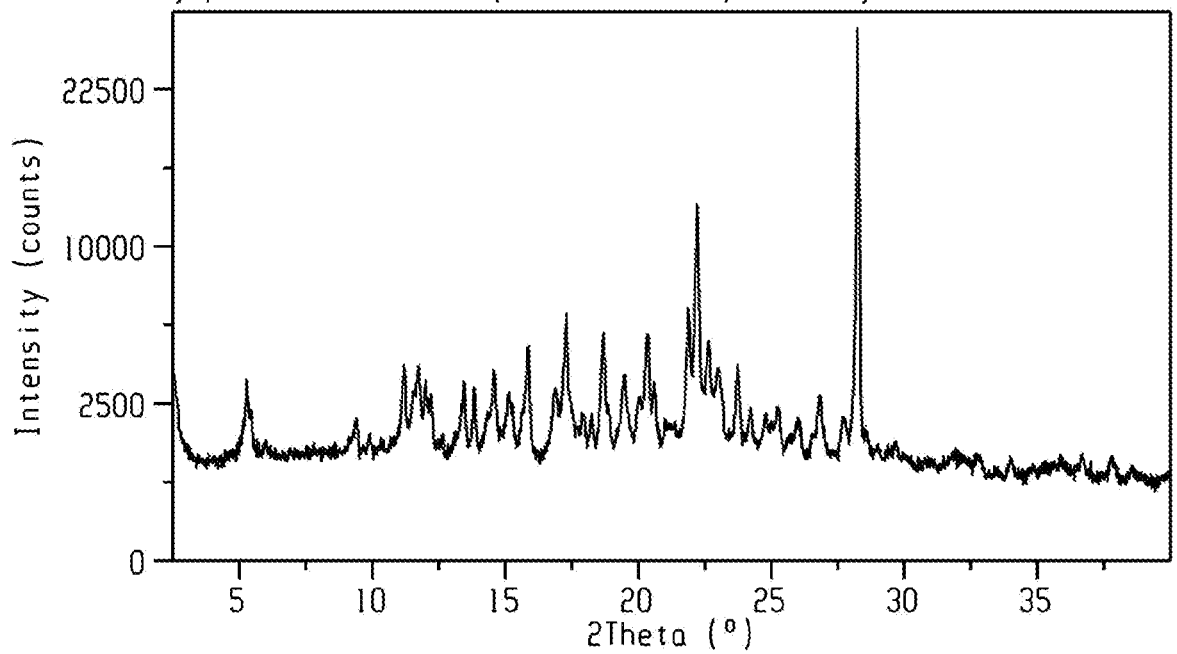
FIG. 19 shows a characteristic X-ray powder diffraction pattern of Rucaparib Mesylate Form II.

Crystalline Form II of Rucaparib Mesylate may be characterized by each of the above characteristics alone/or by all possible combinations, e.g., an XRPD pattern having peaks at 5.8, 6.0, 11.7, 12.0 and 12.4 degrees 2-theta±0.2 degrees 2-theta; an XRPD pattern as depicted in FIG. 19, and combinations thereof.

In one embodiment of the present disclosure, crystalline Form II of Rucaparib Mesylate is isolated.

In another aspect, the present disclosure relates to a crystalline form of Rucaparib Esylate, designated Form I. The crystalline Form I of Rucaparib Esylate may be characterized by data selected from one or more of the following: an X-ray powder diffraction pattern substantially as depicted in FIG. 29; an X-ray powder diffraction pattern having peaks at 11.0, 11.4, 12.2, 12.6 and 15.6 degrees 2-theta±0.2 degrees 2-theta, and combinations of these data.

Crystalline Form I of Rucaparib Esylate may be further characterized by an X-ray powder diffraction pattern having peaks at 11.0, 11.4, 12.2, 12.6 and 15.6 degrees 2-theta±0.2 degrees 2-theta and also having any one, two, three, four or five additional peaks selected from the group consisting of 16.1, 17.3, 20.1, 25.0 and 25.4 degrees 2-theta±0.2 degrees 2-theta.

Figure 29:
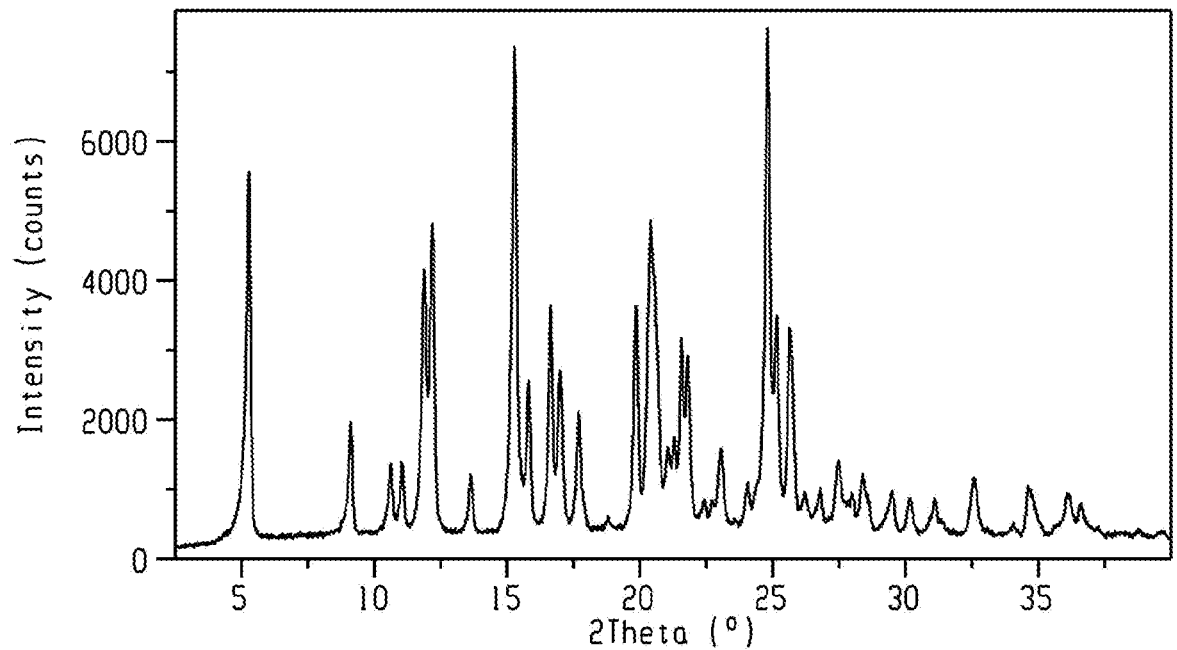
FIG. 29 shows a characteristic X-ray powder diffraction pattern of Rucaparib Esylate Form I.

Crystalline Form I of Rucaparib Esylate may be characterized by each of the above characteristics alone/or by all possible combinations, e.g., an XRPD pattern having peaks at 11.0, 11.4, 12.2, 12.6 and 15.6 degrees 2-theta±0.2 degrees 2-theta; an XRPD pattern as depicted in FIG. 29, and combinations thereof.

In one embodiment of the present disclosure, crystalline Form I of Rucaparib Esylate is isolated.

In another aspect, the present disclosure relates to a crystalline form of Rucaparib Esylate, designated Form II. The crystalline Form II of Rucaparib Esylate may be characterized by data selected from one or more of the following: an X-ray powder diffraction pattern substantially as depicted in FIG. 30; an X-ray powder diffraction pattern having peaks at 7.9, 13.1, 13.3, 14.9, 15.0 and 18.3 degrees 2-theta±0.2 degrees 2-theta, and combinations of these data.

Crystalline Form II of Rucaparib Esylate may be further characterized by an X-ray powder diffraction pattern having peaks at 7.9, 13.1, 13.3, 14.9, 15.0 and 18.3 degrees 2-theta±0.2 degrees 2-theta and also having any one, two, three, or four additional peaks selected from the group consisting of 20.6, 21.0, 23.6, and 35.1 degrees 2-theta±0.2 degrees 2-theta.

Figure 30:
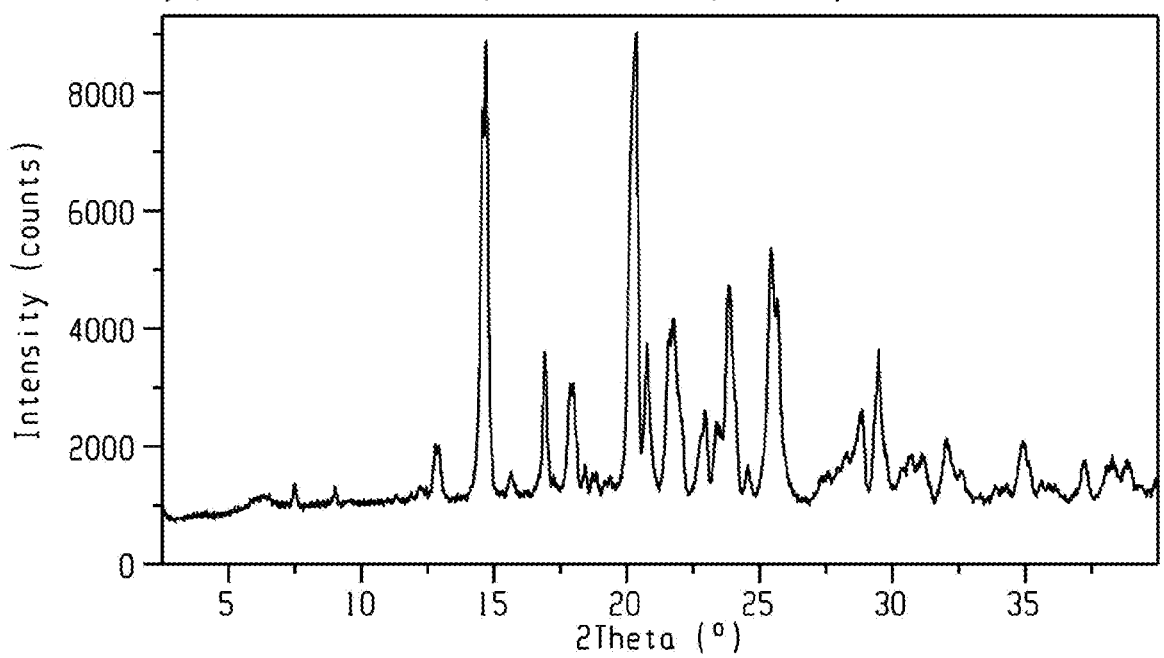
FIG. 30 shows a characteristic X-ray powder diffraction pattern of Rucaparib Esylate Form II.

Crystalline Form II of Rucaparib Esylate may be characterized by each of the above characteristics alone/or by all possible combinations, e.g., an XRPD pattern having peaks at 7.9, 13.1, 13.3, 14.9, 15.0 and 18.3 degrees 2-theta±0.2 degrees 2-theta; an XRPD pattern as depicted in FIG. 30, and combinations thereof.

In one embodiment of the present disclosure, crystalline Form II of Rucaparib Esylate is isolated.

In another aspect, the present disclosure relates to a crystalline form of Rucaparib Esylate, designated Form III. The crystalline Form III of Rucaparib Esylate may be characterized by data selected from one or more of the following: an X-ray powder diffraction pattern substantially as depicted in FIG. 31; an X-ray powder diffraction pattern having peaks at 14.8, 16.8, 19.3, 23.3 and 23.6 degrees 2-theta±0.2 degrees 2-theta, and combinations of these data.

Crystalline Form III of Rucaparib Esylate may be further characterized by an X-ray powder diffraction pattern having peaks at 14.8, 16.8, 19.3, 23.3 and 23.6 degrees 2-theta±0.2 degrees 2-theta and also having any one, two, three, four or five additional peaks selected from the group consisting of 14.1, 20.4, 21.4, 25.4 and 27.1 degrees 2-theta±0.2 degrees 2-theta.

Figure 31:
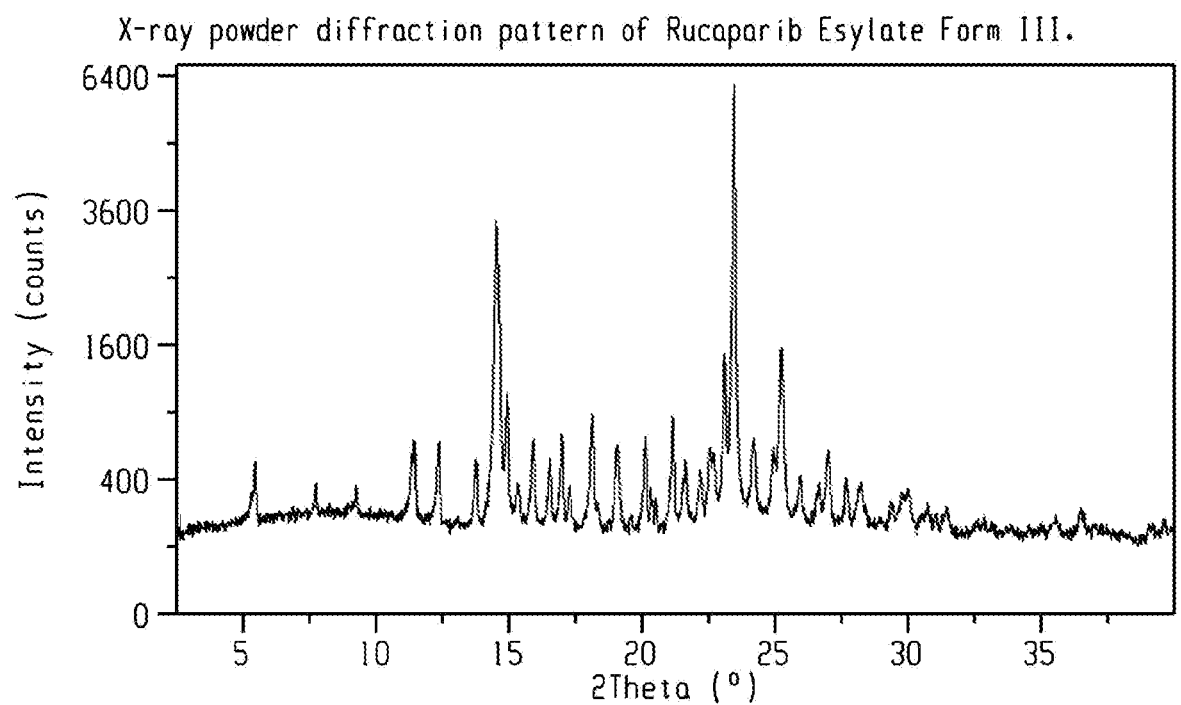
FIG. 31 shows a characteristic X-ray powder diffraction pattern of Rucaparib Esylate Form III.

Crystalline Form III of Rucaparib Esylate may be characterized by each of the above characteristics alone/or by all possible combinations, e.g., an XRPD pattern having peaks at 14.8, 16.8, 19.3, 23.3 and 23.6 degrees 2-theta±0.2 degrees 2-theta; an XRPD pattern as depicted in FIG. 31, and combinations thereof.

In one embodiment of the present disclosure, crystalline Form III of Rucaparib Esylate is isolated.

In another aspect, the present disclosure relates to a crystalline form of Rucaparib Esylate, designated Form IV. The crystalline Form IV of Rucaparib Esylate may be characterized by data selected from one or more of the following: an X-ray powder diffraction pattern substantially as depicted in FIG. 32; an X-ray powder diffraction pattern having peaks at 7.5, 8.6, 13.7, 17.2 and 18.0 degrees 2-theta±0.2 degrees 2-theta, and combinations of these data.

Crystalline Form IV of Rucaparib Esylate may be further characterized by an X-ray powder diffraction pattern having peaks at 7.5, 8.6, 13.7, 17.2 and 18.0 degrees 2-theta±0.2 degrees 2-theta and also having any one, two, three, four or five additional peaks selected from the group consisting of 15.6, 16.5, 22.9, 23.6 and 27.7 degrees 2-theta±0.2 degrees 2-theta.

Figure 32:
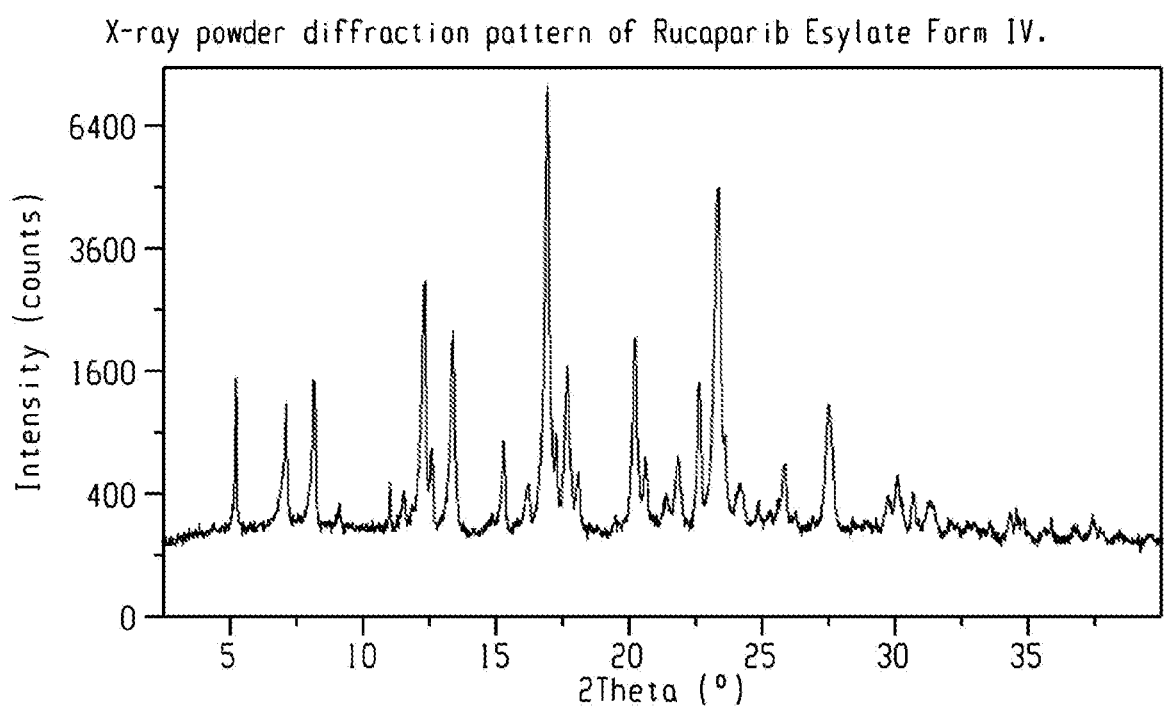
FIG. 32 shows a characteristic X-ray powder diffraction pattern of Rucaparib Esylate Form IV.

Crystalline Form IV of Rucaparib Esylate may be characterized by each of the above characteristics alone/or by all possible combinations, e.g., an XRPD pattern having peaks at 7.5, 8.6, 13.7, 17.2 and 18.0 degrees 2-theta±0.2 degrees 2-theta; an XRPD pattern as depicted in FIG. 32, and combinations thereof.

In one embodiment of the present disclosure, crystalline Form IV of Rucaparib Esylate is isolated.

In another aspect, the present disclosure relates to a crystalline form of Rucaparib Esylate, designated Form V. The crystalline Form V of Rucaparib Esylate may be characterized by data selected from one or more of the following: an X-ray powder diffraction pattern substantially as depicted in FIG. 33; an X-ray powder diffraction pattern having peaks at 12.9, 14.6, 15.9, 18.5 and 24.5 degrees 2-theta±0.2 degrees 2-theta, and combinations of these data.

Crystalline Form V of Rucaparib Esylate may be further characterized by an X-ray powder diffraction pattern having peaks at 12.9, 14.6, 15.9, 18.5 and 24.5 degrees 2-theta±0.2 degrees 2-theta and also having any one, two, three, four or five additional peaks selected from the group consisting of 11.5, 19.7, 20.4, 21.2 and 35.0 degrees 2-theta±0.2 degrees 2-theta.

Figure 33:
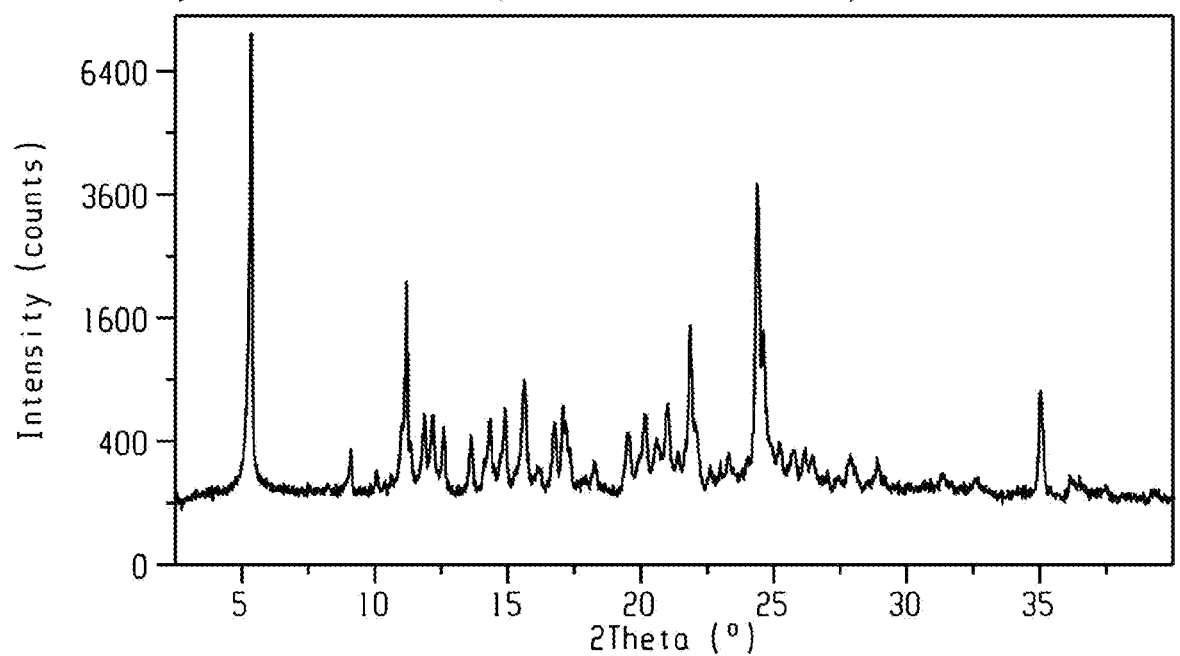
FIG. 33 shows a characteristic X-ray powder diffraction pattern of Rucaparib Esylate Form V.

Crystalline Form V of Rucaparib Esylate may be characterized by each of the above characteristics alone/or by all possible combinations, e.g., an XRPD pattern having peaks at 12.9, 14.6, 15.9, 18.5 and 24.5 degrees 2-theta±0.2 degrees 2-theta; an XRPD pattern as depicted in FIG. 33, and combinations thereof.

In one embodiment of the present disclosure, crystalline Form V of Rucaparib Esylate is isolated.

In another aspect, the present disclosure relates to a crystalline form of Rucaparib Esylate, designated Form VI.

Figure 33A:
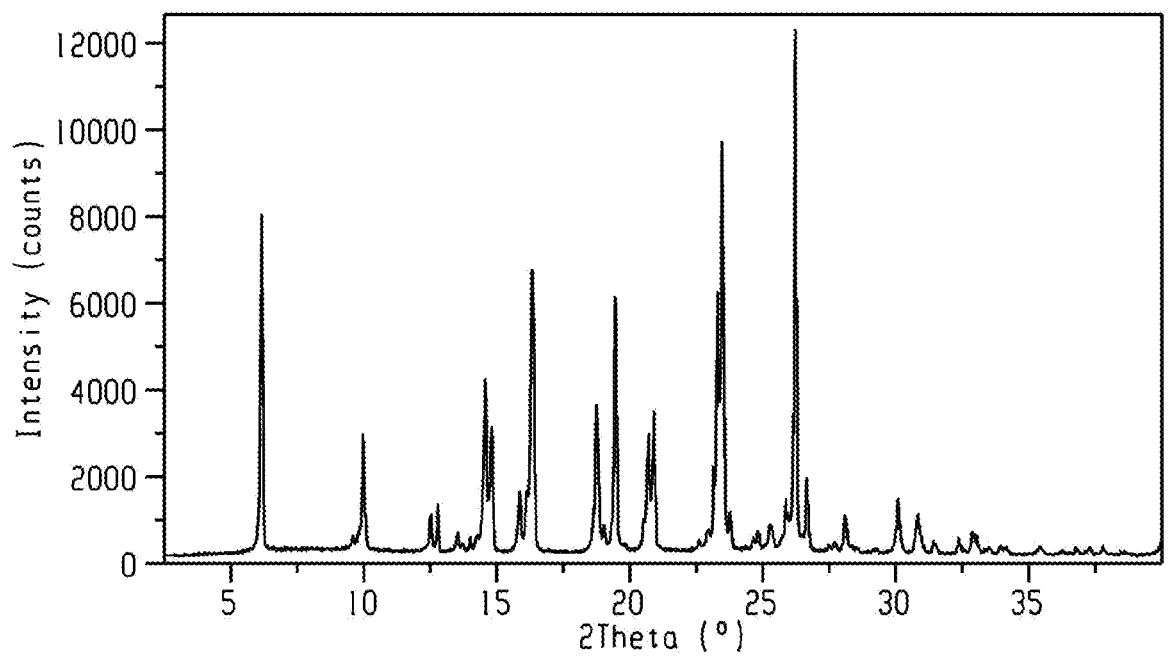
FIG. 33A shows a characteristic X-ray powder diffraction pattern of Rucaparib Esylate Form VI.

The crystalline Form VI of Rucaparib Esylate may be characterized by data selected from one or more of the following: an X-ray powder diffraction pattern substantially as depicted in FIG. 33A; an X-ray powder diffraction pattern having peaks at 6.6, 10.4, 16.6, 19.0 and 19.7 degrees 2-theta±0.2 degrees 2-theta, and combinations of these data.

Crystalline Form VI of Rucaparib Esylate may be further characterized by an X-ray powder diffraction pattern having peaks at 6.6, 10.4, 16.6, 19.0 and 19.7 degrees 2-theta±0.2 degrees 2-theta and also having any one, two, three, four or five additional peaks selected from the group consisting of 12.9, 13.1, 14.9, 15.1 and 26.4 degrees 2-theta±0.2 degrees 2-theta.

Crystalline Form VI of Rucaparib Esylate may be characterized by each of the above characteristics alone/or by all possible combinations, e.g., an XRPD pattern having peaks at 6.6, 10.4, 16.6, 19.0 and 19.7 degrees 2-theta±0.2 degrees 2-theta; an XRPD pattern as depicted in FIG. 33A, and combinations thereof.

In one embodiment of the present disclosure, crystalline Form VI of Rucaparib Esylate is isolated.

Figure 50A:
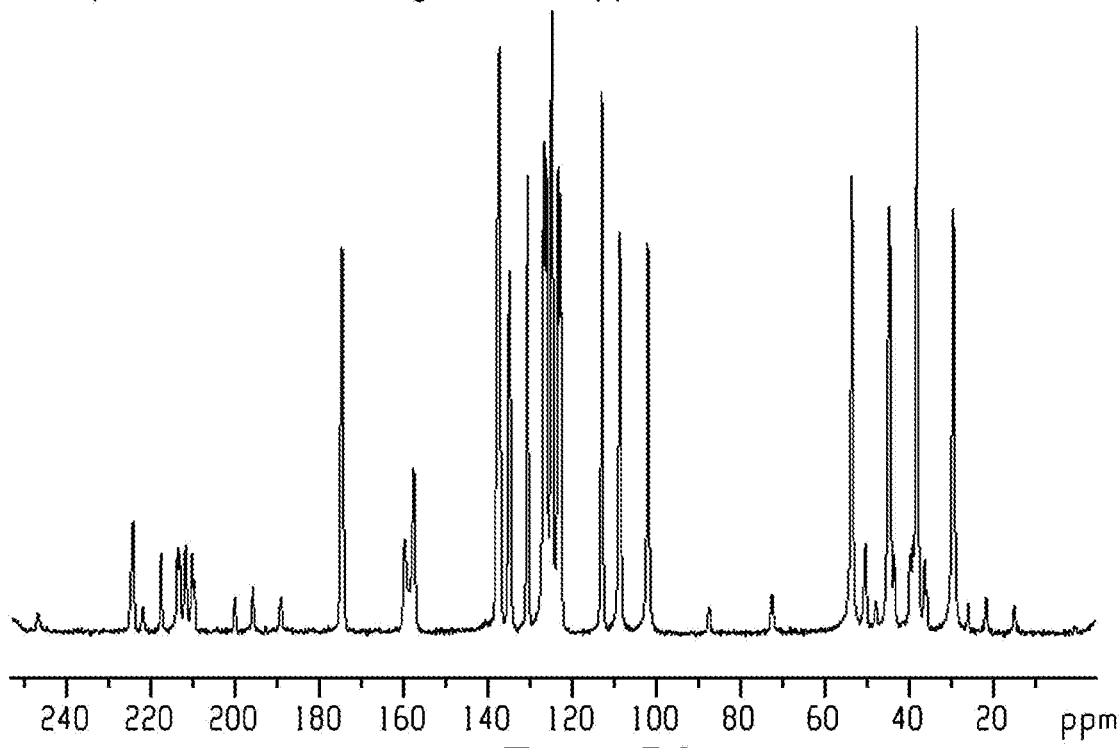
FIG. 50a shows a characteristic solid state $^{13}$C NMR spectrum of Form I of Rucaparib base at the range of 250-0 ppm.
Figure 50B:
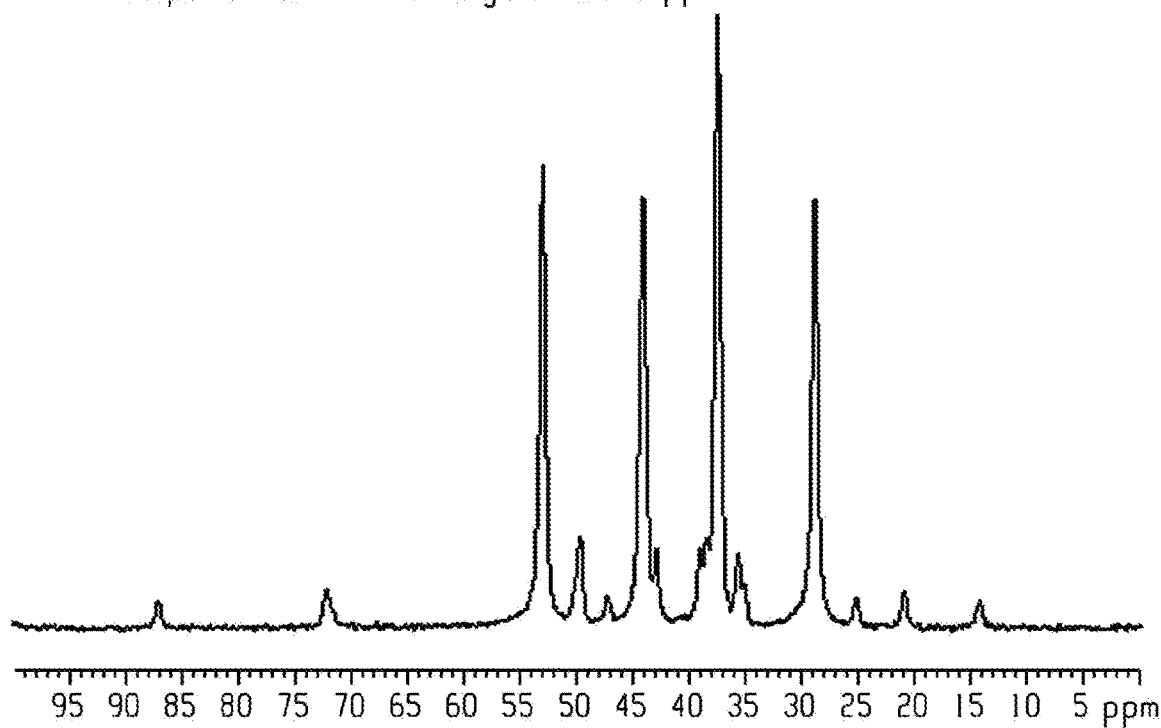
FIG. 50b shows a characteristic solid state $^{13}$C NMR spectrum of Form I of Rucaparib base at the range of 100-0 ppm.
Figure 50C:
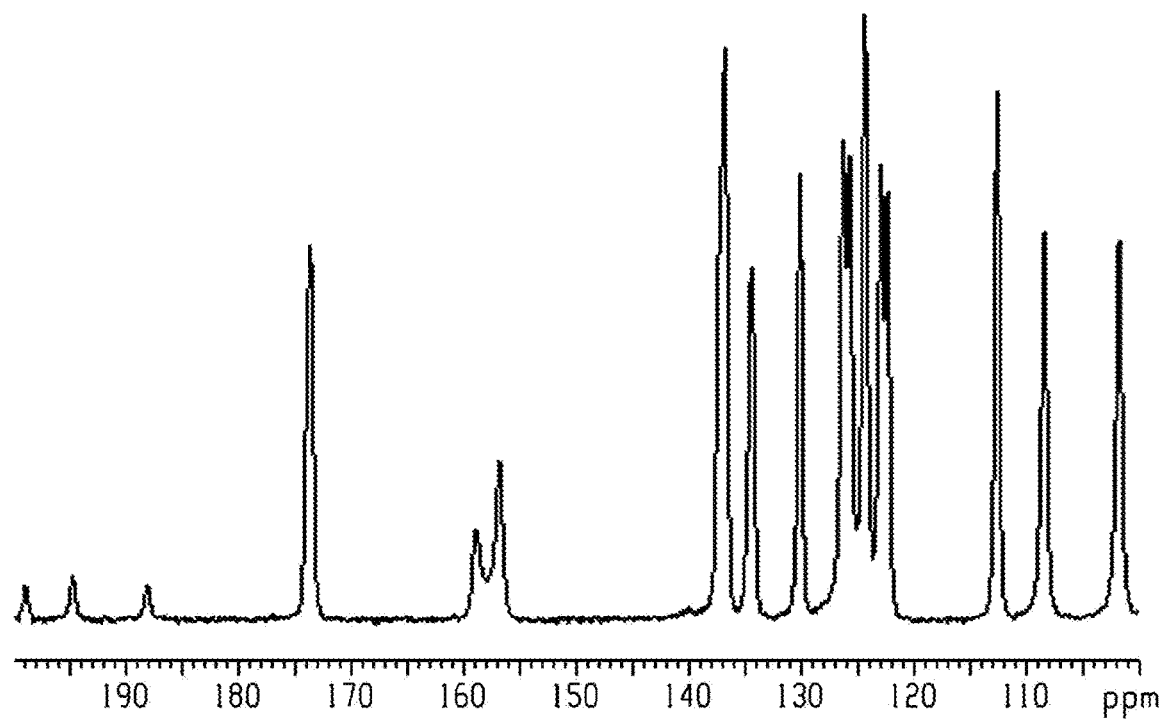
FIG. 50c shows a characteristic solid state $^{13}$C NMR spectrum of Form I of Rucaparib base at the range of 200-100 ppm.

The present disclosure further comprises a crystalline form of Rucaparib base, designated Form I. The crystalline Form I of Rucaparib base may be characterized by data selected from one or more of the following: an X-ray powder diffraction pattern substantially as depicted in FIG. 34; an X-ray powder diffraction pattern having peaks at 9.2, 15.2, 17.2, 21.0 and 23.1 degrees 2-theta±0.2 degrees 2-theta; a solid state $^{13}$C NMR spectrum having characteristic peaks at 123.0, 126.4 and 159.4 ppm±0.2 ppm; a solid state $^{13}$C NMR spectrum having the following chemical shift absolute differences from a reference peak at 108.3 ppm±2 ppm: 14.7, 18.1 and 51.1 ppm±0.1 ppm; and a solid state $^{13}$C NMR spectrum as depicted in FIG. 50a or 50b or 50c; and combinations of these data.

Crystalline Form I of Rucaparib base may be further characterized by an X-ray powder diffraction pattern having peaks as described above and also having any one, two or three additional peaks selected from the group consisting of 20.0, 24.1 and 28.4±0.2 degrees 2-theta±0.2 degrees 2-theta.

Figure 34:
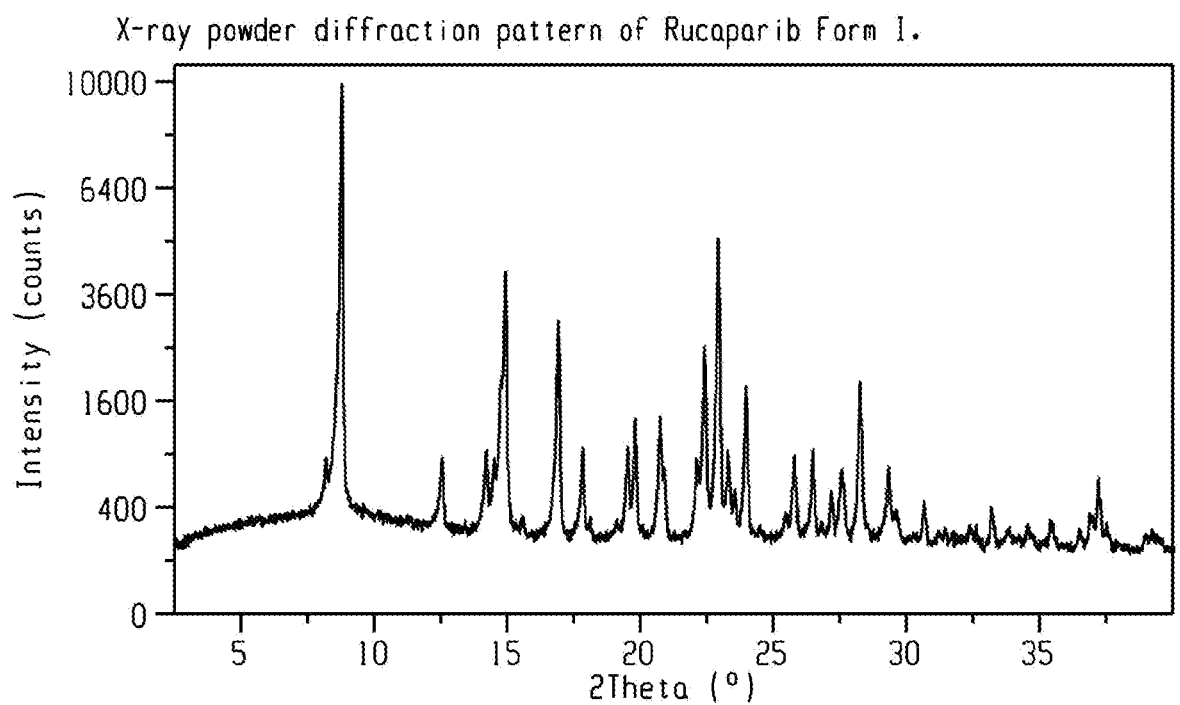
FIG. 34 shows a characteristic X-ray powder diffraction pattern of Form I of Rucaparib base.

Crystalline Form I of Rucaparib base may be characterized by each of the above characteristics alone/or by all possible combinations, e.g., an XRPD pattern having peaks at 9.2, 15.2, 17.2, 21.0 and 23.1 degrees 2-theta±0.2 degrees 2-theta; an XRPD pattern as depicted in FIG. 34, and combinations thereof.

Crystalline Form I of Rucaparib base may be a monohydrate.

In one embodiment of the present disclosure, Form I of Rucaparib base is isolated.

In particular embodiment, Form I of Rucaparib base is polymorphically pure. i.e. Form I (as described in any of the embodiments disclosed herein) which is substantially free of any other solid state (or polymorphic) forms. The term polymorphically pure is defined herein above. Particularly, polymorphically pure form I of Rucaparib base contains about 20% or less, about 10% or less, about 5% or less, about 2% or less, about 1% or less, or 0% of crystalline Form II of Rucaparib base form $X_1$ and/or $X_2$, which is defined herein above. Thus, crystalline Form I of Rucaparib base described herein contains greater than about 80% (w/w), greater than about 90% (w/w), greater than about 95% (w/w), greater than about 98% (w/w), greater than about 99% (w/w), or about 100% of Crystalline Form I of Rucaparib base. Accordingly, in some embodiments of the disclosure, Crystalline Form I of Rucaparib base may contain from about 1% to about 20% (w/w), from about 5% to about 20% (w/w), or from about 5% to about 10% (w/w) of Crystalline form $X_1$ and/or $X_2$ of Rucaparib base.

Typically, the amount of crystalline form $X_1$ and/or $X_2$ of Rucaparib base in Rucaparib base form I can be measured and/or quantified by PXRD using the peaks defined herein above.

Crystalline Form I of Rucaparib base may have advantageous properties, as detailed above. Particularly, Crystalline Form I of Rucaparib base has no API mass increase while Rucaparib camsylate possess API mass increase of 72%. This is extremely important for a high drug loading treatment, and may contribute to compressibility of the API and to producing smaller tablet size. In addition, Crystalline Form I of Rucaparib base is non-hygroscopic; it is stable for a period of at least 1 month at 20-100% relative humidity (RH) at room temperature (RT) in open Petri dish; and it has improved kinetic solubility at various pH ranges.

Figure 51A:
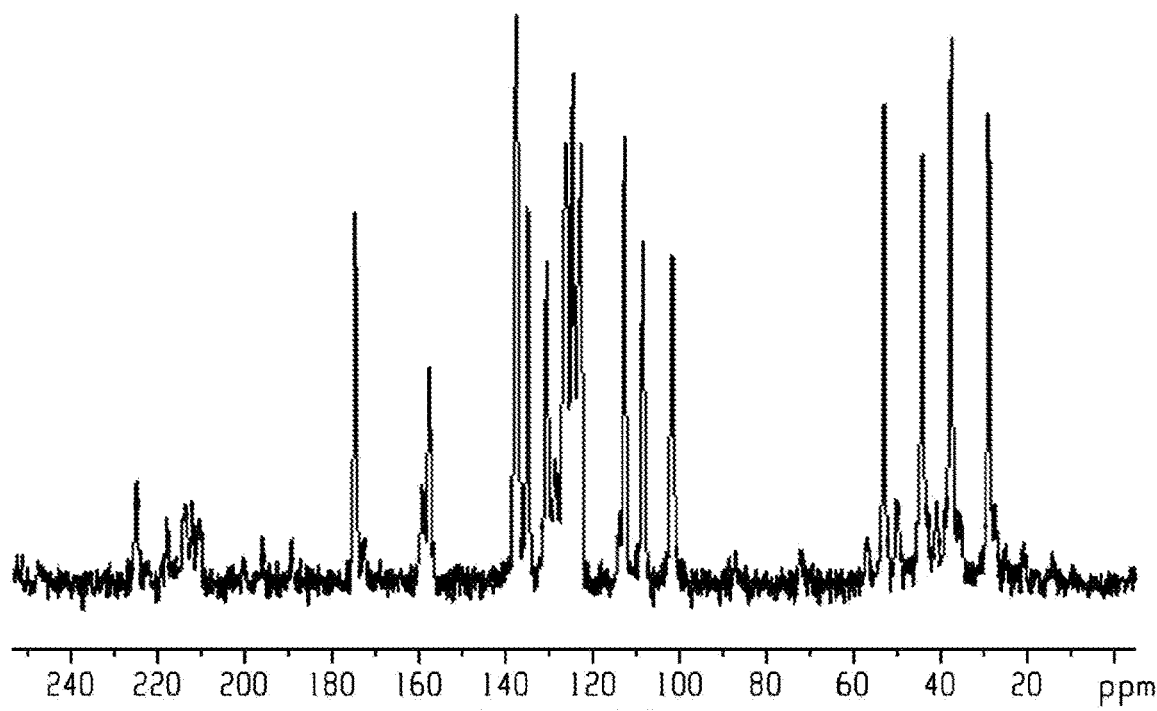
FIG. 51a shows a characteristic solid state $^{13}$C NMR spectrum of Form II of Rucaparib base at the range of 265-0 ppm.
Figure 51B:
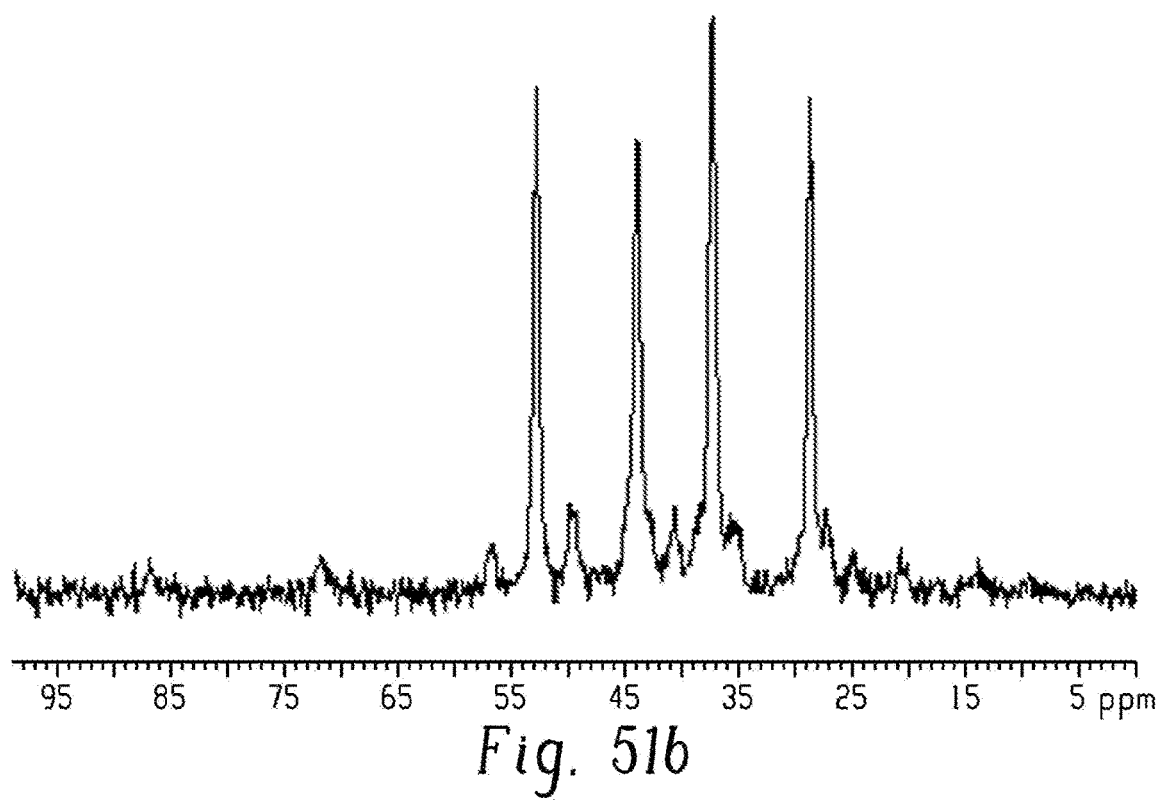
FIG. 51b shows a characteristic solid state $^{13}$C NMR spectrum of Form II of Rucaparib base at the range of 100-0 ppm.
Figure 51C:
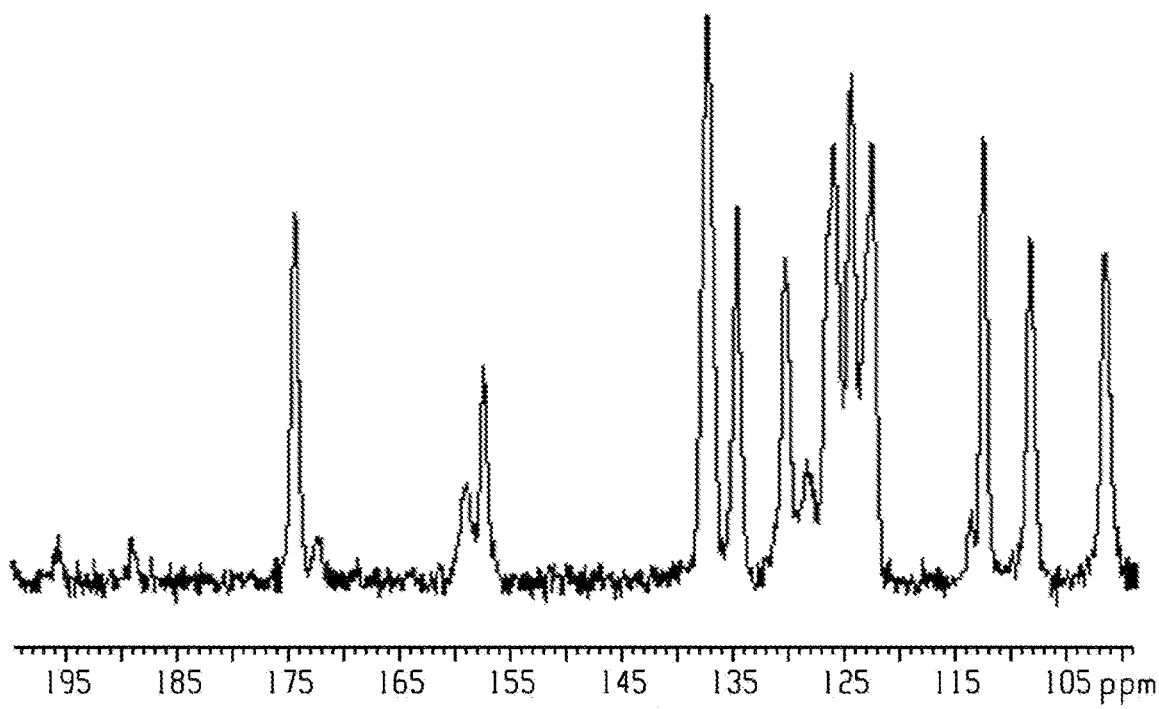
FIG. 51c shows a characteristic solid state $^{13}$C NMR spectrum of Form II of Rucaparib base at the range of 200-100 ppm.

In another aspect, the present disclosure relates to a crystalline form of Rucaparib base, designated Form II. The crystalline Form II of Rucaparib base may be characterized by data selected from one or more of the following: an X-ray powder diffraction pattern substantially as depicted in FIG. 35 or 36; an X-ray powder diffraction pattern having peaks at 12.0, 14.4, 16.8, 18.8 and 24.3 degrees 2-theta±0.2 degrees 2-theta, a solid state $^{13}$C NMR spectrum having characteristic peaks at 113.6, 122.6, 126.0, 128.4, 137.3 and 159.0 ppm±0.2 ppm; a solid state $^{13}$C NMR spectrum having the following chemical shift absolute differences from a reference peak at 108.3 ppm±2 ppm: 5.3, 14.3, 17.7, 20.1, 29.0 and 50.7 ppm±0.1 ppm; and a solid state $^{13}$C NMR spectrum as depicted in FIG. 51a or 51b or 51c; and combinations of these data.

Crystalline Form II of Rucaparib base may be further characterized by an X-ray powder diffraction pattern having peaks as described above and also having any one, two, three, four or five additional peaks selected from the group consisting of 20.2, 22.5, 29.8, 30.2 and 30.6 degrees 2-theta±0.2 degrees 2-theta.

Figure 35:
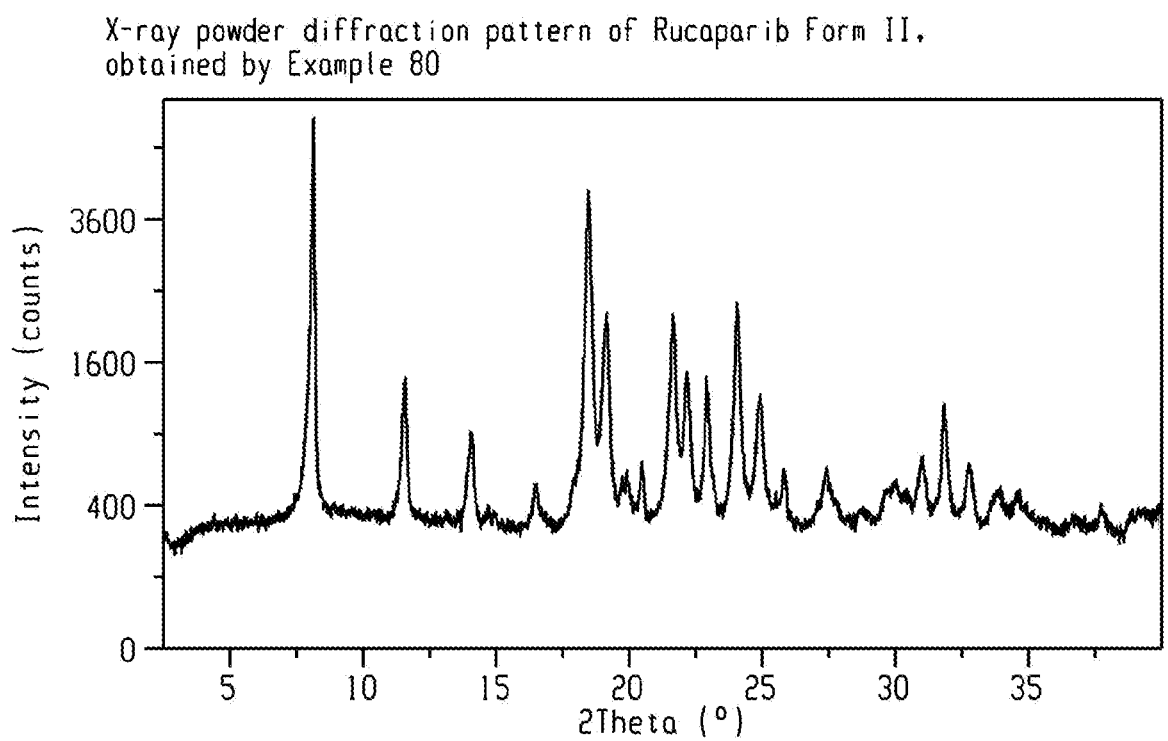
FIG. 35 shows a characteristic X-ray powder diffraction pattern of Form II of Rucaparib base obtained by Example 80.
Figure 36:
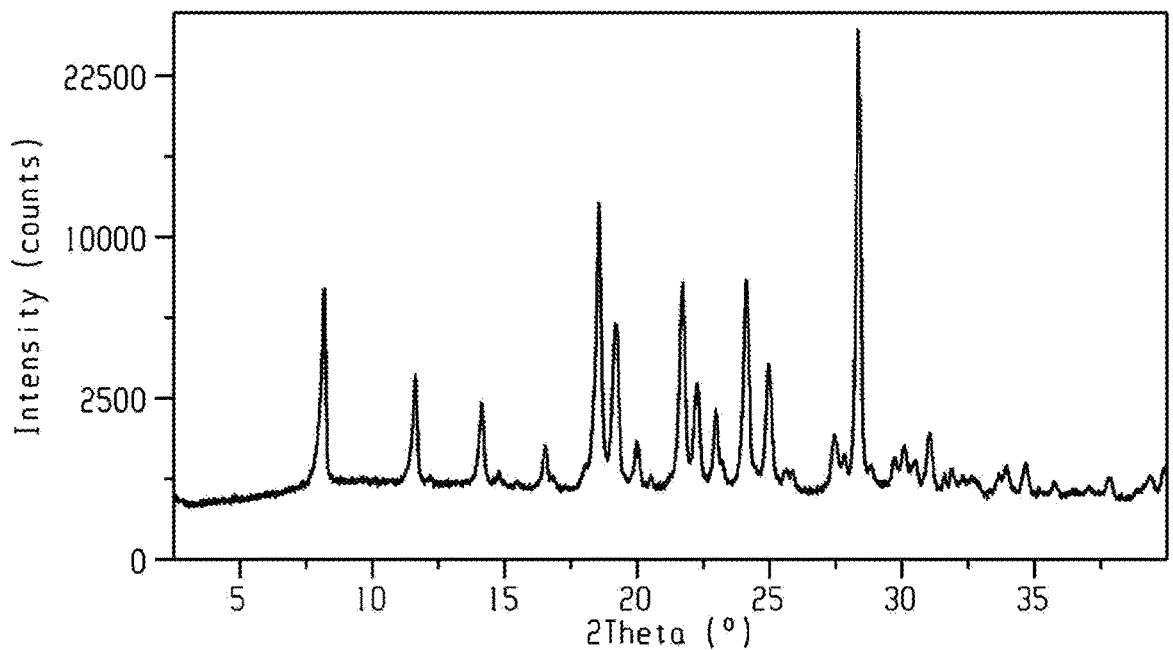
FIG. 36 shows an X-ray powder diffraction pattern of Form II of Rucaparib base obtained by Example 82.

Crystalline Form II of Rucaparib base may be characterized by each of the above characteristics alone/or by all possible combinations, e.g., an XRPD pattern having peaks at 12.0, 14.4, 16.8, 18.8 and 24.3 degrees 2-theta±0.2 degrees 2-theta; an XRPD pattern as depicted in FIGS. 35 and 36, and combinations thereof.

Crystalline Form II of Rucaparib base may be anhydrous.

In one embodiment of the present disclosure, Form II of Rucaparib base is isolated.

In particular embodiment, Form II of Rucaparib base is polymorphically pure. i.e. Form II (as described in any of the embodiments disclosed herein) which is substantially free of any other solid state (or polymorphic) forms. The term polymorphically is defined herein above. Particularly, polymorphically pure form II of Rucaparib base contains about 20% or less, about 10% or less, about 5% or less, about 2% or less, about 1% or less, or 0% of crystalline Form II of Rucaparib base form $X_1$ and/or $X_2$, which is defined herein above. Thus, crystalline Form II of Rucaparib base described herein contains greater than about 80% (w/w), greater than about 90% (w/w), greater than about 95% (w/w), greater than about 98% (w/w), greater than about 99% (w/w), or about 100% of Crystalline Form II of Rucaparib base. Accordingly, in some embodiments of the disclosure, Crystalline Form II of Rucaparib base may contain from about 1% to about 20% (w/w), from about 5% to about 20% (w/w), or from about 5% to about 10% (w/w) of Crystalline form $X_1$ and/or $X_2$ of Rucaparib base.

Typically, the amount of crystalline form $X_1$ and/or $X_2$ of Rucaparib base in Rucaparib base form II can be measured and/or quantified by PXRD using the peaks defined herein above.

Crystalline Form II of Rucaparib base may have advantageous properties, as detailed above. Particularly, Crystalline Form II of Rucaparib base no API mass increase while Rucaparib camsylate possess API mass increase of 72%. This is extremely important for a high drug loading treatment, and may contribute to compressibility of the API and to producing smaller tablet size. In addition, Crystalline Form II of Rucaparib base is stable for a period of at least 1 month at 20-40% relative humidity (RH) at room temperature (RT) in open Petri dish.

In another aspect, the present disclosure relates to a crystalline form of Rucaparib base, designated Form III. This crystalline form of Rucaparib base may be characterized by an X-ray powder diffraction pattern having peaks at 15.4, 17.5, 18.6, 20.6, and 21.3 degrees 2-theta±0.2 degrees 2-theta.

Form III may be further characterized by an X-ray powder diffraction pattern having peaks as described above and also having any one or two additional peaks selected from the group consisting of 24.1 and 24.5 degrees 2-theta±0.2 degrees 2-theta.

In another aspect, the present disclosure relates to a crystalline form of Rucaparib base, designated Form A. The crystalline Form A of Rucaparib base may be characterized by data selected from one or more of the following: an X-ray powder diffraction pattern substantially as depicted in FIG. 38; an X-ray powder diffraction pattern having peaks at 12.9, 14.2, 14.9, 18.2 and 25.8 degrees 2-theta±0.2 degrees 2-theta, and combinations of these data.

Crystalline Form A of Rucaparib base may be further characterized by an X-ray powder diffraction pattern having peaks as described above and also having any one, two, three, four or five additional peaks selected from the group consisting of 20.7, 21.2, 22.1, 22.3 and 25.1 degrees 2-theta±0.2 degrees 2-theta.

Figure 38:
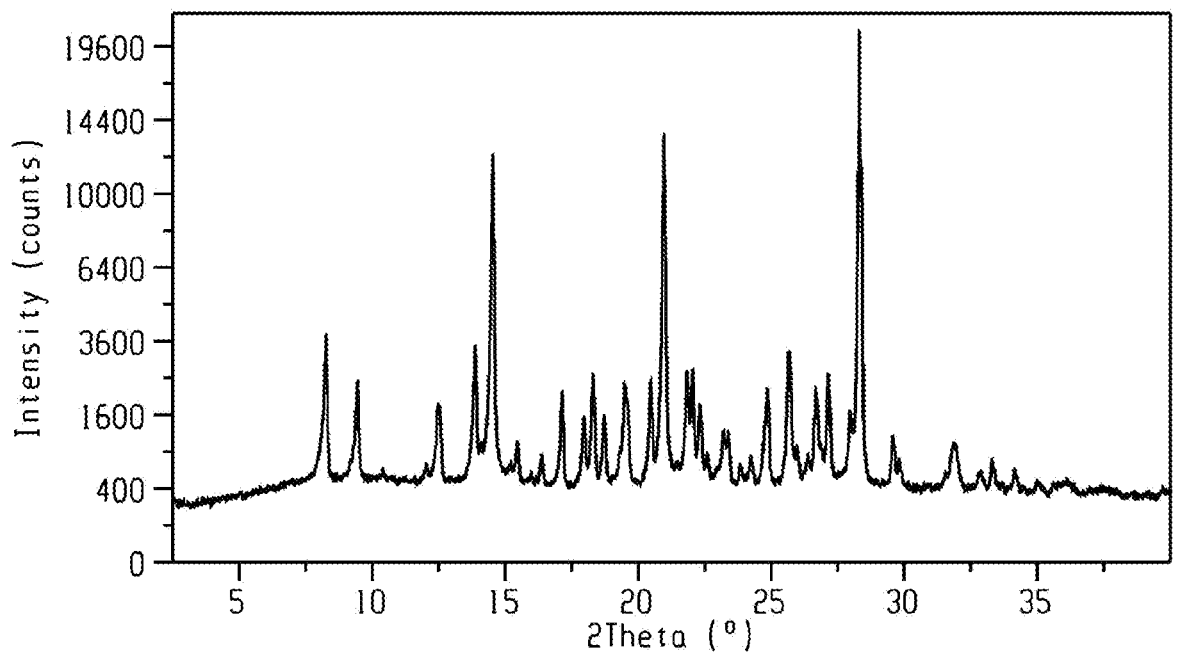
FIG. 38 shows a characteristic X-ray powder diffraction pattern of Form A of Rucaparib base.

Crystalline Form A of Rucaparib base may be characterized by each of the above characteristics alone/or by all possible combinations, e.g., an XRPD pattern having peaks at 12.9, 14.2, 14.9, 18.2 and 25.8 degrees 2-theta±0.2 degrees 2-theta; an XRPD pattern as depicted in FIG. 38, and combinations thereof.

In one embodiment of the present disclosure, Form A of Rucaparib base is isolated.

In another aspect, the present disclosure relates to a crystalline form of Rucaparib base, designated Form C. The crystalline Form C of Rucaparib base may be characterized by data selected from one or more of the following: an X-ray powder diffraction pattern substantially as depicted in FIG. 39; an X-ray powder diffraction pattern having peaks at 10.5, 16.3, 19.7 and 21.4, and 22.2 degrees 2-theta±0.2 degrees 2-theta, and combinations of these data.

Crystalline Form C of Rucaparib base may be further characterized by an X-ray powder diffraction pattern having peaks as described above and also having any one, two, three, four or five additional peaks selected from the group consisting of 8.8, 15.5, 17.7, 18.4 and 26.7 degrees 2-theta±0.2 degrees 2-theta.

Figure 39:
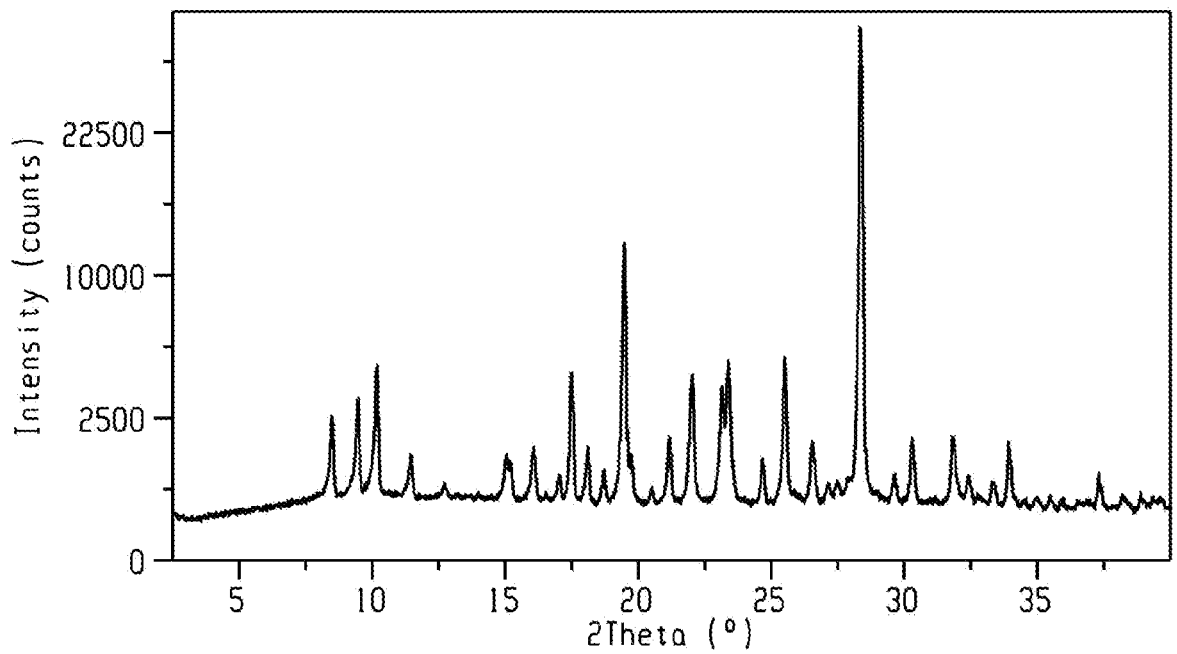
FIG. 39 shows a characteristic X-ray powder diffraction pattern of Form C of Rucaparib base.

Crystalline Form C of Rucaparib base may be characterized by each of the above characteristics alone/or by all possible combinations, e.g., an XRPD pattern having peaks at 10.5, 16.3, 19.7, 21.4 and 22.2 degrees 2-theta±0.2 degrees 2-theta; an XRPD pattern as depicted in FIG. 39, and combinations thereof.

Crystalline Form C of Rucaparib base may be an anhydrous form.

In one embodiment of the present disclosure, Form C of Rucaparib base is isolated.

Crystalline Form C of Rucaparib base may have advantageous properties, as detailed above. Particularly, Crystalline Form C of Rucaparib base has no API mass increase while Rucaparib camsylate possess API mass increase of 72%. This is extremely important for a high drug loading treatment, and may contribute to compressibility of the API and to producing smaller tablet size. In addition, Crystalline Form C of Rucaparib base is non-hygroscopic; it is stable for a period of at least 1 month at 20-100% relative humidity (RH) at room temperature (RT) in open Petri dish; and it has improved kinetic solubility at various pH ranges.

In another aspect, the present disclosure relates to a crystalline form of Rucaparib base, designated Form D. The crystalline Form D of Rucaparib base may be characterized by data selected from one or more of the following: an X-ray powder diffraction pattern substantially as depicted in FIG. 40; an X-ray powder diffraction pattern having peaks at 12.4, 13.1, 21.6, 15.0 and 18.7 degrees 2-theta±0.2 degrees 2-theta, and combinations of these data.

Crystalline Form D of Rucaparib base may be further characterized by an X-ray powder diffraction pattern having peaks as described above and also having any one, two or three additional peaks selected from the group consisting of 14.4, 16.8 and 17.5 degrees 2-theta±0.2 degrees 2-theta.

Figure 40:
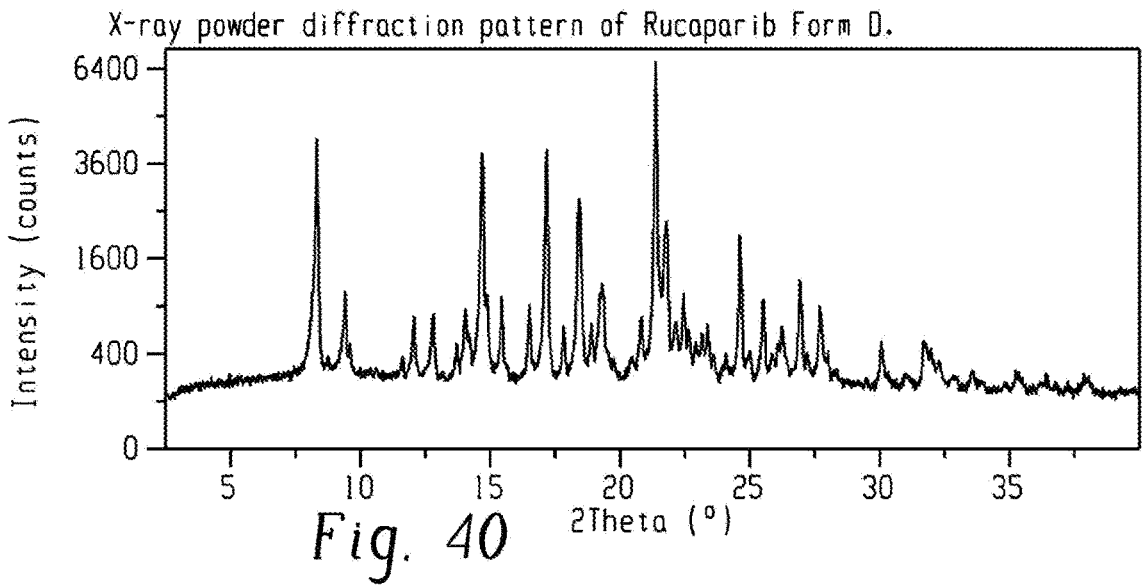
FIG. 40 shows a characteristic X-ray powder diffraction pattern of Form D of Rucaparib base.

Crystalline Form D of Rucaparib base may be characterized by each of the above characteristics alone/or by all possible combinations, e.g., an XRPD pattern having peaks at 12.4, 13.1, 21.6, 15.0 and 18.7 degrees 2-theta±0.2 degrees 2-theta; an XRPD pattern as depicted in FIG. 40, and combinations thereof.

In one embodiment of the present disclosure, Form D of Rucaparib base is isolated.

In another aspect, the present disclosure relates to a crystalline form of Rucaparib base, designated Form F. The crystalline Form F of Rucaparib base may be characterized by data selected from one or more of the following: an X-ray powder diffraction pattern substantially as depicted in FIG. 41; an X-ray powder diffraction pattern having peaks at 6.7, 13.4, 13.8, 16.5 and 20.3 degrees 2-theta±0.2 degrees 2-theta, and combinations of these data.

Crystalline Form F of Rucaparib base may be further characterized by an X-ray powder diffraction pattern having peaks as described above and also having any one, two, three or four additional peaks selected from the group consisting of 10.5, 14.4, 23.9 and 24.1 degrees 2-theta±0.2 degrees 2-theta.

Figure 41:
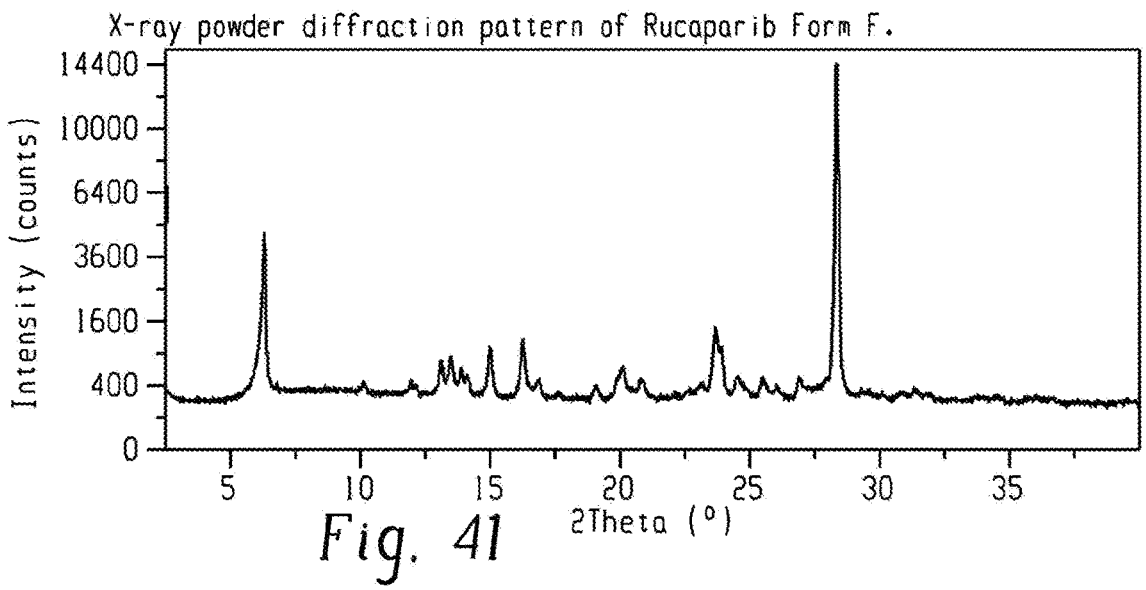
FIG. 41 shows a characteristic X-ray powder diffraction pattern of Form F of Rucaparib base.

Crystalline Form F of Rucaparib base may be characterized by each of the above characteristics alone/or by all possible combinations, e.g., an XRPD pattern having peaks at 6.7, 13.4, 13.8, 16.5 and 20.3 degrees 2-theta±0.2 degrees 2-theta; an XRPD pattern as depicted in FIG. 41, and combinations thereof.

In one embodiment of the present disclosure, Form F of Rucaparib base is isolated.

In another aspect, the present disclosure relates to a crystalline form of Rucaparib base, designated Form J. The crystalline Form J of Rucaparib base may be characterized by data selected from one or more of the following: an X-ray powder diffraction pattern substantially as depicted in FIG. 42; an X-ray powder diffraction pattern having peaks at 10.1, 12.6, 15.4, 17.6 and 18.9 degrees 2-theta±0.2 degrees 2-theta, and combinations of these data.

Crystalline Form J of Rucaparib base may be further characterized by an X-ray powder diffraction pattern having peaks as described above and also having any one, two, three, four or five additional peaks selected from the group consisting of 8.8, 16.0, 19.2, 20.2 and 21.9 degrees 2-theta±0.2 degrees 2-theta.

Figure 42:
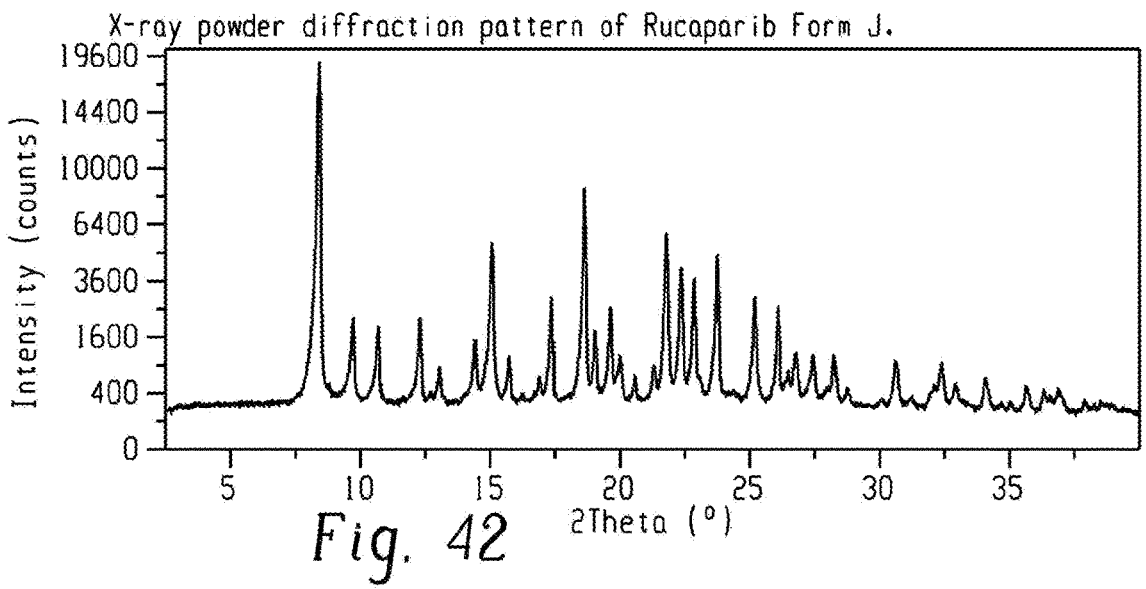
FIG. 42 shows a characteristic X-ray powder diffraction pattern of Form J of Rucaparib base.

Crystalline Form J of Rucaparib base may be characterized by each of the above characteristics alone/or by all possible combinations, e.g., an XRPD pattern having peaks at 10.1, 12.6, 15.4, 17.6 and 18.9 degrees 2-theta±0.2 degrees 2-theta; an XRPD pattern as depicted in FIG. 42, and combinations thereof. In one embodiment of the present disclosure, Form J of Rucaparib base is isolated.

In another aspect, the present disclosure relates to a crystalline form of Rucaparib base, designated Form K. The crystalline Form K of Rucaparib base may be characterized by data selected from one or more of the following: an X-ray powder diffraction pattern substantially as depicted in FIG. 43; an X-ray powder diffraction pattern having peaks at 12.3, 13.2, 14.0, 15.1 and 17.4 degrees 2-theta±0.2 degrees 2-theta, and combinations of these data.

Crystalline Form K of Rucaparib base may be further characterized by an X-ray powder diffraction pattern having peaks as described above and also having any one, two, three, four or five additional peaks selected from the group consisting of 10.9, 21.7, 23.5, 24.6 and 25.5 degrees 2-theta±0.2 degrees 2-theta.

Figure 43:
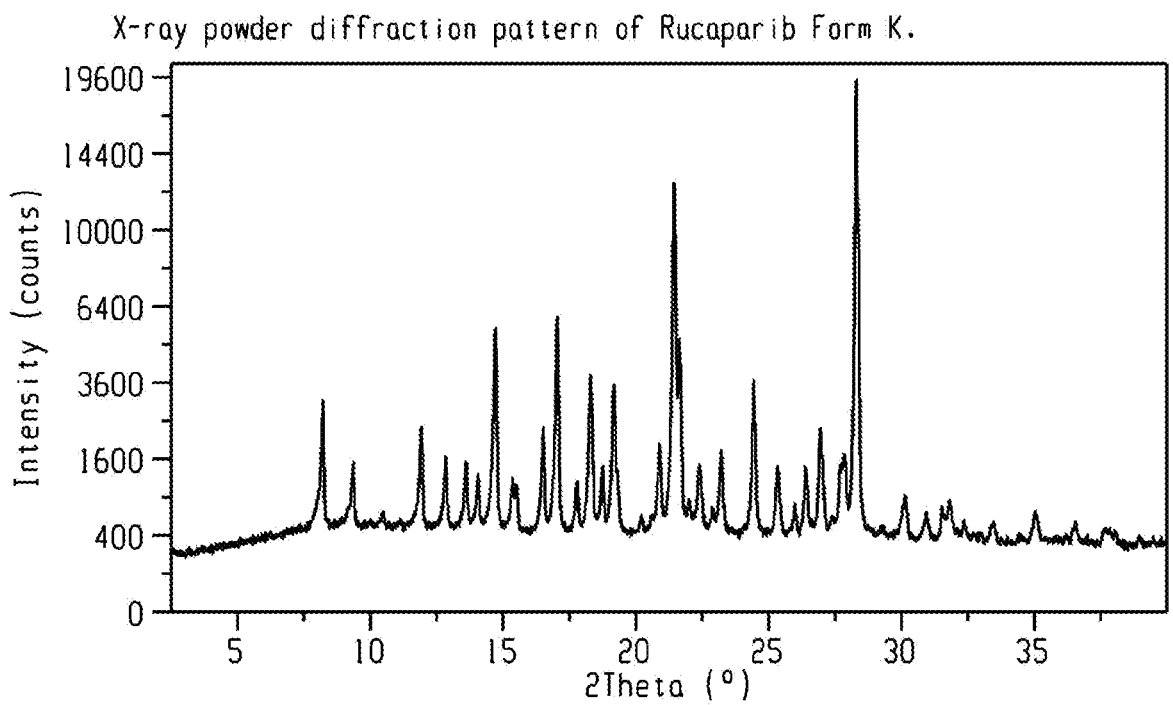
FIG. 43 shows a characteristic X-ray powder diffraction pattern of Form K of Rucaparib base.

Crystalline Form K of Rucaparib base may be characterized by each of the above characteristics alone/or by all possible combinations, e.g., an XRPD pattern having peaks at 12.3, 13.2, 14.0, 15.1 and 17.4 degrees 2-theta±0.2 degrees 2-theta; an XRPD pattern as depicted in FIG. 43, and combinations thereof.

In one embodiment of the present disclosure, Form K of Rucaparib base is isolated.

In another aspect, the present disclosure relates to a crystalline form of Rucaparib base, designated Form L. The crystalline Form L of Rucaparib base may be characterized by data selected from one or more of the following: an X-ray powder diffraction pattern substantially as depicted in FIG. 44; an X-ray powder diffraction pattern having peaks at 7.8, 8.6, 15.7, 20.7 and 23.4 degrees 2-theta±0.2 degrees 2-theta, and combinations of these data.

Crystalline Form L of Rucaparib base may be further characterized by an X-ray powder diffraction pattern having peaks as described above and also having any one, two, three, four or five additional peaks selected from the group consisting of 13.9, 16.4, 17.8, 20.0 and 21.4 degrees 2-theta±0.2 degrees 2-theta.

Figure 44:
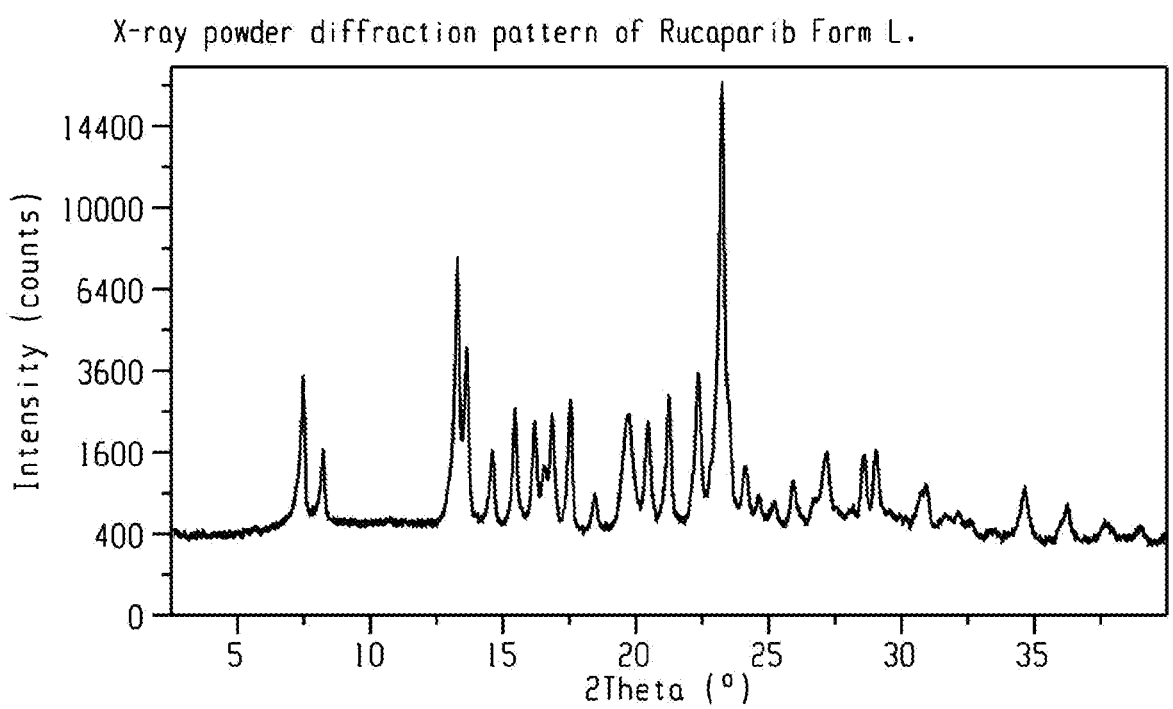
FIG. 44 shows a characteristic X-ray powder diffraction pattern of Form L of Rucaparib base.

Crystalline Form L of Rucaparib base may be characterized by each of the above characteristics alone/or by all possible combinations, e.g., an XRPD pattern having peaks at 7.8, 8.6, 15.7, 20.7 and 23.4 degrees 2-theta±0.2 degrees 2-theta; an XRPD pattern as depicted in FIG. 44, and combinations thereof.

In one embodiment of the present disclosure, Form L of Rucaparib base is isolated.

In another aspect, the present disclosure relates to a crystalline form of Rucaparib base, designated Form M. The crystalline Form M of Rucaparib base may be characterized by data selected from one or more of the following: an X-ray powder diffraction pattern substantially as depicted in FIG. 45; an X-ray powder diffraction pattern having peaks at 7.3, 8.1, 9.5, 12.2 and 18.5 degrees 2-theta±0.2 degrees 2-theta, and combinations of these data.

Crystalline Form M of Rucaparib base may be further characterized by an X-ray powder diffraction pattern having peaks as described above and also having any one, two, three, four or five additional peaks selected from the group consisting of 14.6, 16.2, 21.5, 24.6 and 28.6 degrees 2-theta±0.2 degrees 2-theta.

Figure 45:
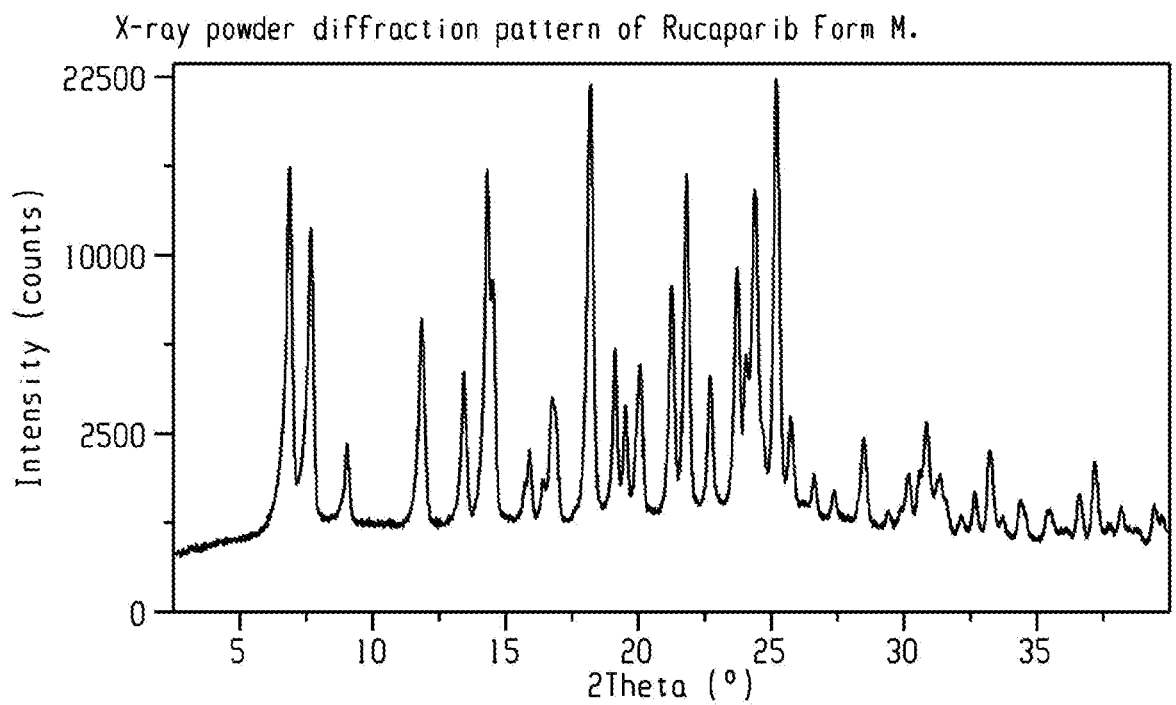
FIG. 45 shows a characteristic X-ray powder diffraction pattern of Form M of Rucaparib base.

Crystalline Form M of Rucaparib base may be characterized by each of the above characteristics alone/or by all possible combinations, e.g., an XRPD pattern having peaks at 7.3, 8.1, 9.5, 12.2 and 18.5 degrees 2-theta±0.2 degrees 2-theta; an XRPD pattern as depicted in FIG. 45, and combinations thereof.

In one embodiment of the present disclosure, Form M of Rucaparib base is isolated.

The present disclosure also relates to solid state forms of Rucaparib S-Camsylate.

In another aspect, the present disclosure relates to a crystalline form of Rucaparib S-Camsylate, designated Form Alpha. The crystalline Form Alpha of Rucaparib S-Camsylate may be characterized by data selected from one or more of the following: an X-ray powder diffraction pattern substantially as depicted in FIG. 46; an X-ray powder diffraction pattern having peaks at 6.0, 6.9, 11.0, 12.1, 13.3 and 18.2 degrees 2-theta±0.2 degrees 2-theta, and combinations of these data.

Crystalline Form Alpha of Rucaparib S-Camsylate may be further characterized by an X-ray powder diffraction pattern having peaks as described above and also having any one, two, three, four or five additional peaks selected from the group consisting of 13.9, 16.3, 19.3, 22.0 and 30.5 degrees 2-theta±0.2 degrees 2-theta.

Figure 46:
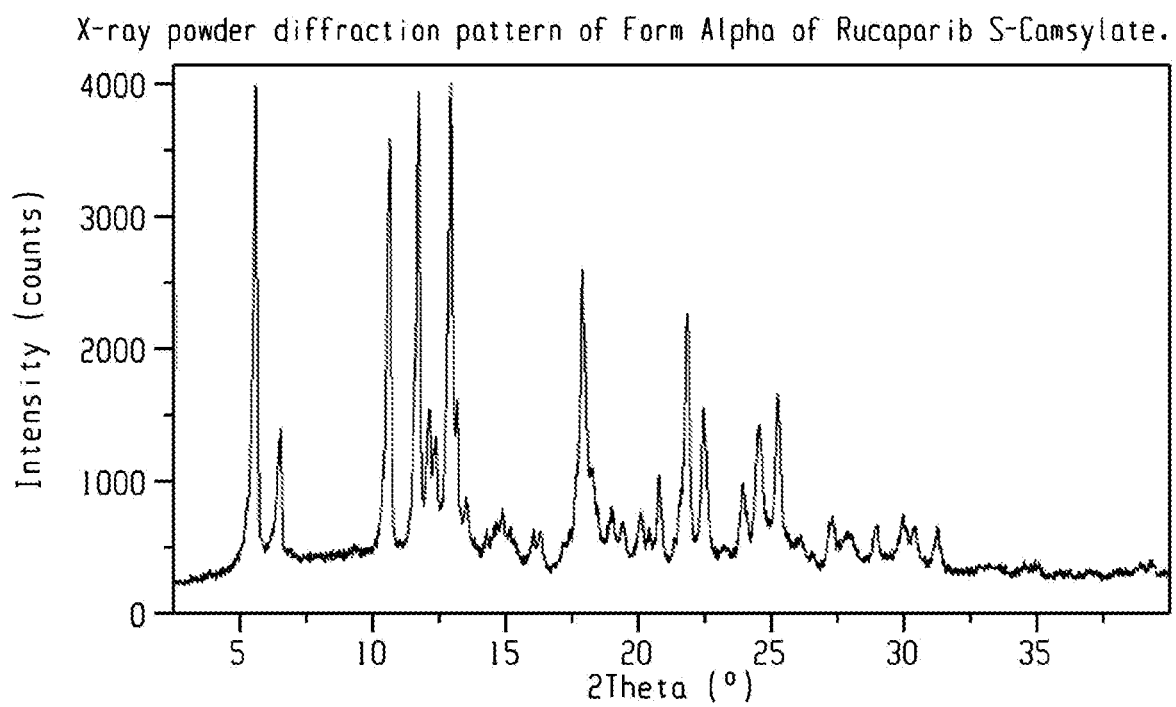
FIG. 46 shows a characteristic X-ray powder diffraction pattern of Form Alpha of Rucaparib S-Camsylate.

Crystalline Form Alpha of Rucaparib S-Camsylate may be characterized by each of the above characteristics alone/or by all possible combinations, e.g., an XRPD pattern having peaks at 6.0, 6.9, 11.0, 12.1, 13.3 and 18.2 degrees 2-theta±0.2 degrees 2-theta; an XRPD pattern as depicted in FIG. 46, and combinations thereof.

In one embodiment of the present disclosure, Form Alpha of Rucaparib S-Camsylate is isolated.

Figure 47:
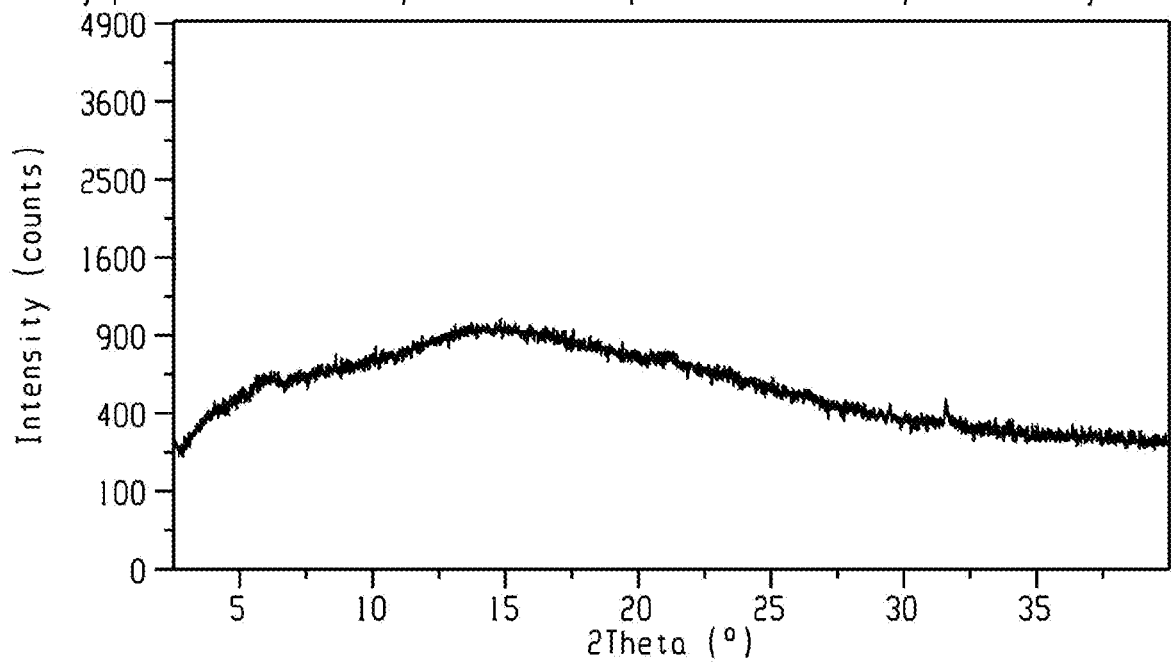
FIG. 47 shows a characteristic X-ray powder diffraction pattern of Amorphous form of Rucaparib S-Camsylate.

In another aspect, the present disclosure comprises an Amorphous Form of Rucaparib S-Camsylate. The Amorphous Form of Rucaparib S-Camsylate may be characterized by X-ray powder diffraction pattern substantially as depicted in FIG. 47.

In one embodiment of the present disclosure, the Amorphous Form of Rucaparib S-Camsylate is isolated.

In another aspect, the present disclosure relates to a crystalline form of Rucaparib S-Camsylate, designated Form Beta. The crystalline Form Beta of Rucaparib S-Camsylate may be characterized by data selected from one or more of the following: an X-ray powder diffraction pattern substantially as depicted in FIG. 48; an X-ray powder diffraction pattern having peaks at 11.9, 14.0, 15.1, 21.6, and 23.1 degrees 2-theta±0.2 degrees 2-theta, and combinations of these data.

Crystalline Form Beta of Rucaparib S-Camsylate may be further characterized by an X-ray powder diffraction pattern having peaks as described above and also having any one, two, three, four or five additional peaks selected from the group consisting of 7.5, 10.8, 13.9, 17.8, and 20.8 degrees 2-theta±0.2 degrees 2-theta.

Figure 48:
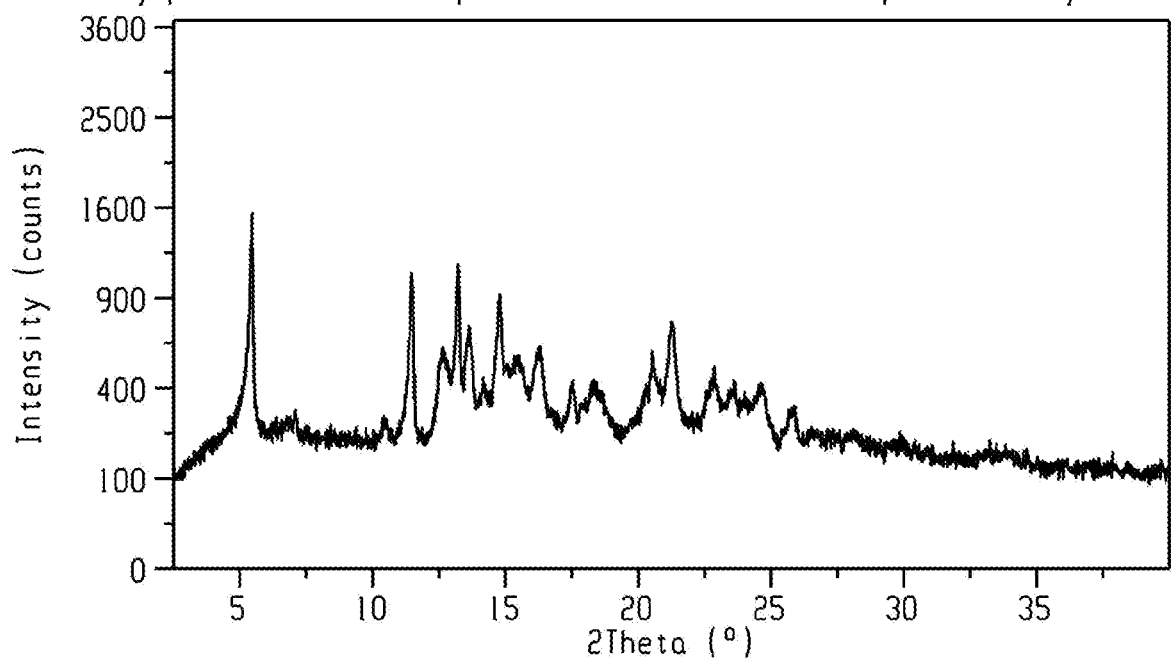
FIG. 48 shows a characteristic X-ray powder diffraction pattern of Form Beta of Rucaparib S-Camsylate.

Crystalline Form Beta of Rucaparib S-Camsylate may be characterized by each of the above characteristics alone/or by all possible combinations, e.g., an XRPD pattern having peaks at 11.9, 14.0, 15.1, 21.6 and 23.1 degrees 2-theta±0.2 degrees 2-theta; an XRPD pattern as depicted in FIG. 48, and combinations thereof.

In one embodiment of the present disclosure, Form Beta of Rucaparib S-Camsylate is isolated.

In another aspect, the present disclosure relates to a crystalline form of Rucaparib S-Camsylate, designated Form Gamma. The crystalline Form Gamma of Rucaparib S-Camsylate may be characterized by data selected from one or more of the following: an X-ray powder diffraction pattern substantially as depicted in FIG. 49; an X-ray powder diffraction pattern having peaks at 11.9, 12.9, 14.0, and 15.1 degrees 2-theta±0.2 degrees 2-theta, and combinations of these data.

Crystalline Form Gamma of Rucaparib S-Camsylate may be further characterized by an X-ray powder diffraction pattern having peaks at 11.9, 12.9, 14.0, and 15.1 degrees 2-theta±0.2 degrees 2-theta and also having any one or two additional peaks selected from the group consisting of 17.9 and 20.6 degrees 2-theta±0.2 degrees 2-theta.

Figure 49:
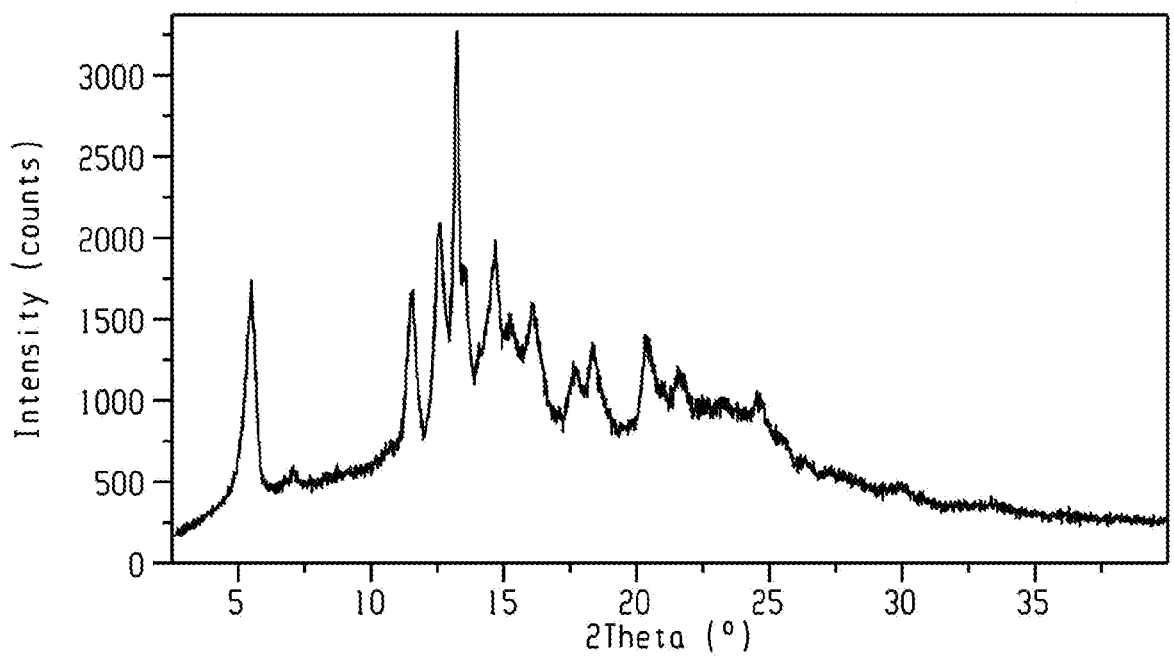
FIG. 49 shows a characteristic X-ray powder diffraction pattern of Form Gamma of Rucaparib S-Camsylate.

Crystalline Form Gamma of Rucaparib S-Camsylate may be characterized by each of the above characteristics alone/ or by all possible combinations, e.g., an XRPD pattern having peaks at 11.9, 12.9, 14.0, and 15.1 degrees 2-theta±0.2 degrees 2-theta; an XRPD pattern as depicted in FIG. 49, and combinations thereof.

In one embodiment of the present disclosure, Form Gamma of Rucaparib S-Camsylate is isolated.

The above solid state forms of Rucaparib and of Rucaparib salts can be used to prepare other solid state forms of Rucaparib or other solid state forms of salts of Rucaparib. The present invention comprises a process for preparing solid state forms of Rucaparib and of Rucaparib salts, comprising preparing any one or a combination of the solid state forms of Rucaparib and of Rucaparib salts of the present invention and converting it to another solid state form of Rucaparib or of Rucaparib salt.

The present disclosure provides solid state forms of Rucaparib and solid state forms of salts of Rucaparib for use in the preparation of pharmaceutical compositions and/or formulations comprising solid state forms of Rucaparib and/or solid state forms of salts of Rucaparib.

The present disclosure also encompasses the use of the solid state forms of Rucaparib and/or solid state forms of salts of Rucaparib of the present disclosure for the preparation of pharmaceutical compositions and/or formulations of solid state forms of Rucaparib and/or solid state forms of salts of Rucaparib.

The present disclosure comprises processes for preparing the above mentioned pharmaceutical formulations. The processes comprise combining any one or a combination of the solid state forms of Rucaparib and/or solid state forms of salts of Rucaparib of the present disclosure with at least one pharmaceutically acceptable excipient.

The solid state forms of Rucaparib and/or solid state forms of salts of Rucaparib and the pharmaceutical compositions of solid state forms of Rucaparib and/or solid state forms of salts of Rucaparib of the present disclosure, can be used as medicaments, particularly for the treatment of cancer.

The present disclosure also provides methods of treating cancer comprising administering a therapeutically effective amount of any one or a combination of the solid state forms of Rucaparib and/or solid state forms of salts of Rucaparib of the present disclosure, or at least one of the above pharmaceutical compositions, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification.

The Examples are set forth to aid in understanding the disclosure but are not intended to, and should not be construed to limit its scope in any way.

Powder X-Ray Diffraction ("PXRD")—Method 1

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångstrom), X'Celerator (2.022° 2θ) detector.

Scanning parameters: angle range: 3-40 deg., step size 0.0167, time per step 37 s, continuous scan.

The described peak positions were determined with or without using silicon powder as an internal standard in an admixture with the sample measured.

The position of the silicon (Si) peak was corrected to silicone theoretical peak: 28.45 degrees two theta and the positions of the measured peaks were corrected respectively.

Powder X-Ray Diffraction ("PXRD")—Method 2

The XRPD patterns were collected on a PANalytical X'Pert Pro powder diffractometer model PW3050/60 using Cu Kα radiation in Bragg-Brentano geometry and equipped with a X'celerator detector.

The tube voltage and amperage were set to 45 kV and 40 mA, respectively. The software used for data collection was X'Pert Data Collector and the data were analyzed and presented using X'Pert HighScore. The VT-XRPD data were collected using Anton Paar TTK 450 Low-Temperature Chamber. The sample was prepared by mounting approximately 50 mg of a sample in a sample holder.

Scanning parameters: 3-40 deg., step size 0.0167, scan speed 0.668°/s, number of steps 2214.

EXAMPLES

WO 2006-33007 (Example 4) describes the preparation of Rucaparib Phosphate Form III.

Solid State NMR ("ssNMR") Method

Solid-state $^{13}$C NMR spectra were recorded with variable amplitude cross polarization, magic angle spinning and high power proton decoupling using a BRUKER Avance II+ spectrometer operating at 125 MHz and room temperature. A probe using 4 mm o.d. zirconia rotors was employed. The operation conditions were: contact time:2 ms; recycle delay: 4 s; 1024 scans and spin rate of 11 kHz. Chemical shifts were referenced via a replacement sample of glycine (carboxyl carbon chemical shift assigned as 176.03 ppm relative to the signal of tetramethylsilane).

Preparation of Starting Materials

Example 1: Preparation of (4-((methylamino)methyl)phenyl)boronic acid (4-Formylphenyl)boronic acid (10 g; 66.64 mmol) is charged in a round-bottom flask and dissolved in absolute ethanol (100 ml) to form a clear yellow solution. Methylamine (8M absolute ethanol solution; 25 ml; 199.9 mmol) is added dropwise at 0-5° C. The imine formed is stirred for 1 hour at ambient temperature. Raney-Nickel (3 g; 30% w/w) is suspended in absolute ethanol (25 ml) and the imine solution is added. Reduction of imine is performed by hydrogenation in 300 ml autoclave for 5 hours at 40° C. and pressure of 5 bar. After filtration of catalyst through Celite, the solution of (4-((methylamino)methyl)phenyl)boronic acid is concentrated to about 100 mL to be used in the next step.

Example 2: Preparation of (4-((methylamino)methyl)phenyl)boronic acid (4-Formylphenyl)boronic acid (10 g; 66.64 mmol) is charged in a round-bottom flask and dissolved in methanol (100 ml) to form a clear yellow solution. Methylamine (9.8M methanol solution; 20.4 ml; 199.9 mmol) is added dropwise at ambient temperature. The imine that forms is stirred for 1 hour at ambient temperature. Raney-Nickel (3 g; 30% w/w) is suspended in methanol (25 ml) and the imine solution is added. Reduction of imine is performed by hydrogenation in 300 ml autoclave for 5 hours at 40° C. and pressure of 5 bar. After filtration of catalyst through Celite, the solution of (4-((methylamino)methyl)phenyl)boronic acid is concentrated to about 100 mL to be used in the next step.

Example 3: Preparation of 2-bromo-8-fluoro-4,5-dihydro-1H-azepino[5,4,3-cd]indol-6(3H)-one 8-Fluoro-4,5-dihydro-1H-azepino[5,4,3-cd]indol-6(3H)-one, (10 g; 49.0 mmol) is suspended at ambient temperature in 1 L reactor in 225 mL of dichloromethane/tetrahydrofuran mixture (1/3). Obtained suspension is cooled to 5° C. while stirring and THF solution of pyridinium tribromide is added dropwise (17.22 g; 53.9 mmol in 75 mL THF). Obtained suspension is stirred at 5° C. for 2 hours until conversion is complete. Water (100 mL) is added to obtain clear orange solution. Solution is concentrated under vacuum until crystallization occurs. To obtained suspension 750 mL of ½ saturated $Na_2CO_3$ is added and suspension is stirred for 1 hour at ambient temperature. Obtained crystals are filtered, washed with water (100 mL) and dried in vacuum oven at 55° C. for 4 hours to obtain 11.3 g of 2-bromo-8-fluoro-4,5-dihydro-1H-azepino[5,4,3-cd]indol-6(3H)-one.

Example 4: Preparation of 8-fluoro-2-(4-((methylamino)methyl)phenyl)-4,5-dihydro-1H-azepino[5,4,3-cd]indol-6(3H)-one 2-Bromo-8-fluoro-4,5-dihydro-1H-azepino[5,4,3-cd]indol-6(3H)-one (10 g; 35.3 mmol), prepared according to process described in Example 3, potassium carbonate (4.88 g; 35.3 mmol), bis(triphenylphosphine)palladium(II) diacetate (0.794 g; 1.06 mmol) and (4-((methylamino)methyl) phenyl)boronic acid solution (70 ml; 42.4 mmol), prepared according to process described in Example 2, are charged into a three-necked round bottom flask, followed by inertisation with argon. A previously degassed mixture of methanol (200 mL) and water (40 mL) is added and the reaction mixture is stirred at 50° C. for 17 hours. The reaction mixture is cooled to ambient temperature followed by addition of activated carbon. The mixture is stirred at ambient temperature for one hour, heated to 50° C., stirred for another two hours and then filtered through a layer of celite. The solution of 8-fluoro-2-(4-((methylamino)methyl)phenyl)-4,5-dihydro-1H-azepino[5,4,3-cd]indol-6(3H)-one is concentrated to about 110 mL and divided into 4 parts to be used in the next step of salt preparation.

Example 5: Preparation of 8-fluoro-2-(4-((methylamino)methyl)phenyl)-4,5-dihydro-1H-azepino[5,4,3-cd]indol-6(3H)-one 2-Bromo-8-fluoro-4,5-dihydro-1H-azepino[5,4,3-cd]indol-6(3H)-one (10 g; 35.3 mmol), prepared according to process described in Example 3, sodium carbonate (3.74 g; 35.3 mmol), bis(triphenylphosphine)palladium(II) diacetate (0.529 g; 0.71 mmol) and (4-((methylamino)methyl)phenyl) boronic acid solution (75 ml; 45.9 mmol), prepared according to process described in Example 2, are charged into a three-necked round bottom flask, followed by inertisation with nitrogen. A previously degassed mixture of methanol (130 mL) and water (40 mL) is added and the reaction mixture is stirred at 60° C. for 4 hours. The reaction mixture is cooled to ambient temperature followed by addition of activated carbon. The mixture is stirred at ambient temperature for one hour, heated to 50° C., stirred for another hour and then filtered through a layer of celite. The solution of 8-fluoro-2-(4-((methylamino)methyl)phenyl)-4,5-dihydro-1H-azepino[5,4,3-cd]indol-6(3H)-one is concentrated to about 110 mL, heated to 40° C. followed by dropwise addition of water (40 mL). Reaction mixture is cooled to ambient temperature and stirred for 17 hours at ambient temperature and additional one hour at 0-5° C. Solid is filtered off, washed with water and dried in vacuum oven at 50° C. for 5 hours. Crude material (9.5 g) is suspended in methanol (95 mL) at reflux temperature and stirred for 20 minutes. Suspension is than cooled down and stirred for 17 hours at ambient temperature and 1.5 hour at 0-5° C. Crystals are filtered off, washed with methanol and dried in vacuum oven at 50° C. for 4 hours to obtain 6.82 g of Rucaparib base.

Example 6: Preparation of Rucaparib Hydrochloride Form II

2-Bromo-8-fluoro-4,5-dihydro-1H-azepino[5,4,3-cd]indol-6(3H)-one (10 g; 35.3 mmol), prepared according to process described in Example 3, is charged into a three-necked round bottom flask. Potassium carbonate (4.88 g; 35.3 mmol) and bis(triphenylphosphine)palladium(II) diacetate (1.06 g; 1.41 mmol) are also charged and the flask is closed with septum seals, followed by inertisation with Ar. A previously degassed mixture of ethanol (200 mL) and water (40 mL) is added through septum seals, followed by addition of (4-((methylamino)methyl)phenyl)boronic acid solution (70 ml; 42.4 mmol), prepared according to process described in Example 1. The reaction mixture is stirred at 60° C. for 17 hours. The reaction mixture is cooled to ambient temperature followed by addition of activated carbon. The mixture is stirred at ambient temperature for two hours, heated to 50° C., stirred for another two hours and then filtered through a layer of celite. The filter cake is washed with ethanol until the passing solvent loses yellow coloration. The yellow mother liquor is concentrated to about 80 mL. A solution of ethanol, water and conc. HCl is prepared (7V ethanol, 12V $H_2O$, 4V conc. HCl) and added dropwise while stirring at ambient temperature. The yellow suspension is left stirring for 17 hours. The suspension is cooled to 0° C. and stirred for one hour before filtration. The yellow Rucaparib hydrochloride is washed with water and dried in a vacuum dryer at 50° C. until constant mass. The solids are then suspended in dichloromethane (5V) and stirred at reflux temperature for 5 minutes, cooled to ambient temperature and then to 0° C. The suspension is stirred at 0° C. for an hour and then filtered; the solids are washed with dichloromethane. Rucaparib hydrochloride is then dried in vacuum oven at 50° C. until constant mass (12.0 g).

XRPD is given in FIG. 1.

Example 7: Preparation of Rucaparib Hydrochloride Form III 50 mg Rucaparib Hydrochloride Form II was dissolved in 4 mL of ethanol, 96% at about 78° C. Solution was covered lightly with lid and left to evaporate at room conditions for 24 hours. Filtrated product was analyzed by XRPD.

XRPD is given in FIG. 2.

Example 8: Preparation of Rucaparib Hydrochloride Form IV 50 mg Rucaparib Hydrochloride Form II was dissolved in 1 mL of methanol at about 65° C. Solution was covered lightly with lid and cooled to 25° C. Filtrated product was analyzed by XRPD.

XRPD is given in FIG. 3.

Example 9: Preparation of Rucaparib Acetate Form I

To the water/methanol (1/1.5) solution of Rucaparib base (27.5 mL; 7.7 mmol), prepared according to the process described in Example 4, solution of acetic acid in water/methanol mixture (29 mL of following solution: 2.21 mL of acetic acid dissolved in 35 mL of water and 10 mL of methanol) is added dropwise while stirring at ambient temperature. Thick brown suspension is stirred for 48 hours at ambient temperature, then at 0° C. for 1 hour. Crystals are filtered off under vacuum. Wet crystals are dried in vacuum oven at 50° C. for 5 hours to obtain 3.32 g of Rucaparib Acetate salt.

XRPD is given in FIG. 4.

Example 10: Preparation of Rucaparib Acetate Form II 50 mg Rucaparib acetate Form I was dissolved in 1 mL of ethanol 96% at about 50° C. Solution was covered lightly with lid and cooled to 25° C., and left to evaporate during 24 hours. Filtrated product was analyzed by XRPD.

XRPD is given in FIG. 5.

Preparation of Rucaparib Acetate Form III

Example 11

50 mg Rucaparib Acetate Form I was suspended in 5 mL of i-butyl acetate at about 118° C. Suspension is cooled to room conditions and crude material is filtrated off. Isolated product was analyzed by XRPD.

Example 12

50 mg Rucaparib Acetate Form I was suspended in 5 mL of sec-butyl acetate at about 112° C. Suspension is cooled to room conditions and crude material is filtrated off. Isolated product was analyzed by XRPD.

Example 13

50 mg Rucaparib Acetate Form I was suspended in 5 mL of absolute ethanol at about 78° C. Suspension is cooled to room conditions and crude material is filtrated off. Isolated product was analyzed by XRPD.

Example 14

50 mg Rucaparib Acetate Form I was suspended in 5 mL of methyl ethyl ketone at about 80° C. Suspension is cooled to room conditions and crude material is filtrated off. Isolated product was analyzed by XRPD.

Example 15

50 mg Rucaparib Acetate Form I was suspended in 5 mL of n-propyl acetate at about 102° C. Suspension is cooled to room conditions and crude material is filtrated off. Isolated product was analyzed by XRPD.

Example 16

50 mg Rucaparib Acetate Form I was suspended in 5 mL of 2-propanol at about 82° C. Suspension is cooled to room conditions and crude material is filtrated off. Isolated product was analyzed by XRPD.

Example 17

50 mg Rucaparib Acetate Form I was suspended in 5 mL of tetrahydrofuran at about 66° C. Suspension is cooled to room conditions and crude material is filtrated off. Isolated product was analyzed by XRPD.

XRPD is given in FIG. 6.

Preparation of Rucaparib Acetate Form IV

Example 18

1 g of Rucaparib base (3.09 mmol), prepared according to the process described in Example 5, was dissolved in 15 mL of THF/H2O mixture (2:1) while heating at 40-50° C. To the clear solution of Rucaparib base, 353 µL (2 eq) of acetic acid, was added while stirring at 40-50° C. Clear reaction mixture was then cooled down and crystallization occurred while stirring in ice bath. Obtained suspension was stirred for 1 hour at 0-5° C. Crystals were filtered off under vacuum. Wet crystals were dried in vacuum oven at 50° C. for 4 hours to obtain 0.621 g of Rucaparib Acetate salt. Obtained material was analyzed by XRPD.

XRPD is given in FIG. 7.

Preparation of Rucaparib Hydrobromide Form I

Example 19

To the water/methanol (1/1.5) solution of Rucaparib base (27.5 mL; 7.7 mmol), prepared according to the process described in Example 4, solution of hydrobromic acid in water/methanol mixture (27 mL of following solution: 4.37 mL of hydrobromic acid dissolved in 35 mL of water and 10 mL of methanol) is added dropwise while stirring at ambient temperature. Yellow suspension is stirred for 48 hours at ambient temperature, then at 0° C. for 1 hour. Crystals are filtered off, washed with cold water and filtered off under vacuum. Wet crystals are dried in vacuum oven at 50° C. for 2 hours to obtain 2.17 g of Rucaparib Hydrobromide salt.

XRPD is given in FIG. 8.

Preparation of Rucaparib Hydrobromide Form II

Example 20

50 mg Rucaparib Hydrobromide Form I was suspended in 5 mL of acetonitrile at about 82° C. Suspension is cooled to room conditions and crude material is filtrated off. Isolated product was analyzed by XRPD.

Example 21

50 mg Rucaparib Hydrobromide Form I was suspended in 5 mL of 1-butanol at about 118° C. Suspension is cooled to room conditions and crude material is filtrated off. Isolated product was analyzed by XRPD.

Example 22

50 mg Rucaparib Hydrobromide Form I was suspended in 5 mL of 2-butanol at about 95° C. Suspension is cooled to room conditions and crude material is filtrated off. Isolated product was analyzed by XRPD.

Example 23

50 mg Rucaparib Hydrobromide Form I was suspended in 5 mL of i-butyl acetate at about 118° C. Suspension is cooled to room conditions and crude material is filtrated off. Isolated product was analyzed by XRPD.

Example 24

50 mg Rucaparib Hydrobromide Form I was suspended in 5 mL of n-butyl acetate at about 126° C. Suspension is cooled to room conditions and crude material is filtrated off. Isolated product was analyzed by XRPD.

Example 25

50 mg Rucaparib Hydrobromide Form I was suspended in 5 mL of sec-butyl acetate at about 112° C. Suspension is cooled to room conditions and crude material is filtrated off. Isolated product was analyzed by XRPD.

Example 26

50 mg Rucaparib Hydrobromide Form I was dissolved in 1 mL of N,N-dimethylformamide at about 153° C. Solution was covered lightly with lid and cooled to 25° C., and left to evaporate during 4 hours. Filtrated product was analyzed by XRPD.

Example 27

50 mg Rucaparib Hydrobromide Form I was suspended in 5 mL of ethyl acetate at about 77° C. Suspension is cooled to room conditions and crude material is filtrated off. Isolated product was analyzed by XRPD.

Example 28

50 mg Rucaparib Hydrobromide Form I was suspended in 5 mL of methyl acetate at about 58° C. Suspension is cooled to room conditions and crude material is filtrated off. Isolated product was analyzed by XRPD.

Example 29

50 mg Rucaparib Hydrobromide Form I was suspended in 5 mL of methyl ethyl ketone at about 80° C. Suspension is cooled to room conditions and crude material is filtrated off. Isolated product was analyzed by XRPD.

Example 30

50 mg Rucaparib Hydrobromide Form I was suspended in 5 mL of methyl i-butyl ketone at about 117° C. Suspension is cooled to room conditions and crude material is filtrated off. Isolated product was analyzed by XRPD.

Example 31

50 mg Rucaparib Hydrobromide Form I was suspended in 5 mL of 1-pentanol at about 137° C. Suspension is cooled to room conditions and crude material is filtrated off. Isolated product was analyzed by XRPD.

Example 32

50 mg Rucaparib Hydrobromide Form I was suspended in 5 mL of water at about 100° C. Suspension is cooled to room conditions and crude material is filtrated off. Isolated product was analyzed by XRPD.

XRPD is given in FIG. 9.

Preparation of Rucaparib Hydrobromide Form III

Example 33

50 mg Rucaparib Hydrobromide Form I was dissolved in 1 mL of N,N-dimethylacetamide at about 166° C. Solution was covered lightly with lid and cooled to 25° C., and left to evaporate during 24 hours. Filtrated product was analyzed by XRPD.

XRPD is given in FIG. 10.

Preparation of Rucaparib Hydrobromide Form IV

Example 34

Rucaparib Hydrobromide (Form I prepared according to Example 19, 1.20 mg) was placed in pin hole aluminum pan. The sample was heated in a DSC Discovery TA instrument according to following steps:

a) The sample was heated up to temperature of 285° C. at heating rate of 10° C./minute b) The sample was kept isothermally at 285° C. for 5 minutes The sample was left to cool at temperature of about 25° C., then the sample was analyzed by XRPD, Form IV was obtained.

Figure 11:
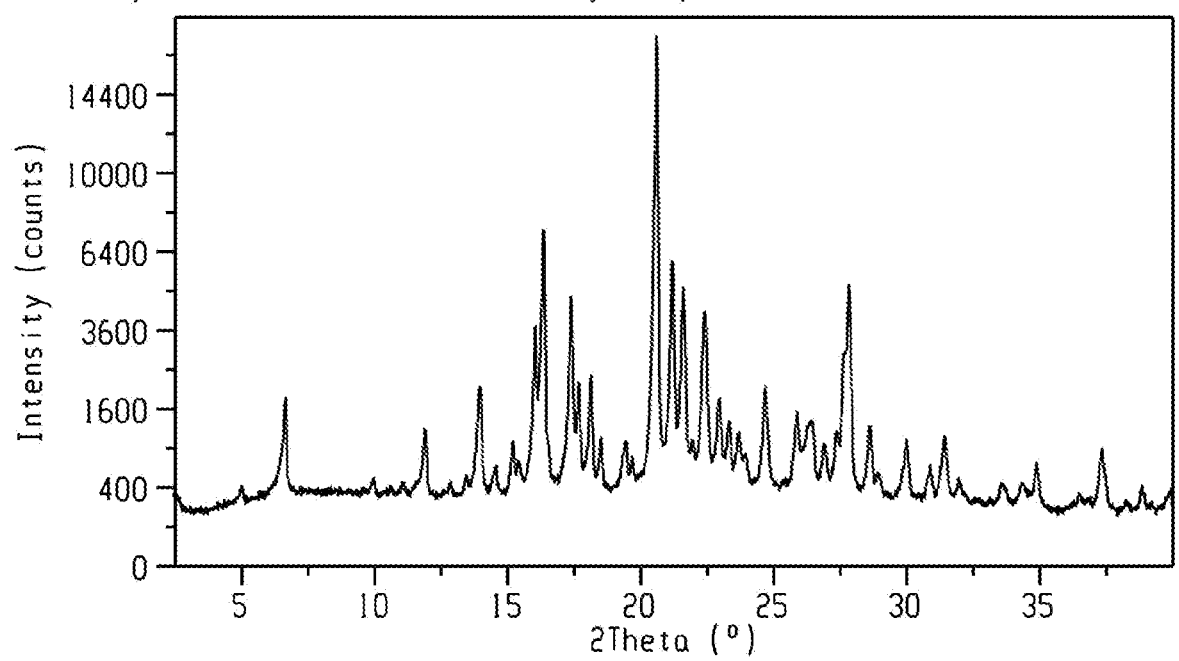
FIG. 11 shows X-ray powder diffraction pattern of a sample comprising Rucaparib Hydrobromide Form IV obtained by example 34.

XRPD is given in FIG. 11.

Preparation of Rucaparib Citrate Form I and Form II

Example 35

1 g of Rucaparib base (3.09 mmol), prepared according to the process described in Example 5, was dissolved in 15 mL of THF/H2O mixture (2:1) while heating at 40-50° C. To the clear solution of Rucaparib base, 1.42 g (2 eq) of citric acid dissolved in 5 mL of water, was added while stirring at 40-50° C. Clear reaction mixture was then cooled down and crystallization occurred while stirring in ice bath. Obtained suspension was stirred for 1 hour at 0-5° C. Crystals were filtered off under vacuum and analyzed by XRPD as Form I of Rucaparib Citrate. Obtained Form I of Rucaparib Citrate was dried in vacuum oven at 50° C. for 4 hours to obtain 1.395 g of material that was analyzed by XRPD as Form II of Rucaparib Citrate.

XRPD of Rucaparib Citrate Form I is given in FIG. 12.
XRPD of Rucaparib Citrate Form II is given in FIG. 13.

Preparation of Rucaparib D-(−)-Tartrate Form I and Form II

Example 36

1 g of Rucaparib base (3.09 mmol), prepared according to the process described in Example 5, was dissolved in 15 mL of THF/H$_2$O mixture (2:1) while heating at 40-50° C. To the clear solution of Rucaparib base, 0.93 g (2 eq) of D-(−)-tartaric acid dissolved in 5 mL of water, was added while stirring at 40-50° C. Clear reaction mixture was then cooled down and crystallization occurred while stirring in ice bath. Obtained suspension was stirred for 1 hour at 0-5° C. Crystals were filtered off under vacuum and analyzed by XRPD as Form I of Rucaparib D-(−)-Tartrate.

Wet crystals were dried in vacuum oven at 50° C. for 4 hours to obtain 1.07 g of material, that was analyzed by XRPD as Form II of Rucaparib D-(−)-Tartrate.

XRPD of Rucaparib D-(−)-Tartrate Form I is given in FIG. 14.

XRPD of Rucaparib D-(−)-Tartrate Form II is given in FIG. 15.

Preparation of Rucaparib Hemi-Edisylate Form I

Example 37

To the water/methanol (1/1.5) solution of Rucaparib base (27.5 mL; 7.7 mmol), prepared according to the process described in Example 4, solution of 1,2-ethanedisulfonic acid in water/methanol mixture (45 mL of following solution: 3.67 g of ethanedisulphonic acid dissolved in 35 mL of water and 10 mL of methanol) was added dropwise while stirring at ambient temperature. Thick suspension was stirred for 48 hours at ambient temperature, then at 0° C. for 1 hour. Crystals were filtered off, washed with cold water and dried in vacuum oven at 50° C. for 2 hours to obtain 1.81 g of Rucaparib Hemi-Edisylate salt, that was analyzed by XRPD as Form I.

XRPD of Rucaparib Hemi-Edisylate Form I is given in FIG. 16.

Preparation of Rucaparib Tosylate Form I

Example 38

To the water/methanol (1/1.5) solution of Rucaparib base (27.5 mL; 7.7 mmol), prepared according to the process described in Example 4, solution of p-toluenesulphonic acid in water/methanol mixture (45 mL of following solution: 6.65 g of p-toluenesulfonic acid dissolved in 35 mL of water and 10 mL of methanol) was added dropwise while stirring at ambient temperature. Oily product was heated to 35° C., and crystallization occurred while cooling to ambient temperature. Obtained crystals were stirred at ambient temperature overnight. Crystals were filtered off, washed with water and dried in vacuum oven at 50° C. for 2 hours to obtain 3.18 g of Rucaparib Tosylate salt that was analyzed by XRPD as Form I.

XRPD of Rucaparib Tosylate Form I is given in FIG. 17.

Preparation of Rucaparib Mesylate Form I and Form II

Example 39

1 g of Rucaparib base (3.09 mmol), prepared according to the process described in Example 5, was dissolved in 15 mL of THF/H2O mixture (2:1) while heating at 40-50° C. To the clear solution of rucaparib base, 574 μL (2 eq) of methanesulfonic acid, was added while stirring at 40-50° C. Clear reaction mixture was then cooled down and crystallization occurred while stirring at ambient temperature for 20 hours. Crystals were filtered off under vacuum and analyzed by XRPD as Form I of Rrucaparib Mesylate.

Wet crystals were dried in vacuum oven at 50° C. for 4 hours to obtain 1.057 g of Rucaparib Mesylate salt, that was analyzed by XRPD as Form II.

XRPD of Rucaparib Mesylate Form I is given in FIG. 18.

XRPD of Rucaparib Mesylate Form II is given in FIG. 19.

Example 40: Preparation of Rucaparib Tosylate Form II 50 mg Rucaparib Tosylate Form I was exposed to 1-buthanol atmosphere at room conditions. After 3 days, sample was analyzed by XRPD.

XRPD is given in FIG. 20.

Example 41: Preparation of Rucaparib Tosylate Form III 50 mg Rucaparib Tosylate Form I was exposed to methanol atmosphere at room conditions. After 3 days, sample was analyzed by XRPD.

XRPD is given in FIG. 21.

Example 42: Preparation of Rucaparib Tosylate Form III

Rucaparib Tosylate Form I was placed in pin hole aluminum pan. The sample was heated in DSC Discovery TA instrument according to following steps:
 a) The sample was heated up to temperature of 200° C. at heating rate of 10° C./minute
 b) The sample was kept isothermally at 200° C. for 5 minutes The sample was left to cool at temperature of about 25° C., then the sample was analyzed by XRPD; Form III was obtained.

Example 43: Preparation of Rucaparib Tosylate Form III 50 mg Rucaparib Tosylate Form I was suspended in 5 mL of acetonitrile at about 82° C. Suspension was cooled to room conditions and crude material is filtered off. Isolated product was analyzed by XRPD.

Example 44: Preparation of Rucaparib Tosylate Form III 50 mg Rucaparib Tosylate Form I was suspended in 5 mL of 1-butanol at about 118.0° C. Suspension was cooled to room conditions and crude material is filtered off. Isolated product was analyzed by XRPD.

Example 45: Preparation of Rucaparib Tosylate Form III 50 mg Rucaparib Tosylate Form I was suspended in 5 mL of 2-butanol at about 94.0° C. Suspension was cooled to room conditions and crude material is filtered off. Isolated product was analyzed by XRPD.

Example 46: Preparation of Rucaparib Tosylate Form III 50 mg Rucaparib Tosylate Form I was suspended in 5 mL of 1,2-Dimethoxyethane at about 83.0° C. Suspension was cooled to room conditions and crude material is filtered off. Isolated product was analyzed by XRPD.

Example 47: Preparation of Rucaparib Tosylate Form III 50 mg Rucaparib Tosylate Form I was suspended in 5 mL of 1-pentanol at about 137.0° C. Suspension was cooled to room conditions and crude material is filtered off. Isolated product was analyzed by XRPD.

Example 47A

Preparation of Rucaparib Tosylate Form III

To a suspension of 3.0 g of Rucaparib Base in 90.0 ml of techn. EtOH at 20-25° C., 1.76 g of p-toluenesulfonic acid monohydrate was added. After stirring for about 24 hours at 20-25° C. crystals were filtered off, washed twice with 7.5 ml of techn. EtOH and dried at 50° C./20 mbar for about 16 hours. 3.7 g of Rucaparib tosylate form III was obtained.

Example 48: Preparation of Rucaparib Tosylate Form IV 50 mg Rucaparib Tosylate Form I was exposed to acetone atmosphere at room conditions. After 3 days, sample was analyzed by XRPD.

XRPD is given in FIG. 22.

Example 49: Preparation of Rucaparib Tosylate Form V 1 g of Rucaparib base (3.09 mmol) and 0.599 g (3.15 mmol) of p-toluenesulfonic acid mono-hydrate, was dissolved in 40 mL of ethanol, 96% at ambient temperature. Solution was heated to 70±2° C. and stirred at that temperature for 15 minutes. Solution was then cooled down to 25±2° C. and product started to precipitate. Obtained suspension was stirred at 25±2° C. for 17 hours. Crystals were filtered off under vacuum and dried in vacuum oven at 50° C. for 4 hours to obtain 0.838 g of material that was analyzed by XRPD.

XRPD is given in FIG. 23.

Example 50: Preparation of Rucaparib Tosylate Form V

Rucaparib Tosylate (mixture of Form V and Form VI, prepared according to Example 51) was placed in pin hole aluminum pan. The sample was heated in DSC Discovery TA instrument according to following steps:

a) The sample was heated up to temperature of 160° C. at heating rate of 10° C./minute.

b) The sample was kept isothermally at 160° C. for 5 minutes.

The sample was left to cool at temperature of about 25° C., then the sample was analyzed by XRPD, Form V was obtained.

Example 51: Preparation of Mixture of Rucaparib Tosylate Form V+Rucaparib Tosylate Form VI 50 mg Rucaparib Tosylate Form I was exposed to acetonitrile atmosphere at room conditions. After 3 days, sample was analyzed by XRPD.

XRPD is given in FIG. 24.

Example 52: Preparation of Rucaparib Hemi-Edisylate Form III 50 mg Rucaparib Hemi-Edisylate Form I was exposed to methanol atmosphere at room conditions. After 30 days, sample was analyzed by XRPD.

XRPD is given in FIG. 25.

Example 53: Preparation of Rucaparib Hemi-Edisylate Form III 50 mg Rucaparib hemiedisylate Form I was suspended in 5 mL of sec-Butyl acetate at about 112.0° C. Suspension is cooled to room conditions and crude material is filtered off. Isolated product was analyzed by XRPD.

Example 54: Preparation of Rucaparib Hemi-Edisylate Form III 50 mg Rucaparib Hemi-Edisylate Form I was suspended in 5 mL of tert-Butyl acetate at about 98.0° C. Suspension is cooled to room conditions and crude material is filtered off. Isolated product was analyzed by XRPD.

Example 55: Preparation of Rucaparib Hemi-Edisylate Form III 50 mg Rucaparib Hemi-Edisylate Form I was suspended in 5 mL of cyclohexane at about 81.0° C. Suspension is cooled to room conditions and crude material is filtered off. Isolated product was analyzed by XRPD.

Example 56: Preparation of Rucaparib Hemi-Edisylate Form III 50 mg Rucaparib Hemi-Edisylate Form I was suspended in 5 mL of ethyl acetate at about 77.0° C. Suspension is cooled to room conditions and crude material is filtered off. Isolated product was analyzed by XRPD.

Example 57: Preparation of Rucaparib Hemi-Edisylate Form III 50 mg Rucaparib Hemi-Edisylate Form I was suspended in 5 mL of heptane at about 98.0° C. Suspension is cooled to room conditions and crude material is filtered off. Isolated product was analyzed by XRPD.

Example 58: Preparation of Rucaparib Hemi-Edisylate Form III 50 mg Rucaparib Hemi-Edisylate Form I was suspended in 5 mL of methanol at about 64.5° C. Suspension is cooled to room conditions and crude material is filtered off. Isolated product was analyzed by XRPD.

Example 59: Preparation of Rucaparib Hemi-Edisylate Form III 50 mg Rucaparib Hemi-Edisylate Form I was suspended in 5 mL of methyl acetate at about 58.0° C. Suspension is cooled to room conditions and crude material is filtered off. Isolated product was analyzed by XRPD.

Example 60: Preparation of Rucaparib Hemi-Edisylate Form III 50 mg Rucaparib Hemi-Edisylate Form I was dissolved in 1 mL of N-methyl-pyrrolidone at about 128.5° C. Suspension is cooled to room conditions and crude material is filtered off. Isolated product was analyzed by XRPD.

Example 61: Preparation of Rucaparib Hemi-Edisylate Form III 50 mg Rucaparib Hemi-Edisylate Form I was suspended in 5 mL of toluene at about 111.0° C. Suspension is cooled to room conditions and crude material is filtered off. Isolated product was analyzed by XRPD.

Example 62: Preparation of Rucaparib Hemi-Edisylate Form IV 1 g of Rucaparib base (3.09 mmol) and 0.656 g (3.15 mmol) of 1,2-Ethane-Disulfonic acid hydrate, was dissolved in 40 mL of ethanol, 96%. After few minutes product started to precipitate. Obtained suspension was heated to 70±2° C. and stirred at that temperature for 15 minutes. Suspension was then cooled down to 25±2° C. and stirred at that temperature for 2 hours. Crystals were filtered off under vacuum and analyzed by XRPD as Form IV of Rucaparib Hemi-Edisylate. Obtained Form IV of Rucaparib Hemi-Edisylate was dried in vacuum oven at 50° C. for 4 hours to obtain 1.209 g of material that was analyzed by XRPD as Form IV of Rucaparib Hemi-Edisylate.

Example 63: Preparation of Rucaparib Hemi-Edisylate Form IV 50 mg Rucaparib Hemi-Edisylate Form I was suspended in 5 mL of acetone at about 56.5° C. Suspension was cooled to room conditions and crude material is filtered off. Isolated product was analyzed by XRPD.
XRPD is given in FIG. 26.

Example 64: Preparation of Rucaparib Hemi-Edisylate Form IV 50 mg Rucaparib Hemi-Edisylate Form I was suspended in 5 mL of acetonitrile at about 81.6° C. Suspension was cooled to room conditions and crude material is filtered off. Isolated product was analyzed by XRPD.

Example 65: Preparation of Rucaparib Hemi-Edisylate Form IV 50 mg Rucaparib Hemi-Edisylate Form I was suspended in 5 mL of n-Butyl acetate at about 126.0° C. Suspension was cooled to room conditions and crude material is filtered off. Isolated product was analyzed by XRPD.

Example 66: Preparation of Rucaparib Hemi-Edisylate Form IV 50 mg Rucaparib Hemi-Edisylate Form I was suspended in 5 mL of ethyl butyl ketone at about 80.0° C. Suspension was cooled to room conditions and crude material is filtered off. Isolated product was analyzed by XRPD.

Example 67: Preparation of Rucaparib Hemi-Edisylate Form IV 50 mg Rucaparib Hemi-Edisylate Form I was suspended in 5 mL of methyl iso-butyl ketone at about 117.0° C. Suspension was cooled to room conditions and crude material is filtered off. Isolated product was analyzed by XRPD.

Example 68: Preparation of Rucaparib L-(+)-Tartrate: Form I and Form II 4 g of rucaparib base (12.36 mmol), prepared according to the process described in Example 5, was dissolved in 60 mL of THF/H2O mixture (2:1) while heating at 40-50° C. To the clear filtered solution of rucaparib base, 3.72 g (2 eq) of L-(+)-tartaric acid dissolved in 15 mL of water, was added while stirring at 40-50° C. Clear reaction mixture was then cooled down and crystallization occurred while stirring at 20-25° C. Obtained suspension was additionally stirred for 1 hour at 0-5° C. Crystals were filtered off under vacuum, washed with 2*20 mL H2O and analyzed by XRPD as Form I of rucaparib L-(+)-tartarate.

Wet crystals were dried in vacuum oven at 50° C. for 4 hours to obtain 3.82 g of material that was analyzed by XRPD as Form II of rucaparib L-(+)-tartrate.

Example 69: Preparation of Rucaparib L-(+)-Tartrate Form I 70 mg Rucaparib L-(+)-Tartarate Form II was exposed to 100% relative humidity in controlled atmosphere at room temperature. After one month the sample was analyzed by XRPD. Form I was obtained.

Example 70: Preparation of Rucaparib Esylate Form I 1 g (0.309 mmol) of Rucaparib free base was suspended at room temperature in 40 mL of 96% EtOH. Reaction mixture was then heated to 75-80° C. and clear yellow solution was obtained. 0.74 mL (0.927 mmol) of Ethanesulfonic acid was added dropwise. The reaction mixture was then slowly cooled down to 0-5° C. Solvent was partly removed under reduced pressure and crystallization occurred. Suspension was stirred at 0-5° C. for 1.5 hour at 20-25° C. Crystals were filtered off and dried in vacuum oven at 50° C./10 mbar for 3 hours to obtain 0.79 g of Rucaparib Esylate Form I.
XRPD pattern is given in FIG. 29.

Example 71: Preparation of Rucaparib Esylate Form II

A sample of 50 mg of Rucaparib Esylate Form I of was placed in a PANalytical X'Pert Pro powder diffractometer model PW3050/60 sample holder and scanned from 3 to 40° 2θ using following acquisition parameters:
Step size: 0.0167° 2θ
Scan speed: 0.049°/s
Number of steps: 2214
Total collection time: 13 minutes The sample was ramped from 30° C. to 260° C. at 5° C./step and heating rate 10° C./min and then cooled at 30° C. XRPD patterns were acquired after cooling at 30° C. The sample temperature was controlled using Anton Paar TCU100 Temperature Control Unit. The XRPD patterns were collected on a PANalytical X'Pert Pro powder diffractometer model PW3050/60 using Cu Kα radiation in Bragg-Brentano geometry and equipped with a X'celerator detector. The tube voltage and amperage were set to 45 kV and 40 mA, respectively. The software used for data collection was X'Pert Data Collector. The VT-XRPD data were collected using Anton Paar TTK 450 Low-Temperature Chamber.

XRPD pattern is given in FIG. 30.

Example 72: Preparation of Rucaparib Esylate Form II 50 mg of Rucaparib Esylate (Mixture of Form I and V) was suspended in vial by shaking in 5 ml of acetone and heated at about 56° C., using heating plate, for 2-3 minutes. Suspension was cooled down to ambient conditions and filtrated after 4 days. Solid was analyzed by XRPD.

Example 73: Preparation of Rucaparib Esylate Form II 50 mg of Rucaparib Esylate (Mixture of Form I and V) was suspended in vial by shaking in 5 ml of acetonitrile and heated at about 82° C., using heating plate, for 2-3 minutes. Suspension was cooled down to RT and filtrated. Solid was analyzed by XRPD.

Example 74: Preparation of Rucaparib Esylate Form II 50 mg of Rucaparib Esylate (Mixture of Form I and V) was dissolved in vial by shaking in 1 ml of ethanol (abs.) at about 78° C., using heating plate. Solution was cooled down to ambient conditions. Solid was filtrated after 4 days and analyzed by XRPD.

Example 75: Preparation of Rucaparib Esylate Form II 50 mg of Rucaparib Esylate (Mixture of Form I and V) was dissolved in vial by shaking in 1 ml of 1-propanol at about 80° C., using heating plate. Solution was cooled down to ambient conditions. Solid was filtrated after 4 days and analyzed by XRPD.

Example 76: Preparation of Rucaparib Esylate Form II

Around 20 mg of Rucaparib Esylate (Mixture of Form I and V) was put in small vials and left in atmosphere of acetonitrile for 8 days at ambient conditions and then analyzed by XRPD.

Example 77A

Preparation of Rucaparib Esylate Form III 50 mg of Rucaparib Esylate (Mixture of Form I and V) was suspended in vial by shaking in 5 ml of methanol and heated at about to 64° C., using heating plate, for 2-3 minutes. Suspension was cooled down to ambient conditions and filtrated after 4 days. Solid was analyzed by XRPD.

XRPD pattern is given in FIG. 31.

Example 77B

Preparation of Rucaparib Esylate Form III

Around 20 mg of Rucaparib Esylate (Mixture of Form I and V) was put in small vials and left in atmosphere of methanol for 8 days at ambient conditions and then analyzed by XRPD.

Example 78: Preparation of Rucaparib Esylate Form IV 50 mg of Rucaparib Esylate (Mixture of Form I and V) was dissolved in vial by shaking in 1 ml of 1-pentanol at about 138° C. using heating plate. Solution was cooled down to ambient conditions. Solid was filtrated after 4 days and analyzed by XRPD.

XRPD pattern is given in FIG. 32.

Example 79: Preparation of Rucaparib Esylate Form V 50 mg of Rucaparib Esylate (Mixture of Form I and V) was dissolved in vial by shaking in 1 ml of ethanol (96%) at about 78° C. using heating plate. Solution was cooled down to ambient conditions. Solid was filtrated after 4 days and analyzed by XRPD.

XRPD pattern is given in FIG. 33.

Example 79A

Preparation of Rucaparib Esylate Form VI 50 mg of rucaparib esylate (Form I+Form V) was dissolved in 1 mL of ethylene glycol at ambient conditions in vial by stirring on vortex mixer for 10 seconds. Vial was closed with lid and left at ambient conditions. After 25 days crystalline product was filtered under vacuum and analyzed by XRPD. XRPD pattern is given in FIG. 33A

Example 80: Preparation of Rucaparib Form II 5.0 g of Rucaparib Phosphate Form III was suspended in 150 ml acetone:water mixture (1:2). Suspension is heated up to 30° C. and 1.05 eq of 20% sodium hydroxide solution was gradually added. Suspension was stirred for 1.5 hour and then filtrated off. The obtained product was analyzed by XRD, indicating that Form I was obtained. Product was further dried at 40-60° C. under vacuum until constant mass. The dried product was analyzed by XRD, indicating that Form II was obtained.

The XRD pattern is presented in FIG. 35.

Example 81: Preparation of Rucaparib Form I

Procedure 1:
50 mg of Rucaparib Form II was suspended in 5 ml of water and heated up to reflux temperature at about 100° C. Suspension was left for 5 days at ambient conditions and then filtrated off. Obtained solid was analyzed by XRD.

The XRD pattern is given in FIG. 34.

Procedure 2:

500 mg of Rucaparib Form II was suspended in 10 ml of water and heated up to reflux temperature at about 100° C. Suspension was cooled down to ambient conditions, stirred for 24 hours and filtrated off. Obtained solid was identified as Form I per analysis by XRD.

Procedure 3:

50 mg of Rucaparib Form II was dissolved in 3 ml of 2-propanol/water (1/1) and heated up to reflux temperature. Mixture was left for 5 days at ambient conditions to evaporate, after crystals appeared, suspension was filtrated off. Obtained solid was identified as Form I per analysis by XRD.

Procedure 4:

50 mg of Rucaparib Form II was dissolved in 2 ml of 1-propanol/water (1/1) and heated up to reflux temperature. Mixture was left for 5 days at ambient conditions to evaporate, after crystals appeared, suspension was filtrated off. Obtained solid was identified as Form I per analysis by XRD.

Procedure 5:

50 mg of Rucaparib Form II was dissolved in 1 ml of THF/water (1/1) and heated up to reflux temperature. Solution was left for 5 days at ambient conditions to evaporate, after crystals appeared, suspension was filtrated off. Obtained solid was identified as Form I per analysis by XRD.

Procedure 6:

50 mg of Rucaparib Form II was dissolved in 5 ml of acetonitrile/water (1/1) and heated up to reflux temperature. Mixture was left for 5 days at ambient conditions to evaporate, after crystals appeared, suspension was filtrated off. Obtained solid was identified as Form I per analysis by XRD.

Procedure 7:

50 mg of Rucaparib Form II was dissolved in 3 ml of ethanol/water (1/1) and heated up to reflux temperature. Mixture was left for 5 days at ambient conditions to evaporate, after crystals appeared, suspension was filtrated off. Obtained solid was identified as Form I per analysis by XRD.

Procedure 8:

50 mg of Rucaparib Form II was suspended in 5 ml of acetone/water (1/1) and heated up to reflux temperature at about 100° C. Suspension was left for 5 days at ambient conditions and then filtrated off. Obtained solid was identified as Form I per analysis by XRD.

Procedure 9:

50 mg of Rucaparib Form II was dissolved in 3 ml of N,N-dimethylsulphoxide/water (1/1) and heated up to reflux temperature. Mixture was left for 5 days at ambient conditions to evaporate, after crystals appeared, suspension was filtrated off. Obtained solid was identified as Form I per analysis by XRD.

Procedure 10:

50 mg of Rucaparib Form II was suspended in 5 ml of methanol/water (1/1) and heated up to reflux temperature at about 100° C. Suspension was left for 5 days at ambient conditions and then filtrated off. Obtained solid was identified as Form I per analysis by XRD.

Procedure 11:

117.0 g of Rucaparib Base was suspended in 1170 ml of water at 20-25° C. and stirred for about 6 hours. Crystals were filtered off, washed with 115 ml of water and dried at 50° C./20 mbar for about 19 hours. 118.1 g of Rucaparib Base Form I was obtained.

Example 82: Preparation of Rucaparib Form II

Procedure 1:

500 mg of Rucaparib Form II was suspended in 10 ml of methyl ethyl ketone (MEK) and heated up to reflux temperature at about 80° C. Suspension was cooled down to ambient conditions, stirred for 24 hours and filtrated off. Obtained solid was analyzed by XRD.

The XRD pattern is given in FIG. 36.

Procedure 2:

500 mg of Rucaparib Form II was suspended in 10 ml of 2-propanol and heated up to reflux temperature at about 80° C. Suspension was cooled down to ambient conditions, stirred for 24 hours and filtrated off. Obtained solid was identified as Form II per analysis by XRD.

Procedure 3:

50 mg of Rucaparib Form II was suspended in 5 ml of methyl tert-butyl ether and heated up to reflux temperature at about 55° C. Suspension was left for 5 days at room conditions and then filtrated off. Obtained solid was identified as Form II per analysis by XRD.

Procedure 4:

Sample of Form J was placed in aluminum pan with the pin hole. Sample was heated up at DSC Discovery TA instruments with the rate 10° C./minute up to temperature of 140° C. Sample was kept at this temperature for 2 minutes, and then analyzed by XRD. Obtained solid was identified as Form II per analysis by XRD.

Procedure 5:

Sample of Form C was placed in aluminum pan with the pin hole. Sample was heated up at DSC Discovery TA instruments with the rate 10° C./minute up to temperature of 140° C. Sample was kept at this temperature for 2 minutes, and then analyzed by XRD. Obtained solid was identified as Form II per analysis by XRD.

Procedure 6:

Sample of Form D was placed in aluminum pan with the pin hole.

Sample was heated up at DSC Discovery TA instruments with the rate 10° C./minute up to temperature of 140° C. Sample was kept at this temperature for 2 minutes, and then analyzed by XRD. Obtained solid was identified as Form II per analysis by XRD.

Procedure 7:

50 mg of Rucaparib Form II was suspended in 5 ml of toluene and heated up to reflux temperature at about 110° C. Suspension was left for 5 days at ambient conditions and then filtrated off. Obtained solid was identified as Form II per analysis by XRD.

Example 83: Preparation of Rucaparib Mixture of Form II and Form III

Procedure 1:

The sample of Rucaparib Form I was heated from 30° C. to 215° C. at 10° C./step and heating rate 10° C./min and then cooled at 30° C. XRPD pattern was acquired at 215° C. The sample temperature was controlled using Anton Paar TCU100 Temperature Control Unit.

Figure 37:
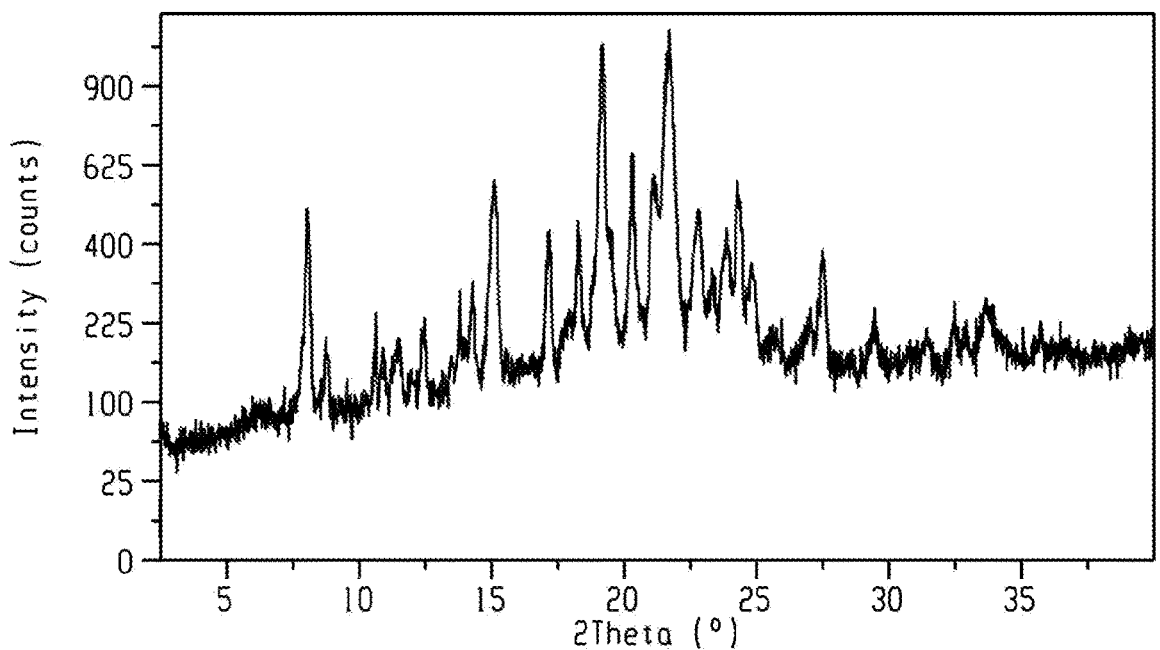
FIG. 37 shows an X-ray powder diffraction pattern of a mixture of Form II and Form III of Rucaparib base, obtained by Example 83.

The XRD pattern is given in FIG. 37.

Example 84: Preparation of Rucaparib Form A

Procedure 1:

500 mg of Rucaparib Form II was suspended in 50 ml of acetone and heated up to reflux temperature at about 55° C.

Suspension was cooled down to ambient conditions, stirred for 48 h hours and filtrated off. Obtained solid was analyzed by XRD.

The XRD pattern is given in FIG. 38.

Procedure 2:

50 mg of Rucaparib Form II was suspended in 5 ml of acetone and heated up to reflux temperature at about 55° C. Suspension was left for 5 days at ambient conditions and then filtrated off. Obtained solid was analyzed by XRD. Obtained solid was identified as Form A per analysis by XRD.

Example 85: Preparation of Rucaparib Form C

Procedure 1:

500 mg of Rucaparib Form II was suspended in 10 ml of 1-butanol and heated up to reflux temperature at about 115° C. Suspension was cooled down to ambient conditions, stirred for 24 hours and filtrated off. Obtained solid was analyzed by XRD.

XRD is given in FIG. 39.

Procedure 2:

500 mg of Rucaparib Form II was suspended in 50 ml of 1-butanol and heated up to reflux temperature at about 115° C. Suspension was cooled down to ambient conditions, stirred for 48 h hours and filtrated off. Obtained solid was analyzed by XRD. Obtained solid was identified as Form C per analysis by XRD.

Procedure 3:

500 mg of Rucaparib Form II was suspended in 50 ml of 2-propanol and heated up to reflux temperature at about 80° C. Suspension was cooled down to ambient conditions, stirred for 48 h hours and filtrated off. Obtained solid was analyzed by XRD. Obtained solid was identified as Form C per analysis by XRD.

Example 86: Preparation of Rucaparib Form D

Procedure 1:

500 mg of Rucaparib Form II was suspended in 10 ml of tetrahydrofuran and heated up to reflux temperature at about 80° C. Suspension was cooled down to ambient conditions, stirred for 24 hours and filtrated off. Obtained solid was analyzed by XRD.

The XRD pattern is given in FIG. 40.

Example 87: Preparation of Rucaparib Form F

Procedure 1:

500 mg of Rucaparib Form II was suspended in 10 ml of methanol and heated up to temperature at about 65° C. Suspension was cooled down to ambient conditions and filtrated off. Obtained solid was analyzed by XRD.

The XRD pattern is given in FIG. 41.

Example 88: Preparation of Rucaparib Form J

Procedure 1:

500 mg of Rucaparib Form II was suspended in 10 ml of acetonitrile and heated up to reflux temperature at about 80° C. Suspension was cooled down to ambient conditions, stirred for 24 hours and filtrated off. Obtained solid was analyzed by XRD.

The XRD pattern is given in FIG. 42.

Example 89: Preparation of Rucaparib Form K

Procedure 1:

500 mg of Rucaparib Form II was suspended in 10 ml of 1,4-dioxane and heated up to reflux temperature at about 100° C. Suspension was cooled down to ambient conditions, stirred for 24 hours and filtrated off. Obtained solid was analyzed by XRD.

The XRD pattern is given in FIG. 43.

Example 90: Preparation of Rucaparib Form L

Rucaparib base (Form C, 100 mg) was suspended in methyl ethyl ketone (15 mL) and stirred at 50° C. for 1 hour. The suspension was then cooled down to a temperature of about 25±2° C. and was stirred at this temperature for 1 hour. The obtained crystals were filtered off under vacuum and dried in vacuum oven at 50° C. for 4 hours to obtain 85 mg of material. The sample was analyzed by XRPD; Form L of Rucaparib base was obtained. The XRD pattern is given in FIG. 44.

Example 91: Preparation of Rucaparib Form M

Rucaparib base (2 g) was dissolved in N,N-dimethylacetamide (30 mL) while heating to a temperature of about 90-95° C. The obtained solution was then cooled down to a temperature of about 25±2° C. The obtained suspension was stirred at a temperature of about 25±2° C. for 17 hours. The obtained crystals were filtered off under vacuum and dried in vacuum oven at 50° C. for 4 hours to obtain 1.386 g of material. The sample was analyzed by XRPD; Form M of Rucaparib base was obtained. The XRD pattern is given in FIG. 45.

Example 92: Preparation of Form Alpha of Rucaparib S-Camsylate 1.23 mg of Rucaparib S-camyslate, Form C (known from U.S. Pat. No. 8,754,072) is suspended in 5 ml of acetonitrile:water mixture (1:2). The mixture is heated up to around 66° C. The obtained solution is cooled to around 53° C., by stirring at ambient conditions. After obtaining temperature of about 53° C., the solution is cooled down in media of −8° C. Crystallization occurs after 5 minutes. The obtained suspension is filtrated off. Isolated product is analyzed by XRD.

The XRD pattern is given in FIG. 46.

Example 93: Preparation of Amorphous form of Rucaparib S-Camsylate 56 mg of Rucaparib Form II and 44 mg of 1S-(+)-camphor-10-sulphonic acid are placed in an agate jar with 4 agate balls and milled on a rotation ball mill for 2.5 hours. The prepared sample was analyzed by XRD.

The XRD pattern is given in FIG. 47.

Example 94: Preparation of Form Beta of Rucaparib S-Camsylate

Sample of Amorphous Rucaparib S-camsylate described in Example 93 was placed in pin hole aluminum pan. The sample was subjected to thermal treatment on DSC Discovery TA instruments by heating the sample 2° C./min up to a temperature of 220° C. and then keeping sample isothermally for 5 minutes. Sample was cooled down to room condition and analyzed by XRD.

The XRD pattern is given in FIG. 48.

Example 95: Preparation of Form Gamma of Rucaparib S-Camsylate

Around 700 mg of amorphous Rucaparib camsylate is put in aluminum pan. Sample is heated from ambient temperature up to 200° C. in furnace and is kept at 200° C. for 90 minutes. Sample is cooled down at ambient conditions and analyzed by XRPD.

The XRD pattern is given in FIG. 49.

The invention claimed is:

1. A crystalline form of Rucaparib Hemi-Edisylate designated as Form IV, characterized by data selected from one or more of the following:
   an X-ray powder diffraction pattern substantially as depicted in FIG. 26;
   an X-ray powder diffraction pattern having peaks at 9.0, 13.1, 15.4, 16.9 and 23.1 degrees 2-theta±0.2 degrees 2-theta;
   a solid state $^{13}C$ NMR spectrum having characteristic peaks at 132.9, 138.0 and 173.5 ppm±0.2 ppm;
   a solid state $^{13}C$ NMR spectrum having the following chemical shift absolute differences from a reference peak at 112.1 ppm±2 ppm: 20.8, 25.9 and 61.4 ppm±0.1 ppm;
   a solid state $^{13}C$ NMR spectrum as depicted in FIG. 52a or 52b or 52c; and
   combinations of these data.

2. The crystalline form of Rucaparib Hemi-Edisylate according to claim 1, characterized by an X-ray powder diffraction pattern having peaks at 9.0, 13.1, 15.4, 16.9 and 23.1 degrees 2-theta±0.2 degrees 2-theta and also having any one, two, three, four or five additional peaks selected from the group consisting of 11.5, 17.4, 19.6, 21.7 and 25.6 degrees 2-theta±0.2 degrees 2-theta.

3. The crystalline form of Rucaparib Hemi-Edisylate according to claim 1, wherein the crystalline form is anhydrous.

4. A crystalline form of Rucaparib Tosylate designated as Form III, characterized by data selected from one or more of the following:
   an X-ray powder diffraction pattern substantially as depicted in FIG. 21;
   an X-ray powder diffraction pattern having peaks at 10.0, 13.8, 14.5, 17.0 and 18.5 degrees 2-theta±0.2 degrees 2-theta;
   a solid state $^{13}C$ NMR spectrum having characteristic peaks at 111.9, 125.2, 127.5, 142.3 and 144.8 ppm±0.2 ppm;
   a solid state $^{13}C$ NMR spectrum having the following chemical shift absolute differences from a reference peak at 101.4 ppm±2 ppm: 10.5, 23.8, 26.1, 34.7, 40.9 and 43.4 ppm±0.1 ppm;
   a solid state $^{13}C$ NMR spectrum as depicted in FIG. 53a or 53b or 53c; and
   combinations of these data.

5. The crystalline form of Rucaparib Tosylate according to claim 4, characterized by an X-ray powder diffraction pattern having peaks at 10.0, 13.8, 14.5, 17.0 and 18.5 degrees 2-theta±0.2 degrees 2-theta and also having any one, two, three, four or five additional peaks selected from the group consisting of 6.5, 20.4, 22.9, 23.7 and 25.8 degrees 2-theta±0.2 degrees 2-theta.

6. The crystalline form of Rucaparib Tosylate according to claim 4, wherein the crystalline form is anhydrous.

7. A crystalline form of Rucaparib Tosylate designated as Form V, characterized by data selected from one or more of the following:
   an X-ray powder diffraction pattern substantially as depicted in FIG. 23;
   an X-ray powder diffraction pattern having peaks at 7.1, 12.5, 14.4, 17.4 and 24.9 degrees 2-theta±0.2 degrees 2-theta;
   a solid state $^{13}C$ NMR spectrum having characteristic peaks at 111.2, 122.7, 123.8, 141.6 and 143.5 ppm±0.2 ppm;
   a solid state $^{13}C$ NMR spectrum having the following chemical shift absolute differences from a reference peak at 99.9 ppm±2 ppm: 11.3, 22.8, 23.9, 41.7 and 43.6 ppm±0.1 ppm;
   a solid state $^{13}C$ NMR spectrum as depicted in FIG. 54a or 54b or 54c; and
   combinations of these data.

8. The crystalline form of Rucaparib Tosylate according to claim 7, characterized by an X-ray powder diffraction pattern having peaks at 7.1, 12.5, 14.4, 17.4 and 24.9 degrees 2-theta±0.2 degrees 2-theta and also having any one, two, three, four or five additional peaks selected from the group consisting of 16.3, 18.6, 22.5, 24.2 and 26.0 degrees 2-theta±0.2 degrees 2-theta.

9. The crystalline form of Rucaparib Tosylate according to claim 7, wherein the crystalline form is anhydrous.

10. A crystalline form of Rucaparib base designated as Form I, characterized by data selected from one or more of the following:
    an X-ray powder diffraction pattern substantially as depicted in FIG. 34;
    an X-ray powder diffraction pattern having peaks at 9.2, 15.2, 17.2, 21.0 and 23.1 degrees 2-theta±0.2 degrees 2-theta;
    a solid state $^{13}C$ NMR spectrum having characteristic peaks at 123.0, 126.4 and 159.4 ppm±0.2 ppm;
    a solid state $^{13}C$ NMR spectrum having the following chemical shift absolute differences from a reference peak at 108.3 ppm±2 ppm: 14.7, 18.1 and 51.1 ppm±0.1 ppm;
    a solid state $^{13}C$ NMR spectrum as depicted in FIG. 50a or 50b or 50c; and
    combinations of these data.

11. The crystalline form of Rucaparib base according to claim 10, characterized by an X-ray powder diffraction pattern having peaks at 9.2, 15.2, 17.2, 21.0 and 23.1 degrees 2-theta±0.2 degrees 2-theta and also having any one, two or three additional peaks selected from the group consisting of 20.0, 24.1 and 28.4 degrees 2-theta±0.2 degrees 2-theta.

12. The crystalline form of Rucaparib base according to claim 10, wherein the crystalline form is a monohydrate.

13. A crystalline form of Rucaparib base designated as Form II, characterized by data selected from one or more of the following:
    an X-ray powder diffraction pattern substantially as depicted in FIG. 35 or 36;
    an X-ray powder diffraction pattern having peaks at 12.0, 14.4, 16.8, 18.8 and 24.3 degrees 2-theta±0.2 degrees 2-theta;
    a solid state $^{13}C$ NMR spectrum having characteristic peaks at 113.6, 122.6, 126.0, 128.4, 137.3 and 159.0 ppm±0.2 ppm;

a solid state $^{13}$C NMR spectrum having the following chemical shift absolute differences from a reference peak at 108.3 ppm±2 ppm: 5.3, 14.3, 17.7, 20.1, 29.0 and 50.7 ppm±0.1 ppm;

a solid state $^{13}$C NMR spectrum as depicted in FIG. 51*a* or 51*b* or 51*c*; and combinations of these data.

14. The crystalline form of Rucaparib base according to claim 13, characterized by an X-ray powder diffraction pattern having peaks at 12.0, 14.4, 16.8, 18.8 and 24.3 degrees 2-theta±0.2 degrees 2-theta and also having any one, two, three, four or five additional peaks selected from the group consisting of 20.2, 22.5, 29.8, 30.2 and 30.6 degrees 2-theta±0.2 degrees 2-theta.

15. The crystalline form of Rucaparib base according to claim 13, wherein the crystalline form is anhydrous.

16. The crystalline form of Rucaparib base according to claim 10, which contains not more than 10% (w/w) of any crystalline form.

17. The crystalline form of Rucaparib base according to claim 10, which contains not more than 10% (w/w) of Crystalline form X1 and/or X2 of Rucaparib base.

18. The crystalline form of Rucaparib base according to claim 10, which contains not more than 5% (w/w) of any crystalline form.

19. The crystalline form of Rucaparib base according to claim 10, which contains not more than 5% (w/w) of Crystalline form X1 and/or X2 of Rucaparib base.

20. The crystalline form of Rucaparib base according to claim 10, which contains not more than 1% (w/w) of any crystalline form.

21. The crystalline form of Rucaparib base according to claim 10, which contains not more than 1% (w/w) of Crystalline form X1 and/or X2 of Rucaparib base.

22. A crystalline form of Rucaparib base designated as Form C, characterized by data selected from one or more of the following:

an X-ray powder diffraction pattern substantially as depicted in FIG. 39;

an X-ray powder diffraction pattern having peaks at 10.5, 16.3, 19.7 and 21.4, and 22.2 degrees 2-theta±0.2 degrees 2-theta; and combinations of these data.

23. The crystalline form of Rucaparib base according to claim 22, characterized by an X-ray powder diffraction pattern having peaks at 10.5, 16.3, 19.7 and 21.4, and 22.2 degrees 2-theta±0.2 degrees 2-theta and also having any one, two, three, four or five additional peaks selected from the group consisting of 8.8, 15.5, 17.7, 18.4 and 26.7 degrees 2-theta±0.2 degrees 2-theta.

24. The crystalline form of Rucaparib base according to claim 22, wherein the crystalline form is anhydrous.

25. A method of treating ovarian cancer, comprising administering a therapeutically effective amount of the crystalline form according to claim 1 to a subject suffering from ovarian cancer.

26. A process for preparing Rucaparib salt or a solid state form thereof comprising preparing the crystalline form of Rucaparib according to claim 1, and converting it to Rucaparib salt or a solid state form thereof.

\* \* \* \* \*